United States Patent
Dobson et al.

(10) Patent No.: US 9,255,144 B2
(45) Date of Patent: Feb. 9, 2016

(54) ANTI-IL-18 ANTIBODIES AND THEIR USES

(75) Inventors: Claire Dobson, Cambridge (GB); Steven Lane, Cambridge (GB); Philip Newton, Cambridge (GB); Martin Schwickart, Oakland, CA (US); Ann-Charlott Steffen, Cambridge (SE)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 13/993,537

(22) PCT Filed: Dec. 20, 2011

(86) PCT No.: PCT/EP2011/073496
§ 371 (c)(1),
(2), (4) Date: Sep. 5, 2013

(87) PCT Pub. No.: WO2012/085015
PCT Pub. Date: Jun. 28, 2012

(65) Prior Publication Data
US 2014/0004128 A1 Jan. 2, 2014

Related U.S. Application Data

(60) Provisional application No. 61/424,920, filed on Dec. 20, 2010.

(51) Int. Cl.
*A61K 39/00* (2006.01)
*A61K 39/395* (2006.01)
*C07K 16/00* (2006.01)
*C07K 16/24* (2006.01)

(52) U.S. Cl.
CPC ......... *C07K 16/244* (2013.01); *A61K 2039/505* (2013.01); *C07K 2299/00* (2013.01); *C07K 2317/21* (2013.01); *C07K 2317/33* (2013.01); *C07K 2317/34* (2013.01); *C07K 2317/52* (2013.01); *C07K 2317/55* (2013.01); *C07K 2317/565* (2013.01); *C07K 2317/622* (2013.01); *C07K 2317/76* (2013.01); *C07K 2317/92* (2013.01); *C07K 2319/00* (2013.01)

(58) Field of Classification Search
None
See application file for complete search history.

(56) References Cited

FOREIGN PATENT DOCUMENTS

| EP | 1 621 616 A1 | 2/2006 |
|---|---|---|
| EP | 1 705 191 A2 | 9/2006 |
| WO | WO 01/58956 A2 * | 8/2001 |
| WO | WO 2005/047307 A2 | 5/2005 |
| WO | WO 2009/099545 A1 * | 8/2009 |

OTHER PUBLICATIONS

Cao, Qizhen et al., 2008, "Multimodality Imaging of IL-18-Binding Protein-Fc Therapy of Experimental Lung Metastasis", Clinical Cancer Research, 14(19):6137-6145.
International Search Report corresponding to PCT/EP2011/073496.
Wu, Chengbin et al., 2003, "IL-18 Receptor β-Induced Changes in the Presentation of IL-18 Binding Site Affect Ligand Binding and Signal Transduction", The Journal of Immunology, 170:5571-5577.

* cited by examiner

*Primary Examiner* — Elizabeth C Kemmerer

(57) ABSTRACT

The present invention provides human, humanized and/or chimeric antibodies as well as fragments, derivatives/conjugates and compositions thereof with a specific binding affinity for interleukin-18. The invention includes the use of these antibodies for diagnosing and treating diseases associated with increased IL-18 activity, the latter in the form of a pharmaceutical composition.

13 Claims, 16 Drawing Sheets

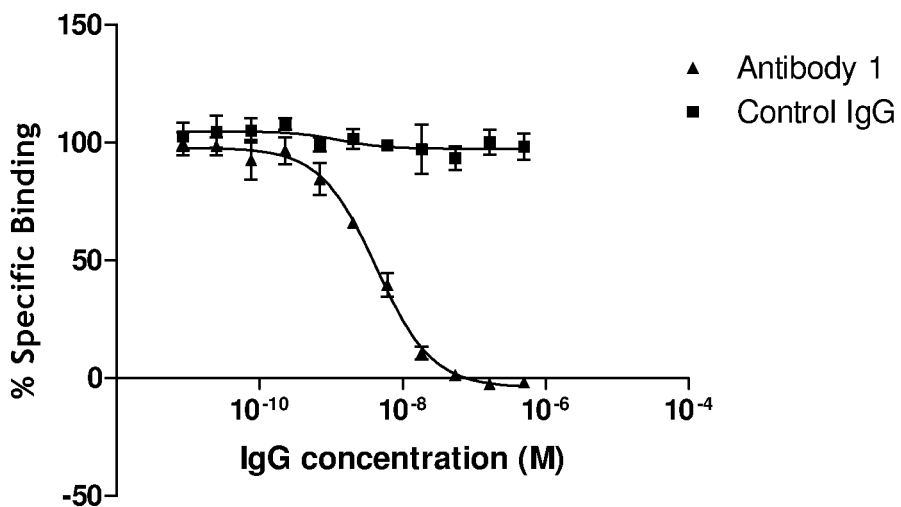
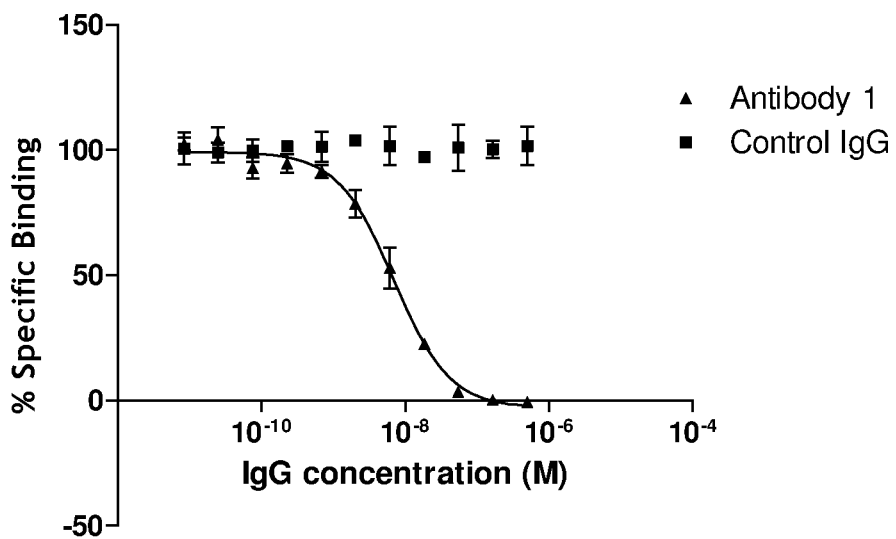
FIGURE 2

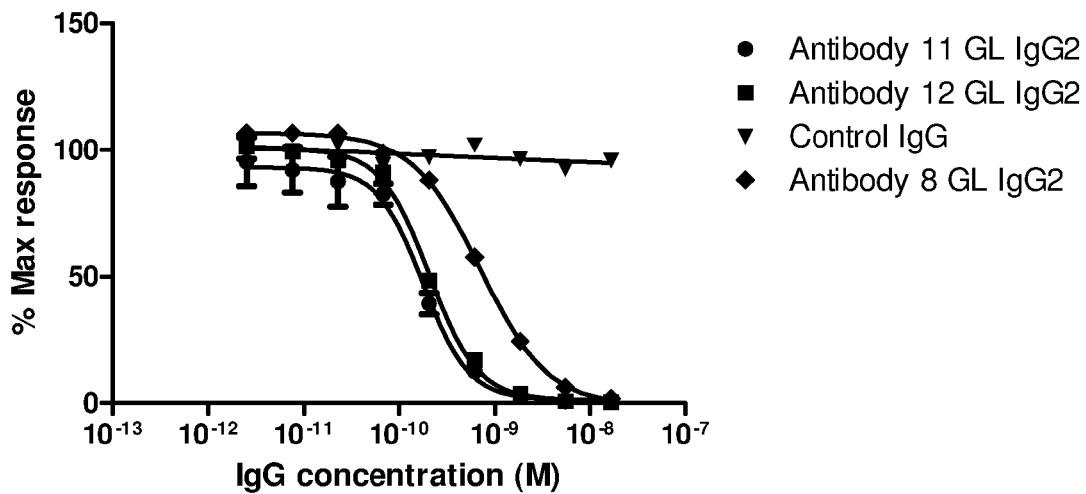
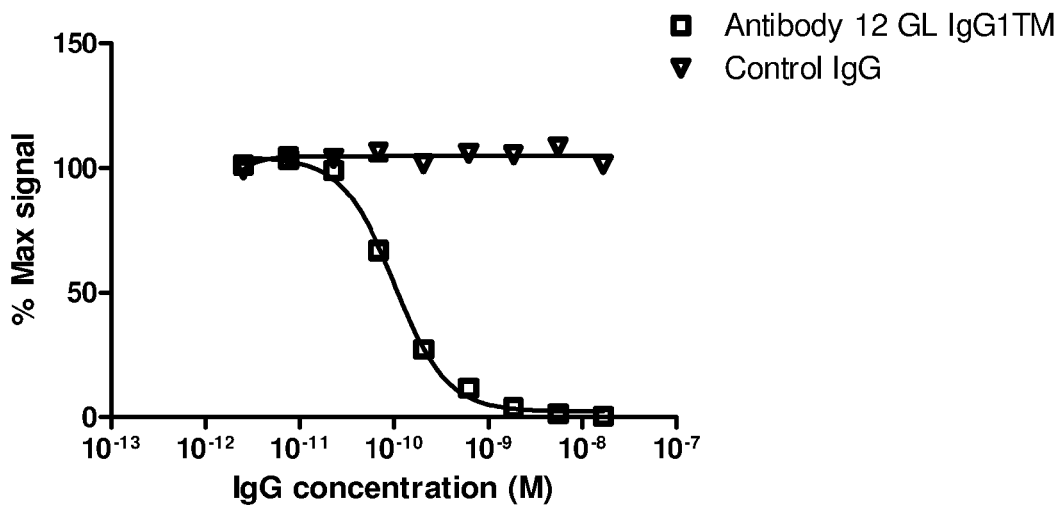
FIGURE 6

A
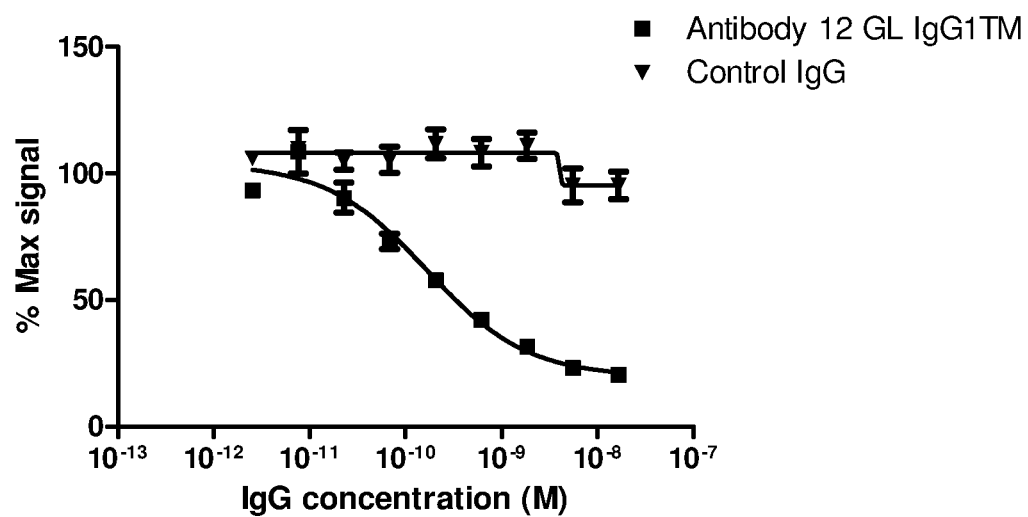
B
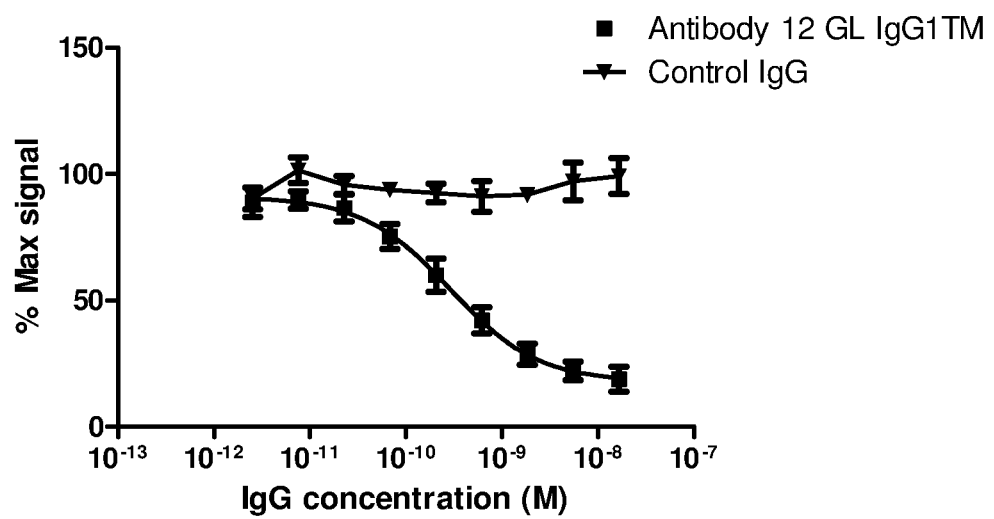
FIGURE 7

A
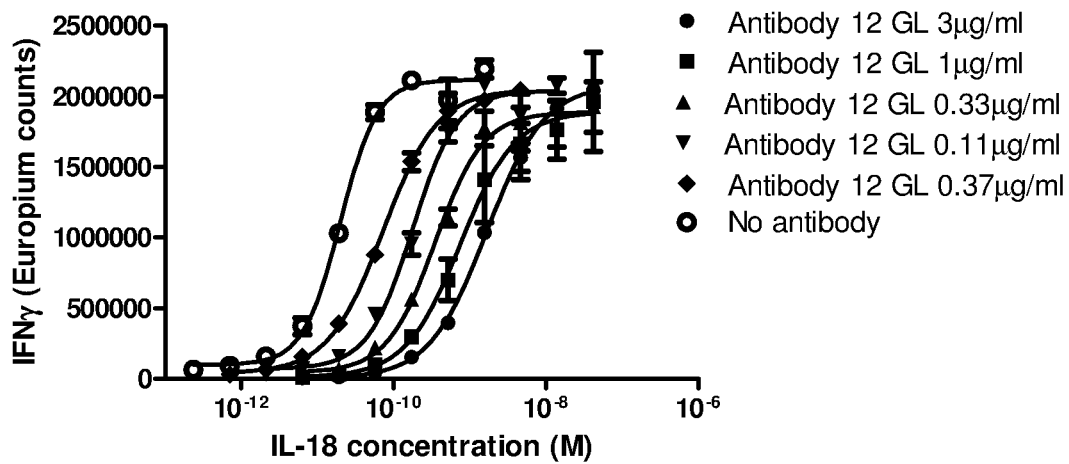
B
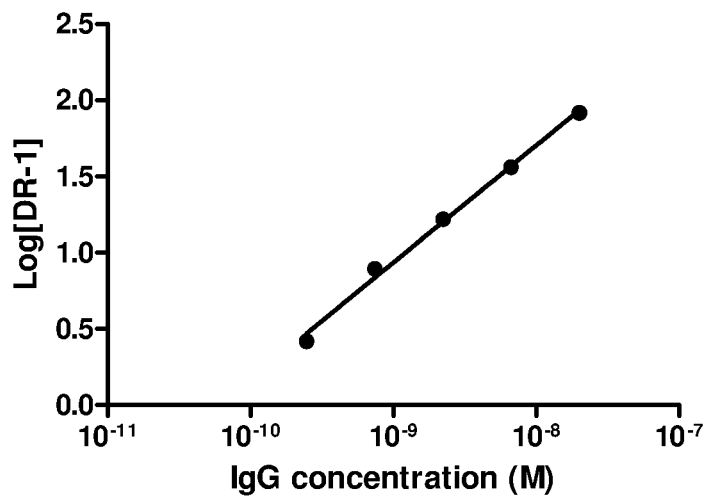
FIGURE 10

Antibody 12 GL    YFGKLESKLSVIRNLNDQVLFIDQGNRPLFEDMTDSDCRDNAPRTIFIISMY
IL18-BP           YFGKLESKLSVIRNLNDQVLFIDQGNRPLFEDMTDSDCRDNAPRTIFIISMY Antibody 12 GL    KDSQPRGMAVTISVKCEKISTLSCENKIISFKEMNPPDNIKDTKSDIIFFQRSV
IL18-BP           KDSQPRGMAVTISVKCEKISTLSCENKIISFKEMNPPDNIKDTKSDIIFFQRSV Antibody 12 GL    PGHDNKMQFESSSYE Light chain, variable domain:

| FW1 | CDR1 | FW2 | CDR2 |
|---|---|---|---|
| DIQMTQSPSTLSASVGDRVTITC (1) | RASQGISSWLA (30 32) | WYQQKPGKAPKVLIY | KASTLES |

| FW3 | CDR3 | FW4 |
|---|---|---|
| GVPSRFSGSGSGTEFTLTISSLQPDDFATYYC | QQSHHPPWT (91 94 96) | FGQGTKLEIK |

FIGURE 14A

Heavy chain, variable domain:

| FW1 | CDR1 | FW2 | CDR2 |
|---|---|---|---|
| QVQLQESGPGLVKPSETLSLTCTVSGGSIS | ADGYYWS (35) | WIRQPPGKGLEWIG | SLYYSGSTYYNPSLKG (52 53 58) |

| FW3 | CDR3 | FW4 |
|---|---|---|
| RVTISGDTSKNQFSLKLSSVTAADTAVYYCAR | TPAYFGQDRTDFFDV (97 100 100E) | WGRGTLVTVSS |

FIGURE 14B

SEQUENCE LISTING

```
<160> NUMBER OF SEQ ID NOS: 171

<210> SEQ ID NO 1
<211> LENGTH: 375
<212> TYPE: DNA
<213> ORGANISM: Homo sapiens

<400> SEQUENCE: 1
caggtacagc tgcagcagtc aggcccaaga ctggtgaagc cttcacagac cctgtccctc      60
acctgcactg tctctggtgg ctccatcagc agtggtggtt actactggag ctggatccgg     120
cagcccgccg ggaaggggct ggagtggatt gggagtatct attatagtgg gagcacctac     180
tacaacccgt ccctcaagag tcgagtcacc atatcaggag acacgcccaa gaaccagttc     240
tccctgaagc tgagctctgt gaccgctgcg gacacggccg tatattactg tgcaagaacc     300
cccgcgtatg atggcgatgc ccgggcagat ttctttgacg tctggggcag gggaaccctg     360
gtcaccgtct cctca                                                      375

<210> SEQ ID NO 2
<211> LENGTH: 125
<212> TYPE: PRT
<213> ORGANISM: Homo sapiens

<400> SEQUENCE: 2

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60
```

```
Leu Lys Ser Arg Val Thr Ile Ser Gly Asp Thr Pro Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
            115                 120                 125

<210> SEQ ID NO 3
<211> LENGTH: 7
<212> TYPE: PRT
<213> ORGANISM: Homo sapiens

<400> SEQUENCE: 3

Ser Gly Gly Tyr Tyr Trp Ser
1               5

<210> SEQ ID NO 4
<211> LENGTH: 16
<212> TYPE: PRT
<213> ORGANISM: Homo sapiens

<400> SEQUENCE: 4

Ser Ile Tyr Tyr Ser Gly Ser Thr Tyr Tyr Asn Pro Ser Leu Lys Ser
1               5                   10                  15

<210> SEQ ID NO 5
<211> LENGTH: 15
<212> TYPE: PRT
<213> ORGANISM: Homo sapiens

<400> SEQUENCE: 5

Thr Pro Ala Tyr Asp Gly Asp Ala Arg Ala Asp Phe Phe Asp Val
1               5                   10                  15

<210> SEQ ID NO 6
<211> LENGTH: 321
<212> TYPE: DNA
<213> ORGANISM: Homo sapiens

<400> SEQUENCE: 6
gacatcgtga tgacccagtc tccttccacc ctgtctgcat ctgtaggaga cagagtcacc    60
atcacttgcc gggccagtca gggtattagt agctggttgg cctggtatca gcagaaacca   120
gggagagccc ctaaggtctt gatctataag gcatctactt tagaaagtgg ggtcccatca   180
aggttcagcg gcagtggatc tgggacagat ttcactctca ccatcagcag tctgcaacct   240
gaagattttg caacttacta ctgtcaacag agttacagta ccccgtggac gttcggccaa   300
gggaccaagc tggagatcaa a                                             321

<210> SEQ ID NO 7
<211> LENGTH: 107
<212> TYPE: PRT
<213> ORGANISM: Homo sapiens

<400> SEQUENCE: 7

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30
```

```
Leu Ala Trp Tyr Gln Gln Lys Pro Gly Arg Ala Pro Lys Val Leu Ile
            35                  40                  45

Tyr Lys Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gln Gly Thr Lys Leu Glu Ile Lys
            100                 105
```

<210> SEQ ID NO 8
<211> LENGTH: 11
<212> TYPE: PRT
<213> ORGANISM: Homo sapiens

<400> SEQUENCE: 8

```
Arg Ala Ser Gln Gly Ile Ser Ser Trp Leu Ala
 1               5                  10
```

<210> SEQ ID NO 9
<211> LENGTH: 7
<212> TYPE: PRT
<213> ORGANISM: Homo sapiens

<400> SEQUENCE: 9

```
Lys Ala Ser Thr Leu Glu Ser
 1               5
```

<210> SEQ ID NO 10
<211> LENGTH: 9
<212> TYPE: PRT
<213> ORGANISM: Homo sapiens

<400> SEQUENCE: 10

```
Gln Gln Ser Tyr Ser Thr Pro Trp Thr
 1               5
```

<210> SEQ ID NO 11
<211> LENGTH: 375
<212> TYPE: DNA
<213> ORGANISM: Homo sapiens

<400> SEQUENCE: 11

```
caggtacagc tgcaggagtc aggcccagga ctggtgaagc cttcagagac cctgtccctc      60
acctgcactg tctctggtgg ctccatcagc agtggtggtt actactggag ctggatccgg     120
cagccccccg ggaagggct ggagtggatt gggagtatct attatagtgg gagcacctac     180
tacaacccgt ccctcaagag tcgagtcacc atatcaggag acacgtccaa gaaccagttc     240
tccctgaagc tgagctctgt gaccgctgcg gacacggccg tatattactg tgcaagaacc     300
cccgcgtatg atggcgatgc ccgggcagat ttctttgacg tctggggcag gggaaccctg     360
gtcaccgtct cctca                                                      375
```

<210> SEQ ID NO 12
<211> LENGTH: 125
<212> TYPE: PRT
<213> ORGANISM: Homo sapiens

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125

<210> SEQ ID NO 13
<211> LENGTH: 7
<212> TYPE: PRT
<213> ORGANISM: Homo sapiens

<400> SEQUENCE: 13

Ser Gly Gly Tyr Tyr Trp Ser
1               5

<210> SEQ ID NO 14
<211> LENGTH: 16
<212> TYPE: PRT
<213> ORGANISM: Homo sapiens

<400> SEQUENCE: 14

Ser Ile Tyr Tyr Ser Gly Ser Thr Tyr Tyr Asn Pro Ser Leu Lys Ser
1               5                   10                  15

<210> SEQ ID NO 15
<211> LENGTH: 15
<212> TYPE: PRT
<213> ORGANISM: Homo sapiens

<400> SEQUENCE: 15

Thr Pro Ala Tyr Asp Gly Asp Ala Arg Ala Asp Phe Phe Asp Val
1               5                   10                  15

<210> SEQ ID NO 16
<211> LENGTH: 321
<212> TYPE: DNA
<213> ORGANISM: Homo sapiens

<400> SEQUENCE: 16
gacatccaga tgacccagtc tccttccacc ctgtctgcat ctgtaggaga cagagtcacc      60
atcacttgcc gggccagtca gggtattagt agctggttgg cctggtatca gcagaaacca     120
gggaaagccc ctaaggtctt gatctataag gcatctactt tagaaagtgg ggtcccatca     180
aggttcagcg gcagtggatc tgggacagaa ttcactctca ccatcagcag tctgcaacct     240
gatgattttg caacttacta ctgtcaacag agttacagta ccccgtggac gttcggccaa     300
gggaccaagc tggagatcaa a                                               321

```
<210> SEQ ID NO 17
<211> LENGTH: 107
<212> TYPE: PRT
<213> ORGANISM: Homo sapiens

<400> SEQUENCE: 17

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105

<210> SEQ ID NO 18
<211> LENGTH: 11
<212> TYPE: PRT
<213> ORGANISM: Homo sapiens

<400> SEQUENCE: 18

Arg Ala Ser Gln Gly Ile Ser Ser Trp Leu Ala
1               5                   10

<210> SEQ ID NO 19
<211> LENGTH: 7
<212> TYPE: PRT
<213> ORGANISM: Homo sapiens

<400> SEQUENCE: 19

Lys Ala Ser Thr Leu Glu Ser
1               5

<210> SEQ ID NO 20
<211> LENGTH: 9
<212> TYPE: PRT
<213> ORGANISM: Homo sapiens

<400> SEQUENCE: 20

Gln Gln Ser Tyr Ser Thr Pro Trp Thr
1               5

<210> SEQ ID NO 21
<211> LENGTH: 375
<212> TYPE: DNA
<213> ORGANISM: Homo sapiens

<400> SEQUENCE: 21
caggtacagc tgcagcagtc aggcccaaga ctggtgaagc cttcacagac cctgtccctc     60
acctgcactg tctctggtgg ctccatcagc agtggtggtt actactggag ctggatccgg    120
cagcccgccg ggaagggct  ggagtggatt gggagtatct attatagtgg gagcacctac    180
tacaacccgt ccctcaagag tcgagtcacc atatcaggag acacgccaa  gaaccagttc    240 tccctgaagc tgagctctgt gaccgctgcg gacacggccg tatattactg tgcaagaacc    300
```

```
cccgcgtatg atggcgatgc ccgggcagat ttctttgacg tctggggcag gggaaccctg    360
gtcaccgtct cctca                                                     375
```

<210> SEQ ID NO 22
<211> LENGTH: 125
<212> TYPE: PRT
<213> ORGANISM: Homo sapiens

<400> SEQUENCE: 22

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125

<210> SEQ ID NO 23
<211> LENGTH: 7
<212> TYPE: PRT
<213> ORGANISM: Homo sapiens

<400> SEQUENCE: 23

Ser Gly Gly Tyr Tyr Trp Ser
1               5

<210> SEQ ID NO 24
<211> LENGTH: 16
<212> TYPE: PRT
<213> ORGANISM: Homo sapiens

<400> SEQUENCE: 24

Ser Ile Tyr Tyr Ser Gly Ser Thr Tyr Tyr Asn Pro Ser Leu Lys Ser
1               5                   10                  15

<210> SEQ ID NO 25
<211> LENGTH: 15
<212> TYPE: PRT
<213> ORGANISM: Homo sapiens

<400> SEQUENCE: 25

Thr Pro Ala Tyr Asp Gly Asp Ala Arg Ala Asp Phe Phe Asp Val
1               5                   10                  15

<210> SEQ ID NO 26
<211> LENGTH: 321
<212> TYPE: DNA
<213> ORGANISM: Homo sapiens

<400> SEQUENCE: 26

```
gacatcgtga tgacccagtc tccttccacc ctgtctgcat ctgtaggaga cagagtcacc    60
atcacttgcc gggccagtca gggtattagt agctggttgg cctggtatca gcagaaacca   120
gggagagccc ctaaggtctt gatctataag gcatctactt tagaaagtgg ggtcccatca   180
aggttcagcg gcagtggatc tgggacagat ttcactctca ccatcagcag tctgcaacct   240
gaagattttg caacttacta ctgtcaggac atctccttcc ccccgtggac gttcggccaa   300
gggaccaagc tggagatcaa a                                             321
```

<210> SEQ ID NO 27
<211> LENGTH: 107
<212> TYPE: PRT
<213> ORGANISM: Homo sapiens

<400> SEQUENCE: 27

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asp Ile Ser Phe Pro Pro Trp
                85                  90                  95

Thr Phe Gly Gln Gly Thr Lys Leu Glu Ile Lys
            100                 105
```

<210> SEQ ID NO 28
<211> LENGTH: 11
<212> TYPE: PRT
<213> ORGANISM: Homo sapiens

<400> SEQUENCE: 28

```
Arg Ala Ser Gln Gly Ile Ser Ser Trp Leu Ala
1               5                   10
```

<210> SEQ ID NO 29
<211> LENGTH: 7
<212> TYPE: PRT
<213> ORGANISM: Homo sapiens

<400> SEQUENCE: 29

```
Lys Ala Ser Thr Leu Glu Ser
1               5
```

<210> SEQ ID NO 30
<211> LENGTH: 9
<212> TYPE: PRT
<213> ORGANISM: Homo sapiens

<400> SEQUENCE: 30

```
Gln Asp Ile Ser Phe Pro Pro Trp Thr
1               5
```

```
<210> SEQ ID NO 31
<211> LENGTH: 375
<212> TYPE: DNA
<213> ORGANISM: Homo sapiens

<400> SEQUENCE: 31
caggtacagc tgcagcagtc aggcccaaga ctggtgaagc cttcacagac cctgtccctc      60
acctgcactg tctctggtgg ctccatcagc agtggtggtt actactggag ctggatccgg     120
cagcccgccg ggaaggggct ggagtggatt gggagtatct attatagtgg gagcacctac     180
tacaacccgt ccctcaagag tcgagtcacc atatcaggag acacgcccaa gaaccagttc     240
tccctgaagc tgagctctgt gaccgctgcg gacacggccg tatattactg tgcaagaacc     300
cccgcgtatg atggcgatgc ccgggcagat ttctttgacg tctggggcag gggcaccctg     360
gtcaccgtct cctca                                                     375

<210> SEQ ID NO 32
<211> LENGTH: 125
<212> TYPE: PRT
<213> ORGANISM: Homo sapiens

<400> SEQUENCE: 32

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Thr Pro Ala Tyr Asp Gly Asp Ala Arg Ala Asp Phe Phe
        100                 105                 110

Asp Val Trp Gly Arg Gly Thr Leu Val Thr Val Ser Ser
    115                 120                 125

<210> SEQ ID NO 33
<211> LENGTH: 7
<212> TYPE: PRT
<213> ORGANISM: Homo sapiens

<400> SEQUENCE: 33

Ser Gly Gly Tyr Tyr Trp Ser
1               5

<210> SEQ ID NO 34
<211> LENGTH: 16
<212> TYPE: PRT
<213> ORGANISM: Homo sapiens

<400> SEQUENCE: 34

Ser Ile Tyr Tyr Ser Gly Ser Thr Tyr Tyr Asn Pro Ser Leu Lys Ser
1               5                   10                  15
```

<210> SEQ ID NO 35
<211> LENGTH: 15
<212> TYPE: PRT
<213> ORGANISM: Homo sapiens

<400> SEQUENCE: 35

Thr Pro Ala Tyr Asp Gly Asp Ala Arg Ala Asp Phe Phe Asp Val
1               5                   10                  15

<210> SEQ ID NO 36
<211> LENGTH: 321
<212> TYPE: DNA
<213> ORGANISM: Homo sapiens

<400> SEQUENCE: 36
gacatcgtga tgacccagtc tccttccacc ctgtctgcat ctgtaggaga cagagtcacc    60
atcacttgcc gggccagtca gggtattagt agctggttgg cctggtatca gcagaaacca   120
gggagagccc ctaaggtctt gatctataag gcatctactt tagaaagtgg ggtcccatca   180
aggttcagcg gcagtggatc tgggacagat ttcactctca ccatcagcag tctgcaacct   240
gaagattttg caacttacta ctgtcagcag agcctctacc ccccgtggac gttcggccaa   300
gggaccaagc tggagatcaa a                                             321

<210> SEQ ID NO 37
<211> LENGTH: 107
<212> TYPE: PRT
<213> ORGANISM: Homo sapiens

<400> SEQUENCE: 37

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Pro Pro Trp
                85                  90                  95

Thr Phe Gly Gln Gly Thr Lys Leu Glu Ile Lys
            100                 105

<210> SEQ ID NO 38
<211> LENGTH: 11
<212> TYPE: PRT
<213> ORGANISM: Homo sapiens

<400> SEQUENCE: 38

Arg Ala Ser Gln Gly Ile Ser Ser Trp Leu Ala
1               5                   10

<210> SEQ ID NO 39
<211> LENGTH: 7
<212> TYPE: PRT
<213> ORGANISM: Homo sapiens

<400> SEQUENCE: 39

Lys Ala Ser Thr Leu Glu Ser
1               5

<210> SEQ ID NO 40
<211> LENGTH: 9
<212> TYPE: PRT
<213> ORGANISM: Homo sapiens

<400> SEQUENCE: 40

Gln Gln Ser Leu Tyr Pro Pro Trp Thr
1               5

<210> SEQ ID NO 41
<211> LENGTH: 375
<212> TYPE: DNA
<213> ORGANISM: Homo sapiens

<400> SEQUENCE: 41
caggtacagc tgcagcagtc aggcccaaga ctggtgaagc cttcacagac cctgtccctc      60
acctgcactg tctctggtgg ctccatcagc agtggtggtt actactggag ctggatccgg     120
cagcccgccg ggaaggggct ggagtggatt gggagtatct attatagtgg gagcacctac     180
tacaacccgt ccctcaagag tcgagtcacc atatcaggag acacgcccaa gaaccagttc     240
tccctgaagc tgagctctgt gaccgctgcg gacacggccg tatattactg tgcaagaacc     300
cccgcgtatg atggcgatgc ccgggcagat ttctttgacg tctggggcag gggcaccctg     360
gtcaccgtct cctca                                                     375

<210> SEQ ID NO 42
<211> LENGTH: 125
<212> TYPE: PRT
<213> ORGANISM: Homo sapiens

<400> SEQUENCE: 42

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125

<210> SEQ ID NO 43
<211> LENGTH: 7
<212> TYPE: PRT
<213> ORGANISM: Homo sapiens

<400> SEQUENCE: 43

Ser Gly Gly Tyr Tyr Trp Ser
1               5

<210> SEQ ID NO 44
<211> LENGTH: 16
<212> TYPE: PRT
<213> ORGANISM: Homo sapiens

<400> SEQUENCE: 44

Ser Ile Tyr Tyr Ser Gly Ser Thr Tyr Tyr Asn Pro Ser Leu Lys Ser
1               5                   10                  15

<210> SEQ ID NO 45
<211> LENGTH: 15
<212> TYPE: PRT
<213> ORGANISM: Homo sapiens

<400> SEQUENCE: 45

Thr Pro Ala Tyr Asp Gly Asp Ala Arg Ala Asp Phe Phe Asp Val
1               5                   10                  15

<210> SEQ ID NO 46
<211> LENGTH: 321
<212> TYPE: DNA
<213> ORGANISM: Homo sapiens

<400> SEQUENCE: 46
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agtcaccacc cgaactggga cttcggccaa     300
gggaccaagc tggagatcaa a                                              321

<210> SEQ ID NO 47
<211> LENGTH: 107
<212> TYPE: PRT
<213> ORGANISM: Homo sapiens

<400> SEQUENCE: 47

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Asn Trp
                85                  90                  95

Asp Phe Gly Gln Gly Thr Lys Leu Glu Ile Lys
            100                 105

<210> SEQ ID NO 48
<211> LENGTH: 11
<212> TYPE: PRT
<213> ORGANISM: Homo sapiens

<400> SEQUENCE: 48

Arg Ala Ser Gln Gly Ile Ser Ser Trp Leu Ala
1               5                   10

<210> SEQ ID NO 49
<211> LENGTH: 7
<212> TYPE: PRT
<213> ORGANISM: Homo sapiens

<400> SEQUENCE: 49

Lys Ala Ser Thr Leu Glu Ser
1               5

<210> SEQ ID NO 50
<211> LENGTH: 9
<212> TYPE: PRT
<213> ORGANISM: Homo sapiens

<400> SEQUENCE: 50

Gln Gln Ser His His Pro Asn Trp Asp
1               5

<210> SEQ ID NO 51
<211> LENGTH: 375
<212> TYPE: DNA
<213> ORGANISM: Homo sapiens

<400> SEQUENCE: 51
caggtacagc tgcagcagtc aggcccaaga ctggtgaagc cttcacagac cctgtccctc    60
acctgcactg tctctggtgg ctccatcagc agtggtggtt actactggag ctggatccgg   120
cagcccgccg ggaaggggct ggagtggatt gggagtatct attatagtgg gagcacctac   180
tacaacccgt ccctcaagag tcgagtcacc atatcaggag acacgccaa gaaccagttc    240 tccctgaagc tgagctctgt gaccgctgcg gacacggccg tatattactg tgcaagaacc   300
cccgcgtatg atggcgatgc ccgggcagat ttctttgacg tctggggcag gggcaccctg   360
gtcaccgtct cctca                                                    375

<210> SEQ ID NO 52
<211> LENGTH: 125
<212> TYPE: PRT
<213> ORGANISM: Homo sapiens

<400> SEQUENCE: 52

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125

<210> SEQ ID NO 53
<211> LENGTH: 7
<212> TYPE: PRT
<213> ORGANISM: Homo sapiens

<400> SEQUENCE: 53

Ser Gly Gly Tyr Tyr Trp Ser
1               5

<210> SEQ ID NO 54
<211> LENGTH: 16
<212> TYPE: PRT
<213> ORGANISM: Homo sapiens

<400> SEQUENCE: 54

Ser Ile Tyr Tyr Ser Gly Ser Thr Tyr Tyr Asn Pro Ser Leu Lys Ser
1               5                   10                  15

<210> SEQ ID NO 55
<211> LENGTH: 15
<212> TYPE: PRT
<213> ORGANISM: Homo sapiens

<400> SEQUENCE: 55

Thr Pro Ala Tyr Asp Gly Asp Ala Arg Ala Asp Phe Phe Asp Val
1               5                   10                  15

<210> SEQ ID NO 56
<211> LENGTH: 321
<212> TYPE: DNA
<213> ORGANISM: Homo sapiens

<400> SEQUENCE: 56

```
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agtctcatcc cgcagtggga cttcggccaa     300
gggaccaagc tggagatcaa a                                                321
```

<210> SEQ ID NO 57
<211> LENGTH: 107
<212> TYPE: PRT
<213> ORGANISM: Homo sapiens

<400> SEQUENCE: 57

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Ile Pro Gln Trp

```
                   85                  90                  95

Asp Phe Gly Gln Gly Thr Lys Leu Glu Ile Lys
               100                 105

<210> SEQ ID NO 58
<211> LENGTH: 11
<212> TYPE: PRT
<213> ORGANISM: Homo sapiens

<400> SEQUENCE: 58

Arg Ala Ser Gln Gly Ile Ser Ser Trp Leu Ala
1               5                  10

<210> SEQ ID NO 59
<211> LENGTH: 7
<212> TYPE: PRT
<213> ORGANISM: Homo sapiens

<400> SEQUENCE: 59

Lys Ala Ser Thr Leu Glu Ser
1               5

<210> SEQ ID NO 60
<211> LENGTH: 9
<212> TYPE: PRT
<213> ORGANISM: Homo sapiens

<400> SEQUENCE: 60

Gln Gln Ser Leu Ile Pro Gln Trp Asp
1               5

<210> SEQ ID NO 61
<211> LENGTH: 375
<212> TYPE: DNA
<213> ORGANISM: Homo sapiens

<400> SEQUENCE: 61
caggtacagc tgcagcagtc aggcccaaga ctggtgaagc cttcacagac cctgtccctc      60
acctgcactg tctctggtgg ctccatcagc agtggtggtt actactggag ctggatccgg     120
cagcccgccg ggaaggggct ggagtggatt gggagtatct attatagtgg gagcacctac     180
tacaacccgt ccctcaagag tcgagtcacc atatcaggag acacgcccaa gaaccagttc     240
tccctgaagc tgagctctgt gaccgctgcg gacacggccg tatattactg tgcaagaacc     300
cccgcgtatt tcggccagga caggacggat ttctttgacg tctggggcag ggaaccctg     360 gtcaccgtct cctca                                                     375

<210> SEQ ID NO 62
<211> LENGTH: 125
<212> TYPE: PRT
<213> ORGANISM: Homo sapiens

<400> SEQUENCE: 62

Gln Val Gln Leu Gln Gln Ser Gly Pro Arg Leu Val Lys Pro Ser Gln
1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60
```

Leu Lys Ser Arg Val Thr Ile Ser Gly Asp Thr Pro Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 63
<211> LENGTH: 7
<212> TYPE: PRT
<213> ORGANISM: Homo sapiens

<400> SEQUENCE: 63

Ser Gly Gly Tyr Tyr Trp Ser
1               5

<210> SEQ ID NO 64
<211> LENGTH: 16
<212> TYPE: PRT
<213> ORGANISM: Homo sapiens

<400> SEQUENCE: 64

Ser Ile Tyr Tyr Ser Gly Ser Thr Tyr Tyr Asn Pro Ser Leu Lys Ser
1               5                   10                  15

<210> SEQ ID NO 65
<211> LENGTH: 15
<212> TYPE: PRT
<213> ORGANISM: Homo sapiens

<400> SEQUENCE: 65

Thr Pro Ala Tyr Phe Gly Gln Asp Arg Thr Asp Phe Phe Asp Val
1               5                   10                  15

<210> SEQ ID NO 66
<211> LENGTH: 321
<212> TYPE: DNA
<213> ORGANISM: Homo sapiens

<400> SEQUENCE: 66
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtgccaac atcgccttcc ccccgtggac gttcggccaa     300
gggaccaagc tggagatcaa a                                               321

<210> SEQ ID NO 67
<211> LENGTH: 107
<212> TYPE: PRT
<213> ORGANISM: Homo sapiens

<400> SEQUENCE: 67

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
            35                  40                  45

Tyr Lys Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Asn Ile Ala Phe Pro Pro Trp
                85                  90                  95

Thr Phe Gly Gln Gly Thr Lys Leu Glu Ile Lys
            100                 105

<210> SEQ ID NO 68
<211> LENGTH: 11
<212> TYPE: PRT
<213> ORGANISM: Homo sapiens

<400> SEQUENCE: 68

Arg Ala Ser Gln Gly Ile Ser Ser Trp Leu Ala
1               5                   10

<210> SEQ ID NO 69
<211> LENGTH: 7
<212> TYPE: PRT
<213> ORGANISM: Homo sapiens

<400> SEQUENCE: 69

Lys Ala Ser Thr Leu Glu Ser
1               5

<210> SEQ ID NO 70
<211> LENGTH: 9
<212> TYPE: PRT
<213> ORGANISM: Homo sapiens

<400> SEQUENCE: 70

Ala Asn Ile Ala Phe Pro Pro Trp Thr
1               5

<210> SEQ ID NO 71
<211> LENGTH: 375
<212> TYPE: DNA
<213> ORGANISM: Homo sapiens

<400> SEQUENCE: 71
caggtacagc tgcaggagtc aggcccagga ctggtgaagc cttcagagac cctgtccctc      60
acctgcactg tctctggtgg ctccatcagc agtggtggtt actactggag ctggatccgg     120 cagcccccg ggaaggggct ggagtggatt gggagtatct attatagtgg gagcacctac     180
tacaacccgt ccctcaagag tcgagtcacc atatcaggag acacgtccaa gaaccagttc     240
tccctgaagc tgagctctgt gaccgctgcg gacacggccg tatattactg tgcaagaacc     300
cccgcgtatt tcggccagga caggacggat ttctttgacg tctggggcag gggaaccctg     360
gtcaccgtct cctca                                                     375

<210> SEQ ID NO 72
<211> LENGTH: 125
<212> TYPE: PRT
<213> ORGANISM: Homo sapiens

<400> SEQUENCE: 72

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
            115                 120                 125
```

<210> SEQ ID NO 73
<211> LENGTH: 7
<212> TYPE: PRT
<213> ORGANISM: Homo sapiens

<400> SEQUENCE: 73

```
Ser Gly Gly Tyr Tyr Trp Ser
1               5
```

<210> SEQ ID NO 74
<211> LENGTH: 16
<212> TYPE: PRT
<213> ORGANISM: Homo sapiens

<400> SEQUENCE: 74

```
Ser Ile Tyr Tyr Ser Gly Ser Thr Tyr Tyr Asn Pro Ser Leu Lys Ser
1               5                   10                  15
```

<210> SEQ ID NO 75
<211> LENGTH: 15
<212> TYPE: PRT
<213> ORGANISM: Homo sapiens

<400> SEQUENCE: 75

```
Thr Pro Ala Tyr Phe Gly Gln Asp Arg Thr Asp Phe Phe Asp Val
1               5                   10                  15
```

<210> SEQ ID NO 76
<211> LENGTH: 321
<212> TYPE: DNA
<213> ORGANISM: Homo sapiens

<400> SEQUENCE: 76

```
gacatccaga tgacccagtc tccttccacc ctgtctgcat ctgtaggaga cagagtcacc      60
atcacttgcc gggccagtca gggtattagt agctggttgg cctggtatca gcagaaacca     120
gggaaagccc ctaaggtctt gatctataag gcatctactt tagaaagtgg ggtcccatca     180
aggttcagcg gcagtggatc tgggacagaa ttcactctca ccatcagcag tctgcaacct     240
gatgattttg caacttacta ctgtgccaac atcgccttcc ccccgtggac gttcggccaa     300
gggaccaagc tggagatcaa a                                               321
```

<210> SEQ ID NO 77

```
<211> LENGTH: 107
<212> TYPE: PRT
<213> ORGANISM: Homo sapiens

<400> SEQUENCE: 77

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Ala Asn Ile Ala Phe Pro Pro Trp
                85                  90                  95

Thr Phe Gly Gln Gly Thr Lys Leu Glu Ile Lys
            100                 105

<210> SEQ ID NO 78
<211> LENGTH: 11
<212> TYPE: PRT
<213> ORGANISM: Homo sapiens

<400> SEQUENCE: 78

Arg Ala Ser Gln Gly Ile Ser Ser Trp Leu Ala
1               5                   10

<210> SEQ ID NO 79
<211> LENGTH: 7
<212> TYPE: PRT
<213> ORGANISM: Homo sapiens

<400> SEQUENCE: 79

Lys Ala Ser Thr Leu Glu Ser
1               5

<210> SEQ ID NO 80
<211> LENGTH: 9
<212> TYPE: PRT
<213> ORGANISM: Homo sapiens

<400> SEQUENCE: 80

Ala Asn Ile Ala Phe Pro Pro Trp Thr
1               5

<210> SEQ ID NO 81
<211> LENGTH: 375
<212> TYPE: DNA
<213> ORGANISM: Homo sapiens

<400> SEQUENCE: 81
caggtacagc tgcagcagtc aggcccaaga ctggtgaagc cttcacagac cctgtccctc       60
acctgcactg tctctggtgg ctccatcagc agtggtggtt actactggag ctggatccgg      120
cagcccgccg ggaagggget ggagtggatt gggagtatct attatagtgg gagcacctac      180
tacaacccgt ccctcaagag tcgagtcacc atatcaggag acacgcccaa gaaccagttc      240
tccctgaagc tgagctctgt gaccgctgcg gacacggccg tatattactg tgcaagaacc      300
cccgcgtatt tcggccagga caggacggat ttctttgacg tctggggcag gggaaccctg      360
```
gtcaccgtct cctca                                                    375

<210> SEQ ID NO 82
<211> LENGTH: 125
<212> TYPE: PRT
<213> ORGANISM: Homo sapiens

<400> SEQUENCE: 82

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 83
<211> LENGTH: 7
<212> TYPE: PRT
<213> ORGANISM: Homo sapiens

<400> SEQUENCE: 83

Ser Gly Gly Tyr Tyr Trp Ser
1               5

<210> SEQ ID NO 84
<211> LENGTH: 16
<212> TYPE: PRT
<213> ORGANISM: Homo sapiens

<400> SEQUENCE: 84

Ser Ile Tyr Tyr Ser Gly Ser Thr Tyr Tyr Asn Pro Ser Leu Lys Ser
1               5                   10                  15

<210> SEQ ID NO 85
<211> LENGTH: 15
<212> TYPE: PRT
<213> ORGANISM: Homo sapiens

<400> SEQUENCE: 85

Thr Pro Ala Tyr Phe Gly Gln Asp Arg Thr Asp Phe Phe Asp Val
1               5                   10                  15

<210> SEQ ID NO 86
<211> LENGTH: 321
<212> TYPE: DNA
<213> ORGANISM: Homo sapiens

<400> SEQUENCE: 86
gacatcgtga tgacccagtc tccttccacc ctgtctgcat ctgtaggaga cagagtcacc        60
atcacttgcc gggccagtca gggtattagt agctggttgg cctggtatca gcagaaacca      120

```
gggagagccc ctaaggtctt gatctataag gcatctactt tagaaagtgg ggtcccatca    180
aggttcagcg gcagtggatc tgggacagat ttcactctca ccatcagcag tctgcaacct    240
gaagattttg caacttacta ctgtcaacag agtcaccacc cgccgtggac gttcggccaa    300
gggaccaagc tggagatcaa a                                               321
```

```
<210> SEQ ID NO 87
<211> LENGTH: 107
<212> TYPE: PRT
<213> ORGANISM: Homo sapiens

<400> SEQUENCE: 87

Asp Ile Val Met Thr Gln Ser Pro Ser Thr Leu Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Arg Ala Pro Lys Val Leu Ile
        35                  40                  45
Tyr Lys Ala Ser Thr Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser His His Pro Pro Trp
                85                  90                  95
Thr Phe Gly Gln Gly Thr Lys Leu Glu Ile Lys
            100                 105

<210> SEQ ID NO 88
<211> LENGTH: 11
<212> TYPE: PRT
<213> ORGANISM: Homo sapiens

<400> SEQUENCE: 88

Arg Ala Ser Gln Gly Ile Ser Ser Trp Leu Ala
1               5                   10

<210> SEQ ID NO 89
<211> LENGTH: 7
<212> TYPE: PRT
<213> ORGANISM: Homo sapiens

<400> SEQUENCE: 89

Lys Ala Ser Thr Leu Glu Ser
1               5

<210> SEQ ID NO 90
<211> LENGTH: 9
<212> TYPE: PRT
<213> ORGANISM: Homo sapiens

<400> SEQUENCE: 90

Gln Gln Ser His His Pro Pro Trp Thr
1               5

<210> SEQ ID NO 91
<211> LENGTH: 375
<212> TYPE: DNA
<213> ORGANISM: Homo sapiens

<400> SEQUENCE: 91
```

```
caggtgcagc tgcaggagtc aggcccagga ctggtgaagc cttcagagac cctgtccctc    60
acctgcactg tctctggtgg ctccatcagc agtggtggtt actactggag ctggatccgg   120
cagcccccag ggaaggggct ggagtggatt gggagtatct attatagtgg gagcacctac   180
tacaacccgt ccctcaagag tcgagtcacc atatcaggag acacgtccaa gaaccagttc   240
tccctgaagc tgagctctgt gaccgctgcg gacacggccg tatattactg tgcaagaacc   300
cccgcgtatt tcggccagga caggacggat ttctttgacg tctggggcag gggcaccctg   360
gtcaccgtct cctca                                                    375
```

<210> SEQ ID NO 92
<211> LENGTH: 125
<212> TYPE: PRT
<213> ORGANISM: Homo sapiens

<400> SEQUENCE: 92

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 93
<211> LENGTH: 7
<212> TYPE: PRT
<213> ORGANISM: Homo sapiens

<400> SEQUENCE: 93

Ser Gly Gly Tyr Tyr Trp Ser
1               5

<210> SEQ ID NO 94
<211> LENGTH: 16
<212> TYPE: PRT
<213> ORGANISM: Homo sapiens

<400> SEQUENCE: 94

Ser Ile Tyr Tyr Ser Gly Ser Thr Tyr Tyr Asn Pro Ser Leu Lys Ser
1               5                   10                  15

<210> SEQ ID NO 95
<211> LENGTH: 15
<212> TYPE: PRT
<213> ORGANISM: Homo sapiens

<400> SEQUENCE: 95

Thr Pro Ala Tyr Phe Gly Gln Asp Arg Thr Asp Phe Phe Asp Val
1               5                   10                  15

<210> SEQ ID NO 96
<211> LENGTH: 321
<212> TYPE: DNA
<213> ORGANISM: Homo sapiens

<400> SEQUENCE: 96
gacatccaga tgacccagtc tccttccacc ctgtctgcat ctgtaggaga cagagtcacc     60
atcacttgcc gggccagtca gggtattagt agctggttgg cctggtatca gcagaaacca    120
gggaaagccc ctaaggtctt gatctataag gcatctactt tagaaagtgg ggtcccatca    180
aggttcagcg gcagtggatc tgggacagaa ttcactctca ccatcagcag tctgcaacct    240
gatgattttg caacttacta ctgtcaacag agtcaccacc cgccgtggac gttcggccaa    300
gggaccaagc tggagatcaa a                                              321

<210> SEQ ID NO 97
<211> LENGTH: 107
<212> TYPE: PRT
<213> ORGANISM: Homo sapiens

<400> SEQUENCE: 97

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105

<210> SEQ ID NO 98
<211> LENGTH: 11
<212> TYPE: PRT
<213> ORGANISM: Homo sapiens

<400> SEQUENCE: 98

Arg Ala Ser Gln Gly Ile Ser Ser Trp Leu Ala
1               5                   10

<210> SEQ ID NO 99
<211> LENGTH: 7
<212> TYPE: PRT
<213> ORGANISM: Homo sapiens

<400> SEQUENCE: 99

Lys Ala Ser Thr Leu Glu Ser
1               5

<210> SEQ ID NO 100
<211> LENGTH: 9
<212> TYPE: PRT
<213> ORGANISM: Homo sapiens

<400> SEQUENCE: 100

Gln Gln Ser His His Pro Pro Trp Thr
1               5

<210> SEQ ID NO 101
<211> LENGTH: 375
<212> TYPE: DNA
<213> ORGANISM: Homo sapiens

<400> SEQUENCE: 101
caggtgcagc tgcaggagtc aggcccagga ctggtgaagc cttcagagac cctgtccctc      60
acctgcactg tctctggtgg ctccatcagc gctggtggtt actactggag ctggatccgg     120 cagcccccg ggaaggggct ggagtggatt gggagtctct attatagtgg gagcacctac      180
tacaacccgt ccctcaaggg tcgagtcacc atatcaggag acacgtccaa gaaccagttc     240
tccctgaagc tgagctctgt gaccgctgcg gacacggccg tatattactg tgcaagaacc     300
cccgcgtatt tcggccagga caggacggat ttctttgacg tctggggcag gggcaccctg     360
gtcaccgtct cctca                                                       375

<210> SEQ ID NO 102
<211> LENGTH: 125
<212> TYPE: PRT
<213> ORGANISM: Homo sapiens

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Gly
            20                  25                  30

Gly Tyr Tyr Trp Ser Trp Ile Arg Gln Pro Pro Gly Lys Gly Leu Glu
        35                  40                  45

Trp Ile Gly Ser Leu Tyr Tyr Ser Gly Ser Thr Tyr Tyr Asn Pro Ser
    50                  55                  60

Leu Lys Gly Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 103
<211> LENGTH: 7
<212> TYPE: PRT
<213> ORGANISM: Homo sapiens

<400> SEQUENCE: 103

Ala Gly Gly Tyr Tyr Trp Ser
1               5

<210> SEQ ID NO 104
<211> LENGTH: 16
<212> TYPE: PRT
<213> ORGANISM: Homo sapiens

<400> SEQUENCE: 104

Ser Leu Tyr Tyr Ser Gly Ser Thr Tyr Tyr Asn Pro Ser Leu Lys Gly
1               5                   10                  15

<210> SEQ ID NO 105
<211> LENGTH: 15
<212> TYPE: PRT
<213> ORGANISM: Homo sapiens

<400> SEQUENCE: 105

Thr Pro Ala Tyr Phe Gly Gln Asp Arg Thr Asp Phe Phe Asp Val
1               5                   10                  15

<210> SEQ ID NO 106
<211> LENGTH: 321
<212> TYPE: DNA
<213> ORGANISM: Homo sapiens

<400> SEQUENCE: 106
gacatccaga tgacccagtc tccttccacc ctgtctgcat ctgtaggaga cagagtcacc      60
atcacttgcc gggccagtca gggtattagt agctggttgg cctggtatca gcagaaacca     120
gggaaagccc ctaaggtctt gatctataag gcatctactt tagaaagtgg ggtcccatca     180
aggttcagcg gcagtggatc tgggacagaa ttcactctca ccatcagcag tctgcaacct     240
gatgattttg caacttacta ctgtcaacag agtcaccacc cgccgtggac gttcggccaa     300
gggaccaagc tggagatcaa a                                               321

<210> SEQ ID NO 107
<211> LENGTH: 107
<212> TYPE: PRT
<213> ORGANISM: Homo sapiens

<400> SEQUENCE: 107

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105

<210> SEQ ID NO 108
<211> LENGTH: 11
<212> TYPE: PRT
<213> ORGANISM: Homo sapiens

<400> SEQUENCE: 108

Arg Ala Ser Gln Gly Ile Ser Ser Trp Leu Ala
1               5                   10

<210> SEQ ID NO 109
<211> LENGTH: 7
<212> TYPE: PRT
<213> ORGANISM: Homo sapiens

<400> SEQUENCE: 109

Lys Ala Ser Thr Leu Glu Ser
1               5

<210> SEQ ID NO 110
<211> LENGTH: 9
<212> TYPE: PRT
<213> ORGANISM: Homo sapiens

<400> SEQUENCE: 110

Gln Gln Ser His His Pro Pro Trp Thr
1               5

<210> SEQ ID NO 111
<211> LENGTH: 375
<212> TYPE: DNA
<213> ORGANISM: Homo sapiens

<400> SEQUENCE: 111

```
caggtacagc tgcagcagtc aggcccaaga ctggtggagc cttcacagac cctgtccctc      60
acctgcactg tctccggtgg ctccatcagc agtgatggtt actactggag ctggatccgg     120
cagcccgccg ggaaggggct ggagtggatt gggagtatct attatagtgg gagcacctac     180
tacaacccgt ccctcaagag tcgagtcacc atatcaggag acacgcccaa gaaccagttc     240
tccctgaagc tgagctctgt gaccgctgcg gacacggccg tatattactg tgcaaggacc     300
cccgcgtatt tcggccagga caggacggat ttctttgacg tctggggcag gggaaccctg     360
gtcaccgtct cctca                                                      375
```

<210> SEQ ID NO 112
<211> LENGTH: 125
<212> TYPE: PRT
<213> ORGANISM: Homo sapiens

<400> SEQUENCE: 112

Gln Val Gln Leu Gln Gln Ser Gly Pro Arg Leu Val Glu Pro Ser Gln
1               5                   10                  15

Thr Leu Ser Leu Thr Cys Thr Val Ser Gly Gly Ser Ile Ser Ser Asp
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 113
<211> LENGTH: 7
<212> TYPE: PRT
<213> ORGANISM: Homo sapiens

<400> SEQUENCE: 113

Ser Asp Gly Tyr Tyr Trp Ser
1               5

<210> SEQ ID NO 114
<211> LENGTH: 16
<212> TYPE: PRT
<213> ORGANISM: Homo sapiens

<400> SEQUENCE: 114

Ser Ile Tyr Tyr Ser Gly Ser Thr Tyr Tyr Asn Pro Ser Leu Lys Ser
1               5                   10                  15

<210> SEQ ID NO 115
<211> LENGTH: 15
<212> TYPE: PRT
<213> ORGANISM: Homo sapiens

<400> SEQUENCE: 115

Thr Pro Ala Tyr Phe Gly Gln Asp Arg Thr Asp Phe Phe Asp Val
1               5                   10                  15

<210> SEQ ID NO 116
<211> LENGTH: 321
<212> TYPE: DNA
<213> ORGANISM: Homo sapiens

<400> SEQUENCE: 116
gacatcgtga tgacccagtc tccttccacc ctgtctgcat ctgtaggaga cagagtcacc      60
atcacttgcc gggccagtca gggtattagt agctggttgg cctggtatca gcagaaacca    120
gggagagccc ctaaggtctt gatctataag gcgtctactt tagaaagtgg ggtcccatca    180
aggttcagcg gcagtggatc tgggacagat ttcactctca caatcagcag tctgcaacct    240
gaagattttg caacttacta ctgtcaacag agtcaccacc cgccgtggac gttcggccaa    300
gggaccaagc tggagatcaa a                                              321

<210> SEQ ID NO 117
<211> LENGTH: 107
<212> TYPE: PRT
<213> ORGANISM: Homo sapiens

<400> SEQUENCE: 117

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Arg Ala Pro Lys Val Leu Ile
            35                  40                  45

Tyr Lys Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Pro Trp
                85                  90                  95

Thr Phe Gly Gln Gly Thr Lys Leu Glu Ile Lys
                100                 105

<210> SEQ ID NO 118
<211> LENGTH: 11
<212> TYPE: PRT
<213> ORGANISM: Homo sapiens

<400> SEQUENCE: 118

<210> SEQ ID NO 119
<211> LENGTH: 7
<212> TYPE: PRT
<213> ORGANISM: Homo sapiens

<400> SEQUENCE: 119

Lys Ala Ser Thr Leu Glu Ser
1               5

<210> SEQ ID NO 120
<211> LENGTH: 9
<212> TYPE: PRT
<213> ORGANISM: Homo sapiens

<400> SEQUENCE: 120

Gln Gln Ser His His Pro Pro Trp Thr
1               5

<210> SEQ ID NO 121
<211> LENGTH: 375
<212> TYPE: DNA
<213> ORGANISM: Homo sapiens

<400> SEQUENCE: 121

```
caggtacagc tgcagcagtc aggcccaaga ctggtggagc cttcacagac cctgtccctc      60
acctgcactg tctctggtgg ctccatcagc agtgatggtt actactggag ctggatccgg     120
cagcccgccg ggaaggggct ggagtggatt gggagtatct attatagtgg gagcacctac     180
tacaacccgt ccctcaggag tcgagtcacc atatcaggag acacgcccaa gaaccagttc     240
tccctgaagc tgagctctgt gaccgctgcg gacacggccg tatattactg tgcaagaacc     300
cccgcgtatt tcggccagga caggacggat ttctttgacg tctggggcag ggaaccctg      360 gtcaccgtct cctca                                                     375
```

<210> SEQ ID NO 122
<211> LENGTH: 125
<212> TYPE: PRT
<213> ORGANISM: Homo sapiens

<400> SEQUENCE: 122

Gln Val Gln Leu Gln Gln Ser Gly Pro Arg Leu Val Glu Pro Ser Gln
1               5                   10                  15

Thr Leu Ser Leu Thr Cys Thr Val Ser Gly Gly Ser Ile Ser Ser Asp
                20                  25                  30

Gly Tyr Tyr Trp Ser Trp Ile Arg Gln Pro Ala Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Arg Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 123
<211> LENGTH: 7
<212> TYPE: PRT
<213> ORGANISM: Homo sapiens

<400> SEQUENCE: 123

Ser Asp Gly Tyr Tyr Trp Ser
1               5

<210> SEQ ID NO 124
<211> LENGTH: 16
<212> TYPE: PRT
<213> ORGANISM: Homo sapiens

<400> SEQUENCE: 124

Ser Ile Tyr Tyr Ser Gly Ser Thr Tyr Tyr Asn Pro Ser Leu Arg Ser
1               5                   10                  15

<210> SEQ ID NO 125
<211> LENGTH: 15
<212> TYPE: PRT
<213> ORGANISM: Homo sapiens

<400> SEQUENCE: 125

Thr Pro Ala Tyr Phe Gly Gln Asp Arg Thr Asp Phe Phe Asp Val
1               5                   10                  15

<210> SEQ ID NO 126
<211> LENGTH: 321
<212> TYPE: DNA
<213> ORGANISM: Homo sapiens

<400> SEQUENCE: 126

```
gacatcgtga tgacccagtc tccttccacc ctgtctgcat ctgtaggaga cagggtcacc      60
atcacttgcc gggccagtca gggtattagt agctggttgg cctggtatca gcagaaacca     120
gggggagccc ctaaggtctt gatctataag gcgtctactt tagaaagtgg ggtcccatca     180
aggttcagcg gcagtggatc tgggacagat ttcactctca ccatcagcag tctgcagcct     240
gaagattttg caacttacta ctgtcaacag agtcaccacc cgccgtggac gttcagccaa     300
gggaccaagc tggagatcaa a                                                321
```

<210> SEQ ID NO 127
<211> LENGTH: 107
<212> TYPE: PRT
<213> ORGANISM: Homo sapiens

<400> SEQUENCE: 127

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Gly Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Pro Trp
                85                  90                  95

Thr Phe Ser Gln Gly Thr Lys Leu Glu Ile Lys
            100                 105

<210> SEQ ID NO 128
<211> LENGTH: 11
<212> TYPE: PRT
<213> ORGANISM: Homo sapiens

<400> SEQUENCE: 128

Arg Ala Ser Gln Gly Ile Ser Ser Trp Leu Ala
1               5                   10

<210> SEQ ID NO 129
<211> LENGTH: 7
<212> TYPE: PRT
<213> ORGANISM: Homo sapiens

<400> SEQUENCE: 129

Lys Ala Ser Thr Leu Glu Ser
1               5

<210> SEQ ID NO 130
<211> LENGTH: 9
<212> TYPE: PRT
<213> ORGANISM: Homo sapiens

<400> SEQUENCE: 130

Gln Gln Ser His His Pro Pro Trp Thr
1               5

<210> SEQ ID NO 131
<211> LENGTH: 375
<212> TYPE: DNA
<213> ORGANISM: Homo sapiens

<400> SEQUENCE: 131
caggtacagc tgcagcagtc aggcccaaga ctggtggagc cttcacagac cctgtccctc      60
acctgcactg tctctggtgg ctccatcagc gctgatggtt actactggag ctggatccgg     120
cagcccgccg ggaaggggct ggagtggatt gggagtctct attatagtgg gagcacctac     180
tacaacccgt ccctcagggg tcgagtcacc atatcaggag acacgcccaa gaaccagttc     240
tccctgaagc tgagctctgt gaccgctgcg gacacggccg tatattactg tgcaagaacc     300
cccgcgtatt tcggccagga caggacggat ttctttgacg tctggggcag gggaaccctg     360
gtcaccgtct cctca                                                      375

<210> SEQ ID NO 132
<211> LENGTH: 125
<212> TYPE: PRT
<213> ORGANISM: Homo sapiens

<400> SEQUENCE: 132

Gln Val Gln Leu Gln Gln Ser Gly Pro Arg Leu Val Glu Pro Ser Gln
1               5                   10                  15

Thr Leu Ser Leu Thr Cys Thr Val Ser Gly Gly Ser Ile Ser Ala Asp
            20                  25                  30

Gly Tyr Tyr Trp Ser Trp Ile Arg Gln Pro Ala Gly Lys Gly Leu Glu
        35                  40                  45

Trp Ile Gly Ser Leu Tyr Tyr Ser Gly Ser Thr Tyr Tyr Asn Pro Ser
    50                  55                  60

Leu Arg Gly Arg Val Thr Ile Ser Gly Asp Thr Pro Lys Asn Gln Phe

```
                65                  70                  75                  80
Ser Leu Lys Leu Ser Ser Val Thr Ala Ala Asp Thr Ala Val Tyr Tyr
                    85                  90                  95

Cys Ala Arg Thr Pro Ala Tyr Phe Gly Gln Asp Arg Thr Asp Phe Phe
                100                 105                 110

Asp Val Trp Gly Arg Gly Thr Leu Val Thr Val Ser Ser
                115                 120                 125

<210> SEQ ID NO 133
<211> LENGTH: 7
<212> TYPE: PRT
<213> ORGANISM: Homo sapiens

<400> SEQUENCE: 133

Ala Asp Gly Tyr Tyr Trp Ser
1               5

<210> SEQ ID NO 134
<211> LENGTH: 16
<212> TYPE: PRT
<213> ORGANISM: Homo sapiens

<400> SEQUENCE: 134

Ser Leu Tyr Tyr Ser Gly Ser Thr Tyr Tyr Asn Pro Ser Leu Arg Gly
1               5                   10                  15

<210> SEQ ID NO 135
<211> LENGTH: 15
<212> TYPE: PRT
<213> ORGANISM: Homo sapiens

<400> SEQUENCE: 135

Thr Pro Ala Tyr Phe Gly Gln Asp Arg Thr Asp Phe Phe Asp Val
1               5                   10                  15

<210> SEQ ID NO 136
<211> LENGTH: 321
<212> TYPE: DNA
<213> ORGANISM: Homo sapiens

<400> SEQUENCE: 136
gacatcgtga tgacccagtc tccttccacc ctgtctgcat ctgtaggaga cagggtcacc      60
atcacttgcc gggccagtca gggtattagt agctggttgg cctggtatca gcagaaacca     120
gggggagccc ctaaggtctt gatctataag gcgtctactt tagaaagtgg ggtcccatca     180
aggttcagcg gcagtggatc tgggacagat ttcactctca ccatcagcag tctgcagcct     240
gaagattttg caacttacta ctgtcaacag agtcaccacc gccgtggac gttcagccaa     300 gggaccaagc tggagatcaa a                                               321

<210> SEQ ID NO 137
<211> LENGTH: 107
<212> TYPE: PRT
<213> ORGANISM: Homo sapiens

<400> SEQUENCE: 137

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Gly Ala Pro Lys Val Leu Ile
```

```
                     35                  40                  45
Tyr Lys Ala Ser Thr Leu Glu Ser Gly Val Pro Ser Arg Phe Ser Gly
             50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Pro Trp
                    85                  90                  95

Thr Phe Ser Gln Gly Thr Lys Leu Glu Ile Lys
            100                 105
```

<210> SEQ ID NO 138
<211> LENGTH: 11
<212> TYPE: PRT
<213> ORGANISM: Homo sapiens

<400> SEQUENCE: 138

```
Arg Ala Ser Gln Gly Ile Ser Ser Trp Leu Ala
1               5                   10
```

<210> SEQ ID NO 139
<211> LENGTH: 7
<212> TYPE: PRT
<213> ORGANISM: Homo sapiens

<400> SEQUENCE: 139

```
Lys Ala Ser Thr Leu Glu Ser
1               5
```

<210> SEQ ID NO 140
<211> LENGTH: 9
<212> TYPE: PRT
<213> ORGANISM: Homo sapiens

<400> SEQUENCE: 140

```
Gln Gln Ser His His Pro Pro Trp Thr
1               5
```

<210> SEQ ID NO 141
<211> LENGTH: 375
<212> TYPE: DNA
<213> ORGANISM: Homo sapiens

<400> SEQUENCE: 141

```
caggtacagc tgcaggagtc aggcccagga ctggtgaagc cttcagagac cctgtccctc      60
acctgcactg tctctggtgg ctccatcagc gctgatggtt actactggag ctggatccgg     120
cagcccccg ggaagggct ggagtggatt gggagtctct attatagtgg gagcacctac       180
tacaacccgt ccctcagggg tcgagtcacc atatcaggag acacgtccaa gaaccagttc     240
tccctgaagc tgagctctgt gaccgctgcg gacacggccg tatattactg tgcaagaacc     300
cccgcgtatt tcggccagga caggacggat ttctttgacg tctggggcag gggaaccctg     360
gtcaccgtct cctca                                                     375
```

<210> SEQ ID NO 142
<211> LENGTH: 125
<212> TYPE: PRT
<213> ORGANISM: Homo sapiens

<400> SEQUENCE: 142

```
Gln Val Gln Leu Gln Glu Ser Gly Pro Gly Leu Val Lys Pro Ser Glu
1               5                   10                  15
```

Thr Leu Ser Leu Thr Cys Thr Val Ser Gly Gly Ser Ile Ser Ala Asp
            20                  25                  30

Gly Tyr Tyr Trp Ser Trp Ile Arg Gln Pro Pro Gly Lys Gly Leu Glu
        35                  40                  45

Trp Ile Gly Ser Leu Tyr Tyr Ser Gly Ser Thr Tyr Tyr Asn Pro Ser
 50                  55                  60

Leu Arg Gly Arg Val Thr Ile Ser Gly Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
            115                 120                 125

<210> SEQ ID NO 143
<211> LENGTH: 7
<212> TYPE: PRT
<213> ORGANISM: Homo sapiens

<400> SEQUENCE: 143

Ala Asp Gly Tyr Tyr Trp Ser
1               5

<210> SEQ ID NO 144
<211> LENGTH: 16
<212> TYPE: PRT
<213> ORGANISM: Homo sapiens

<400> SEQUENCE: 144

Ser Leu Tyr Tyr Ser Gly Ser Thr Tyr Tyr Asn Pro Ser Leu Arg Gly
1               5                   10                  15

<210> SEQ ID NO 145
<211> LENGTH: 15
<212> TYPE: PRT
<213> ORGANISM: Homo sapiens

<400> SEQUENCE: 145

Thr Pro Ala Tyr Phe Gly Gln Asp Arg Thr Asp Phe Phe Asp Val
1               5                   10                  15

<210> SEQ ID NO 146
<211> LENGTH: 321
<212> TYPE: DNA
<213> ORGANISM: Homo sapiens

<400> SEQUENCE: 146
gacatccaga tgacccagtc tccttccacc ctgtctgcat ctgtaggaga cagagtcacc    60
atcacttgcc gggccagtca gggtattagt agctggttgg cctggtatca gcagaaacca   120
gggaaagccc ctaaggtctt gatctataag gcatctactt tagaaagtgg ggtcccatca   180
aggttcagcg gcagtggatc tgggacagaa ttcactctca ccatcagcag tctgcaacct   240
gatgattttg caacttacta ctgtcaacag agtcaccacc gccgtggac gttcggccaa   300 gggaccaagc tggagatcaa a                                             321

<210> SEQ ID NO 147
<211> LENGTH: 107
<212> TYPE: PRT

<213> ORGANISM: Homo sapiens

<400> SEQUENCE: 147

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105

<210> SEQ ID NO 148
<211> LENGTH: 11
<212> TYPE: PRT
<213> ORGANISM: Homo sapiens

<400> SEQUENCE: 148

Arg Ala Ser Gln Gly Ile Ser Ser Trp Leu Ala
1               5                   10

<210> SEQ ID NO 149
<211> LENGTH: 7
<212> TYPE: PRT
<213> ORGANISM: Homo sapiens

<400> SEQUENCE: 149

Lys Ala Ser Thr Leu Glu Ser
1               5

<210> SEQ ID NO 150
<211> LENGTH: 9
<212> TYPE: PRT
<213> ORGANISM: Homo sapiens

<400> SEQUENCE: 150

Gln Gln Ser His His Pro Pro Trp Thr
1               5

<210> SEQ ID NO 151
<211> LENGTH: 375
<212> TYPE: DNA
<213> ORGANISM: Homo sapiens

<400> SEQUENCE: 151
caggtacagc tgcaggagtc aggcccagga ctggtgaagc cttcagagac cctgtccctc      60
acctgcactg tctctggtgg ctccatcagc gctgatggtt actactggag ctggatccgg     120 cagcccccg ggaaggggct ggagtggatt gggagtctct attatagtgg gagcacctac      180
tacaacccgt ccctcaaggg tcgagtcacc atatcaggag acacgtccaa gaaccagttc    240
tccctgaagc tgagctctgt gaccgctgcg gacacggccg tatattactg tgcaagaacc    300
cccgcgtatt tcggccagga caggacggat ttctttgacg tctggggcag gggaaccctg    360
gtcaccgtct cctca                                                      375

<210> SEQ ID NO 152
<211> LENGTH: 125
<212> TYPE: PRT
<213> ORGANISM: Homo sapiens

<400> SEQUENCE: 152

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Asp
            20                  25                  30

Gly Tyr Tyr Trp Ser Trp Ile Arg Gln Pro Pro Gly Lys Gly Leu Glu
        35                  40                  45

Trp Ile Gly Ser Leu Tyr Tyr Ser Gly Ser Thr Tyr Tyr Asn Pro Ser
    50                  55                  60

Leu Lys Gly Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 153
<211> LENGTH: 7
<212> TYPE: PRT
<213> ORGANISM: Homo sapiens

<400> SEQUENCE: 153

Ala Asp Gly Tyr Tyr Trp Ser
1               5

<210> SEQ ID NO 154
<211> LENGTH: 16
<212> TYPE: PRT
<213> ORGANISM: Homo sapiens

<400> SEQUENCE: 154

Ser Leu Tyr Tyr Ser Gly Ser Thr Tyr Tyr Asn Pro Ser Leu Lys Gly
1               5                   10                  15

<210> SEQ ID NO 155
<211> LENGTH: 15
<212> TYPE: PRT
<213> ORGANISM: Homo sapiens

<400> SEQUENCE: 155

Thr Pro Ala Tyr Phe Gly Gln Asp Arg Thr Asp Phe Phe Asp Val
1               5                   10                  15

<210> SEQ ID NO 156
<211> LENGTH: 321
<212> TYPE: DNA
<213> ORGANISM: Homo sapiens

<400> SEQUENCE: 156
gacatccaga tgacccagtc tccttccacc ctgtctgcat ctgtaggaga cagagtcacc    60
atcacttgcc gggccagtca gggtattagt agctggttgg cctggtatca gcagaaacca   120
gggaaagccc ctaaggtctt gatctataag gcatctactt tagaaagtgg ggtcccatca   180

```
aggttcagcg gcagtggatc tgggacagaa ttcactctca ccatcagcag tctgcaacct      240
gatgattttg caacttacta ctgtcaacag agtcaccacc cgccgtggac gttcggccaa      300
gggaccaagc tggagatcaa a                                                321
```

<210> SEQ ID NO 157
<211> LENGTH: 107
<212> TYPE: PRT
<213> ORGANISM: Homo sapiens

<400> SEQUENCE: 157

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105
```

<210> SEQ ID NO 158
<211> LENGTH: 11
<212> TYPE: PRT
<213> ORGANISM: Homo sapiens

<400> SEQUENCE: 158

```
Arg Ala Ser Gln Gly Ile Ser Ser Trp Leu Ala
1               5                   10
```

<210> SEQ ID NO 159
<211> LENGTH: 7
<212> TYPE: PRT
<213> ORGANISM: Homo sapiens

<400> SEQUENCE: 159

```
Lys Ala Ser Thr Leu Glu Ser
1               5
```

<210> SEQ ID NO 160
<211> LENGTH: 9
<212> TYPE: PRT
<213> ORGANISM: Homo sapiens

<400> SEQUENCE: 160

```
Gln Gln Ser His His Pro Pro Trp Thr
1               5
```

<210> SEQ ID NO 161
<211> LENGTH: 30
<212> TYPE: PRT
<213> ORGANISM: Homo sapiens

<400> SEQUENCE: 161

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser
        20                  25                  30
```

<210> SEQ ID NO 162
<211> LENGTH: 14
<212> TYPE: PRT
<213> ORGANISM: Homo sapiens

<400> SEQUENCE: 162

```
Trp Ile Arg Gln Pro Pro Gly Lys Gly Leu Glu Trp Ile Gly
1               5                   10
```

<210> SEQ ID NO 163
<211> LENGTH: 32
<212> TYPE: PRT
<213> ORGANISM: Homo sapiens

<400> SEQUENCE: 163

```
Arg Val Thr Ile Ser Gly Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 164
<211> LENGTH: 11
<212> TYPE: PRT
<213> ORGANISM: Homo sapiens

<400> SEQUENCE: 164

```
Trp Gly Arg Gly Thr Leu Val Thr Val Ser Ser
1               5                   10
```

<210> SEQ ID NO 165
<211> LENGTH: 23
<212> TYPE: PRT
<213> ORGANISM: Homo sapiens

<400> SEQUENCE: 165

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 166
<211> LENGTH: 15
<212> TYPE: PRT
<213> ORGANISM: Homo sapiens

<400> SEQUENCE: 166

```
Trp Tyr Gln Gln Lys Pro Gly Lys Ala Pro Lys Val Leu Ile Tyr
1               5                   10                  15
```

<210> SEQ ID NO 167
<211> LENGTH: 32
<212> TYPE: PRT
<213> ORGANISM: Homo sapiens

<400> SEQUENCE: 167

```
Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30
```

<210> SEQ ID NO 168
<211> LENGTH: 10
<212> TYPE: PRT
<213> ORGANISM: Homo sapiens

<400> SEQUENCE: 168

Phe Gly Gln Gly Thr Lys Leu Glu Ile Lys
1               5                   10

<210> SEQ ID NO 169
<211> LENGTH: 157
<212> TYPE: PRT
<213> ORGANISM: Homo sapiens

<400> SEQUENCE: 169

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 170
<211> LENGTH: 375
<212> TYPE: DNA
<213> ORGANISM: Homo sapiens

<400> SEQUENCE: 170
caggtacagc tgcaggagtc cggccctggc ctggtgaagc cttccgagac actgtccctg      60
acctgcaccg tgtccggcgg ctccatctcc gccgacggct actactggtc ctggatcagg     120
cagcctcctg caagggcct ggagtggatc ggctccctgt actactccgg ctccacctac      180 tacaacccctt ccctgaaggg cagagtgacc atctccggcg acacctccaa gaaccagttc    240
tccctgaagc tgtcctccgt gaccgccgct gacaccgccg tgtactactg cgcccggacc     300
cctgcctact tcggacagga ccggaccgac ttcttcgacg tgtggggcag gggaaccctg     360
gtcaccgtct cctca                                                      375

<210> SEQ ID NO 171
<211> LENGTH: 321
<212> TYPE: DNA
<213> ORGANISM: Homo sapiens

```
<400> SEQUENCE: 171
gacatccaga tgacccagtc cccctccacc ctgtccgcct ccgtgggcga cagagtgacc        60
atcacctgcc gggcctccca gggcatctcc tcttggctgg cctggtatca gcagaagcct       120
ggcaaggccc ctaaggtgct gatctacaag gcctctaccc tggagtccgg cgtgccttcc       180
cggttctccg gctccggctc tggcaccgag ttcaccctga ccatctccag cctgcagcct       240
gacgacttcg ccacctacta ctgccagcag tcccaccacc ctccctggac cttcggccag       300
ggcaccaagc tggagatcaa g                                                 321
```

ANTI-IL-18 ANTIBODIES AND THEIR USES

CROSS-REFERENCE TO RELATED APPLICATIONS

This application is a U.S. National Stage application of International Application No. PCT/EP2011/073496, filed on Dec. 20, 2011, said International Application No. PCT/EP2011/073496 claims benefit under 35 U.S.C. §119(E) of the U.S. Provisional Application No. 61/424,920 filed Dec. 20, 2010. Each of the above listed applications is incorporated by reference herein in its entirety for all purposes.

REFERENCE TO THE SEQUENCE LISTING

This application contains a Sequence Listing which has been submitted in ASCII format via EFS-Web and is hereby incorporated by reference in its entirety. Said ASCII copy, created on Aug. 2, 2013, is named IL18-1000S1 SL.txt and is 72,103 bytes in size.

FIELD OF THE INVENTION

The present invention relates to antibody molecules that bind interleukin 18 (IL-18) and inhibit its biological effects. Anti-IL-18 antibodies may be useful for example, in diagnosing and treating disorders associated with elevated IL-18 levels, including inflammatory, cardiovascular and autoimmune diseases.

BACKGROUND OF THE INVENTION

Interleukin-18 (IL-18) is a potent cytokine that plays a role in both innate and acquired immune responses. IL-18 was first identified for its ability to induce the production of IFN-γ, one of the primary effector molecules of a T helper (Th) 1-type immune response (Okamura et al (1995) Nature 378: 88-91). It was shown subsequently that, in certain settings, IL-18 can also contribute to the development of additional responses such as Th2 (Nakanishi et al (2001) Annu Rev Immunol. 19:423-74). In addition to its stimulatory effect on cluster of differentiation (CD) 4+ and CD8+ T cells, IL-18 has been shown to have a broad spectrum of inflammation-related effects on various cells types including neutrophils, monocytes/macrophages, natural killer (NK) cells, epithelial and endothelial cells.

IL-18 belongs to the interleukin-1 (IL-1) superfamily, and like IL-1 beta (IL-1β) it is first synthesised as an inactive intracellular polypeptide, pro-IL-18 (24 kDa). Enzymatic cleavage of the pro-peptide releases the biologically active mature form of IL-18 (18 kDa). IL-18 is produced by macrophages and other cells involved in the immune response. Apart from its physiological role, IL-18 also contributes to severe inflammatory reactions, providing indication of its role in certain inflammatory disorders such as autoimmune diseases. IL-18 is regulated in part by endogenous IL-18 binding protein (IL-18BP) which binds to IL-18 and blocks its binding to the IL-18 receptor (IL-18R), thereby quenching the IL-18 activity. However, in certain circumstances, this negative feedback loop is insufficient to adequately quench the biological effects of IL-18 whilst still providing enough IL-18 biological activity to initiate innate immune responses.

The biological activity of IL-18 is generated when IL-18 binds to cell-bound IL-18R, initiating cell signaling which leads to expression of other cytokines. The IL-18R is a heterodimer comprising two IgG like polypeptide chains that form a functional complex in which the β chain contains the IL-18 binding motif and the α chain contains an intracellular signalling domain (TIR) (Torigoe et al (1997) J Biol Chem 272:25737). IL-18 appears to first bind IL-18Rα and the β chain is then recruited to form the functional heterodimer. The binding of IL-18 to the α/β complex results in activation of the intracellular signalling cascade. Thus, blocking the binding of IL-18 to IL-18Rα may be useful in quenching unwanted IL-18.

IL-18 has been implicated in a number of human diseases, primarily autoimmune or inflammatory diseases and cancer. Psoriasis patients have increased IL-18 both in the skin lesions and in the circulation (Flisiak et al. (2006) 11:194). Elevated plasma IL-18 levels have been observed in cerebrospinal fluid and plasma of patients with multiple sclerosis (Fassbender et al. (1999) Neurology 53:1104; Nicoletti et al. (2001) Neurology 57:342). Patients with inflammatory bowel diseases (e.g. Crohn's disease, ulcerative colitis) have elevated IL-18 levels in the circulation (Ludwiczek et al (2005) Eur. Cytokine Netw. 16:27; Wiercinska-Drapalo et al (2005) World J Gastroenterol. 11:605). Patients with rheumatoid arthritis (RA) have elevated IL-18 levels in the synovial fluid (Gracie et al (1999) J Clin Invest 104:1393). IL-18 has also been shown to be increased in the serum of patients with other arthritic diseases with systemic manifestations such as Still's disease (Kawashima et al (2001) Arthritis Rheum. 44(3):550-60) and systemic juvenile idyopathic arthritis (sJIA) (Maeno et al (2002) Arthritis Rheum. 46(9):2539-41; Shimizu et al (2010) Rheumatology 49(9):1645-53) and has been proposed as a marker of disease severity (Kawagushi et al (2001) Arthritis Rheum. 44(7):1716-7; Lotito et al (2007) J Rheumatol. 34(4):823-30). In these autoinflammatory disorders, circulating IL-18 was shown to be further increased during the active phase of the disease and in a subset of patients developing complications such as macrophage activation syndrome (Shimizu et al (2010) Rheumatology 49(9): 1645-53). IL-18 levels were also shown to be increased both systemically and in the pulmonary tissues of Chronic Obstructive Pulmonary Disease (COPD) patients, where IL-18 is associated with alveolar macrophages, CD8+ T cells and airway epithelial cells (Imaoka et al (2009) Eur Respir J. 31:287-97; Kang et al. (2007) J. Immunol. 178(3):1948-59; Petersen et al. (2007) Lung 185:161-71; Rovina et al (2009) Respir Med. 103:1056-62). IL-18 may also contribute to COPD co-morbidities (Petersen et al (2007) Lung 185:161; Larsen et al (2008) Cardiovasc Res 80:47).

In cardiovascular diseases, elevated plasma or serum levels of circulatory IL-18 were measured in acute coronary syndrome, myocardial infarction, coronary atherosclerosis, and unstable angina (Mallat et al (2002) Heart 88:467; Hulthe et al (2006) Atherosclerosis 188:450; Mallat et al (2001) Circulation 104:1598). Serum IL-18 levels are also associated with intima-media thickness of the carotid arteries (Yamagami et al (2004) Arterioscler Thromb Vasc Biol 25:1458).

Several types of cancers are also associated with elevated IL-18 expression levels. However the role of IL-18 may be dual in malignant diseases (Dinarello (2008) Cancer & Metastasis Rev 25:307). On one hand, IL-18 may be pro-angiogenic and thereby may promote tumor development, on the other hand it may stimulate cellular immune responses, e.g. NK cell mediated cytotoxicity and thereby act as an anti-tumorigenic agent (Kim et al. (2007) Oncogene 26:1468.).

Many of these clinical observations have also been corroborated in animal models of human disease. These studies have addressed both disease mechanisms dependent on IL-18 and IL-18 as a potential target for intervention. Development of CNS lesions in experimental autoimmune encephalitis (EAE), the most widely used animal model for multiple sclerosis, was shown to be dependent on IL-18Rα engagement (Gutcher et al. (2006) Nat Immunol 7:946.). The administration of IL-18 to animals was shown to enhance disease in the collagen induced arthritis model of RA (Gracie et al. (1999) J Clin Invest 104:1393), while lack of IL-18 or IL-18 neutralising therapies attenuated the severity of the disease (Banda et al. (2003) J Immunol 170:2100). IL-18 knockout mice are resistant to experimentally induced colitis (Hovet et al (2001) Gastroenterol 121:1372), whereas transgenic animals over-expressing IL-18 are more susceptible (Ishikura et al. (2003) J Gastroenterol Hepatol 18:960). IL-18 neutralising treatment attenuates intestinal inflammation (Lochner and Foster (2002) Pathobiol 70:164).

In an animal model developed for COPD, cigarette smoke was shown to increase IL-18 expression locally in the lung tissue (Kang et al (2008) Clin Invest 118:2771, Kang et al (2007) J Immunol 178:1948). In this model, impairment of IL-18 signaling via disruption of IL-18Rα gene resulted in a decreased lung inflammation, cell apoptosis and emphysema (Kang et al (2007) J Immunol 178:1948). Conversely, overexpression of IL-18 in the lung of mice was associated with pulmonary inflammation characterized by the recruitment of CD8+ T cells, macrophages, neutrophils and eosinophils as well as lung with an emphysematous phenotype (Hoshino et al (2007) Am J Respir Crit Care Med 176:49). In addition to chronic lung inflammation, IL-18 may be associated with virally or bacterially-triggered exacerbations. In a cigarette smoke mouse model, IL-18 levels were shown to be further enhanced by treatment of mice with poly(I:C) or infection with influenza and to contribute to the inflammation, alveolar remodeling and apoptosis (Kang et al (2008) supra).

A number of experimental animal models have addressed the role of IL-18 in cardiovascular diseases, especially the development of atherosclerosis. Administering recombinant IL-18 to ApoE−/− mice resulted in increased atherosclerotic lesion size and elevated plasma IFNγ levels (Tenger et al. (2005) Arterioscler Thromb Vasc Biol 25: 791). Overexpressing the naturally occurring IL-18 inhibitor, IL-18BP, in ApoE−/− mice resulted in reduced atherosclerosis and major changes in plaque phenotype, indicating more "stable" lesions (Mallat et al. (2001) Circ Res 89:E41). The phenotype of the double knockout ApoE−/− x IL-18−/− mice is similar to the IL-18BP overexpressing ApoE−/− mice in that the lesions are smaller and their phenotype is more "stable" (Elhage et al. (2003) Cardiovasc Res 59:234). Administering a neutralising anti-IL-18 antibody in a rat vascular injury model significantly reduced neointima formation, corresponding to reduced intra-intimal cell proliferation, and IFNγ and IL-6 gene expression (Maffia et al (2006) Circulation 114:430). Additionally, IL-18−/− mice are susceptible to hyperphagia, obesity and insulin resistance (Netea et al (2006) Nat. Med. 12:650).

As described above, IL-18 may be considered a proinflammatory cytokine which mediates disease, as well as an immunostimulatory cytokine that is important for host defense against infection and cancer.

The high-affinity, constitutively expressed, and circulating IL-18 binding protein (IL-18BP), which competes with cell surface receptors for IL-18 and neutralizes IL-18 activity, may act as a natural anti-inflammatory as well as immunosuppressive molecule. In humans, four different isoforms (a, b, c and d) of IL-18BP have been identified resulting from alternative splicing. Only IL-18BPa and IL-18BPc have been shown to bind and neutralise the biological activity of human IL-18, isoform a having a 10-fold higher affinity than isoform c (Kim et al (2000) PNAS 97 1190-1195). Computer modeling of human IL-18 identified two charged residues, Glu-42 and Lys-89, which interact with oppositely charged amino acid residues buried in a large hydrophobic pocket of IL-18BP. The cell surface IL-18 receptor alpha chain competes with IL-18BP for IL-18 binding, although the IL-18 receptor alpha chain does not share significant homology to IL-18BP.

The structure of soluble IL-18 has been determined by NMR spectroscopy and consists of 12 strands forming a β-trefoil (Kato et al (2003) Nat. Struct. Biol. 10:966). Three specific surface areas have been identified. Site I is formed by five residues (Arg13, Asp17, Met33, Asp 35 and Asp 132) located on one side of the core barrel and is responsible for binding to IL-18Rα. Site II is formed by six residues (Lys4, Leu5, Lys8, Arg 58, Met60 and Arg104) located at the top of the β-barrel and is also important for IL-18Rα binding. Site III (Lys 79, Lys 89, asp98) located opposite to site II at the bottom of the β-barrel is binding to IL-18Rβ (Kato et al. (2003) supra).

Antibodies that bind IL-18 are known in the art (see for example U.S. Pat. No. 6,706,487, WO 2001/058956, EP 1621616, US 2005/0147610; EP 0 974 600; and WO 0158956). However, there is still a need for anti-IL-18 antibodies that reduce the biological activity of IL-18 in a therapeutic context.

SUMMARY OF THE INVENTION

Aspects of the invention provide isolated binding members for interleukin-18 (IL-18) which inhibit the binding of IL-18 to one or both of IL-18R and IL-18BP and thereby reduce IL-18 activity.

Binding members of the invention may bind to an epitope which wholly or partially overlaps the IL-18BP binding site on the Il-18 molecule. The IL-18BP binding site on the IL-18 molecule is shown in FIG. 13.

For example, binding members of the invention may bind to an epitope of human IL-18 which comprises one or more of residues Tyr1, Gly3, Leu5, Glu6, Lys8, Met51, Lys53, Asp54, Ser55, Gln56, Pro57, Arg58, Gly59, Met60, Arg104, Ser105, and Pro107.

Binding members of the invention may be useful in diagnosing and treating diseases associated with increased IL-18 activity, such as acute coronary syndrome (ACS); atherosclerosis; and chronic obstructive pulmonary disease (COPD).

Binding members of the invention may also be useful in measuring the amount of free IL-18 in a sample.

BRIEF DESCRIPTION OF THE FIGURES

FIG. 2 shows the inhibition of the formation of the human IL-18, IL-18 receptor alpha and IL-18 receptor beta complex by increasing concentrations of Antibody 1 IgG$_2$ (triangles) in graph A and the inhibition of the formation of the rhesus macaque IL-18, IL-18 receptor alpha and IL-18 receptor beta complex by increasing concentrations of Antibody 1 IgG$_2$ (triangles) in graph B. The Y axis represents the specific binding of the IL-18 to IL-18 receptor complex as a percentage of the total binding observed in the absence of any IgG. Data represent mean values of duplicate points with SEM.

FIG. 6 shows the inhibition of IFNγ release by KG-1 cells stimulated with exogenous human IL-18 and TNFα in the presence of increasing concentrations of germlined anti-IL-18 IgG. The neutralising effect of Antibody 11 GL (circles), Antibody 12 GL (squares), Antibody 8 GL (diamonds), all converted to IgG$_2$, and a control IgG (triangles) is shown in graph A. The neutralisation effect of Antibody 12 GL converted to IgG$_1$TM (opened squares) and a control IgG (opened triangles) is shown in graph B. The Y-axis represents the IFNγ release as a percentage of maximum response which is obtained in absence of neutralising antibodies. Data represent mean values of duplicate wells with SEM.

FIG. 7 shows the inhibition of IFNγ release by PBMC of human (graph A) and cynomolgus monkey (graph B) origins stimulated with LPS and human IL-12 in the presence of increasing concentrations of germlined Antibody 12 IgG$_1$TM (squares) and a control IgG (triangles). The Y-axis represents the IFNγ release as a percentage of maximum response which is obtained in absence of neutralising antibodies. Data represent mean values of 3 donors with SEM.

FIG. 10 shows the dose dependant induction of IFNγ release by KG-1 cells stimulated by human IL-18 in the presence of increasing amounts of Antibody 12 GL IgG$_1$TM (graph A) and the corresponding Schild plot used to determine the KD of the antibody (graph B).

FIG. 13 shows the residues (grey, underlined) within the IL-18 sequence which interact with Antibody 12 GL (top) and IL-18BP (bottom) (i.e. the epitope).

FIG. 14 shows the residues (grey; underlined) within the Antibody 12 GL sequence which interact with IL-18 (i.e. the paratope).

DETAILED DESCRIPTION

Figure 1:
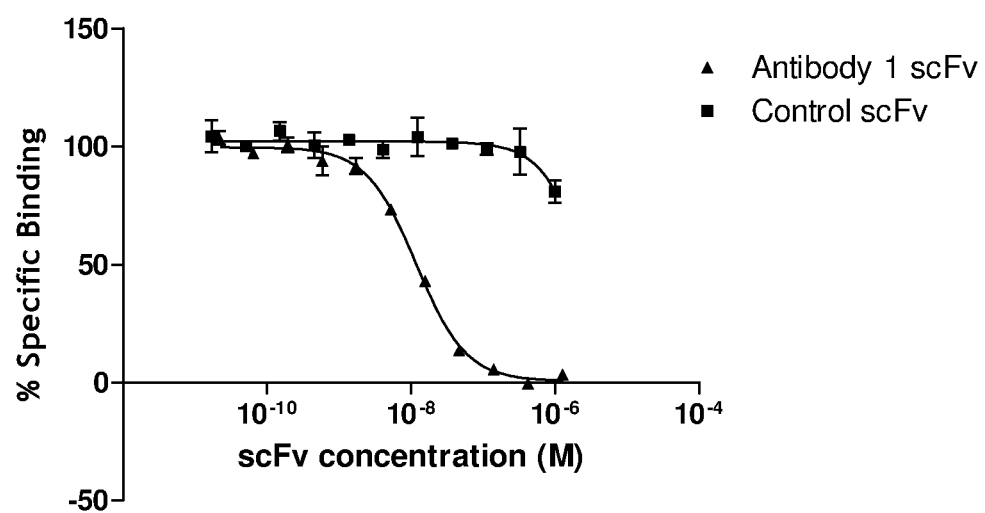
FIG. 1 shows the inhibition of the formation of the human IL-18, IL-18 receptor alpha and IL-18 receptor beta complex by increasing concentrations of Antibody 1 scFv (triangles). The Y axis represents the specific binding of the IL-18 to IL-18 receptor complex as a percentage of the total binding observed in the absence of any scFv. Data represent mean values of duplicate points with SEM.

The present invention provides binding members, including human, humanized and/or chimeric antibodies that bind to IL-18, as well as fragments, derivatives/conjugates and compositions thereof. Binding members as described herein may modulate the binding of IL-18 to IL-18BP and/or IL-18R and may be useful in decreasing the biological activity of IL-18, e.g. in vivo, ex vivo or in vitro. Binding members that bind to IL-18 may also be useful, for example, in detecting the presence of IL-18 in a sample.

An aspect of the invention provides an isolated binding member for IL-18 which inhibits the binding of IL-18 to one or both of IL-18R and IL-18BP and thereby reduces IL-18 activity.

An isolated binding member may bind to an epitope on the 11-18 molecule which wholly or partially overlaps the IL-18BP binding site.

The IL-18BP binding site is shown in FIG. 13.

For example, an isolated binding member for IL-18 may specifically bind to an epitope of IL-18 which comprises one or more of residues Tyr1, Gly3, Leu5, Glu6, Lys8, Met51, Lys53, Asp54, Ser55, Gln56, Pro57, Arg58, Gly59, Met60, Arg104, Ser105 and Pro107 of human IL-18 or the corresponding residues from IL-18 of other species, for example a primate such as Rhesus macaque.

A binding member for IL-18 may bind to an IL-18 epitope which comprises 1, 2, 3, 4, 5, 6, 7, 8, 9, 10, 11, 12, 13, 14, 15, 16 or all 17 residues selected from the group consisting of Tyr1, Gly3, Leu5, Glu6, Lys8, Met51, Lys53, Asp54, Ser55, Gln56, Pro57, Arg58, Gly59, Met60, Arg104, Ser105, and Pro107 of human IL-18.

For example, the IL-18 epitope may comprise residues Tyr1, Gly3, Leu5, Met51, Lys53, Asp54, Ser55, Gln56, Pro57, Arg58, Gly59, Met60, Arg104 and Ser105. Optionally, the epitope may further comprise residues Glu6, Lys8 and Pro107.

In some preferred embodiments, a binding member for IL-18 may bind to an IL-18 epitope which consists of Tyr1, Gly3, Leu5, Met51, Lys53, Asp54, Ser55, Gln56, Pro57, Arg58, Gly59, Met60, Arg104 and Ser105.

The sequence of IL-18, with epitope residues shown, is set out in FIG. 13.

Il-18 residues identified as being part of the IL-18 epitope are shown herein to be positioned within 0.5 nm (5 Å) of one or more residues of the antibody variable domain in the bound IL-18/antibody complex. In some embodiments, other Il-18 residues which are also located in the proximity of (e.g. within 0.75 nm or within 1 nm) a more residue of the antibody variable domain in the bound IL-18/antibody complex may also be considered to be part of the IL-18 epitope.

IL-18 is human IL-18, unless otherwise specified. A number of polymorphic variants of human IL-18 are known. The two most common polymorphic variants have accession numbers rs2854746 (A32G) and rs9282734 (H158P) in the SNP database. The sequence of human IL-18 is available on public databases (Gene ID: 3606; NCBI NP_001553.1 GI: 4504653; Uniprot Q14116-1) and the mature human IL-18 sequence is shown in SEQ ID NO: 169. Non-human IL-18 refers to an ortholog of IL-18 that occurs naturally in a species other than human, such as a rodent or non-human primate. IL-18 sequences from other species, including Rhesus macaques are known in the art and available on public databases such as Genbank. The residues in IL-18 sequences from other species corresponding to specific residues in human IL-18 may be easily identified using sequence alignment tools.

Recombinantly expressed mature human and rhesus macaque IL-18 were used to select and screen the antibody molecules described herein. Non-human orthologs, such as rodent and Rhesus macaque IL-18, were used in the experiments described herein for species cross reactive analysis.

Binding members as described bind to human IL-18. Binding members may also bind to the target epitope in IL-18 from other species. For example, a binding member as described herein may bind to IL-18 from a non-human primate, such as Rhesus Macaque and/or Cynomologous monkey. In some embodiments, a binding member may display no binding or substantially no binding to rodent IL-18, for example mouse or rat IL-18.

Binding members as described herein are specific for the target IL-18 epitope described herein and bind to this target epitope with high affinity relative to non-target epitopes, for example epitopes from proteins other than IL-18. For example, a binding member may display a binding affinity for IL-18 which is at least 10 fold, at least 100-fold, at least 500 fold, at least 1000 fold or at least 2000 fold greater than other human cytokines, such as IL-1β and IL-1F7.

Binding members may exhibit a dissociation constant ($k_d$) for human IL-18 and optionally Rhesus Macaque IL-18, of less than $10^{-2}$ s$^{-1}$, preferably less than $10^{-2}$ s$^{-1}$, more preferably less than $10^{-4}$ s$^{-1}$, for example, $9\times10^{-5}$ or less, and typically 2 to $9\times10^{-5}$ s$^{-1}$. (e.g., $2.9\times10^{-5}$ s$^{-1}$ for Antibody 12GL IgG1 TM as measured by Biacore as described herein).

Binding members may exhibit an affinity (kD) for human IL-18, of less than 10 nM, (e.g., Antibody 1, KD=9.96 nM measured in a Biacore assay as described herein); preferably less than 1 nM, more preferably less than 500 pM, more preferably less than 100 pM, yet further preferably less than 70 pM, (e.g., Antibody 12GL IgG1TM, KD=63 pM measured in a Biacore assay as described herein). Binding kinetics and affinity (expressed as the equilibrium dissociation constant $K_D$) of binding members may be determined using standard techniques, such as surface plasmon resonance e.g. using BIAcore™ analysis or pharmacologically using a cell-based assay (Schild plot/pA$_2$ analysis), as described herein.

Binding members as described herein may inhibit the binding of IL-18 to IL-18 receptor (IL-18R) and/or IL-18 binding protein (IL-18BP). For example, binding members may compete for binding to IL-18 with IL-18R (IL-18Rα, Uniprot accession #Q13478; IL-18Rβ, Uniprot accession #O95256) and/or IL-18BP, for example IL-18BP isoform a (Uniprot accession #O95998).

Competition may be measured using standard techniques, such as an IL-18/IL-18BP homogenous time resolved fluorescence (HTRF™) competition assay as described in the Examples. For example, a binding member may exhibit at least 70%, at least 75%, at least 80%, least 85% or at least 90% inhibition of IL-18BP binding to IL-18, as measured for example at 10 nM in a suitable assay, such as an HTRF™ IL-18/Il-18BP competition assay.

Binding members as described herein may inhibit the biological activity of IL-18. Inhibition of IL-18 activity by a binding member, for example in an assay described herein, indicates that the binding member binds and inhibits IL-18. The inhibition of IL-18 activity may be conveniently measured by a decrease in IFNγ production. Inhibition may also be measured by through the release of other soluble mediators, e.g. IL-8, MCP-1, CXCL16, GM-CSF, sICAM-1, and MMPs, for example by ELISA.

Techniques for measuring the production and release of IFNγ and other soluble mediators are well-known in the art and include cell based assays, such as the KG-1 assay and the PBMC assay; immunological techniques, such as ELISA, Western blotting and immunoprecipitation; affinity chromatography and other biochemical assays.

The inhibition of IL-18 activity may also be measured by a decrease in expression of activation markers on cells e.g. CD11b or a decrease in production of mediators of oxydative stress e.g. reactive oxygen species (ROS). Techniques for measuring the modulation of CD11b or ROS are well-known in the art and include cell based assays, such as the neutrophil stimulation assay; immunological techniques, such as immunostaining for flow cytometry and other biochemical assays.

Inhibition of IL-18 activity may be partial or total (i.e. neutralisation). For example, binding members may inhibit IL-18 activity by 100%, or at least 95%, at least 90%, at least 85%, at least 80%, at least 75%, at least 70%, at least 60%, or at least 50%, relative to the activity in absence of the binding member.

The neutralising potency of a binding member may be determined. Potency is normally expressed as an IC$_{50}$ value, in nM unless otherwise stated. In functional assays, IC$_{50}$ is the concentration of an antibody molecule that reduces a biological response by 50% of its maximum. In ligand-binding studies, IC$_{50}$ is the concentration that reduces receptor binding by 50% of maximal specific binding level. IC$_{50}$ may be calculated by plotting % of maximal biological response as a function of the log of the binding member concentration, and using a software program, such as Prism (GraphPad) or Origin (Origin Labs) to fit a sigmoidal function to the data to generate IC$_{50}$ values. Suitable assays for measuring or determining potency are well known in the art.

Binding members as described herein may exhibit an IC$_{50}$ value (expressed as the geometric mean of the potency) for IL-18 of less than 260 nM, less than 100 nM, less than 10 nM, less than 5 nM, less than 1 nM, or less than 0.5 nM as measured, for example, by IL-18 triggered release of IFNγ. Suitable assays for IFNγ release include KG-1 and PBMC assays, as described herein.

The neutralising potency of a binding member as calculated in an assay using IL-18 from a first species (e.g. human) may be compared with neutralising potency of the binding member in the same assay using IL-18 from a second species (e.g. Rhesus Macaque IL-18), in order to assess the extent of cross-reactivity of the binding member for IL-18 of the two species. Binding members described herein may have a greater neutralising potency in a human IL-18 assay than in a non-human IL-18 assay. For example, the neutralising potency of a binding member for human IL-18 may be greater than for Rhesus Macaque IL-18.

A binding member may comprise an antibody molecule having one or more CDRs, e.g. a set of CDRs, within an antibody framework (i.e. an antibody antigen binding domain). For example, an antibody molecule may comprise an antibody VH and/or VL domain. VH and VL domains of antibody molecules are also provided as part of the invention. As is well-known, VH and VL domains comprise complementarity determining regions, ("CDRs"), and framework regions, ("FWs"). A VH domain comprises a set of HCDRs and a VL domain comprises a set of LCDRs. An antibody molecule may comprise an antibody VH domain comprising a VH CDR1, CDR2 and CDR3 and/or an antibody VL domain comprising a VL CDR1, CDR2 and CDR3. VH or VL domains may further comprise a framework. A VH or VL domain framework typically comprises four framework regions, FW1, FW2, FW3 and FW4, which are interspersed with CDRs in the following structure: FW1-CDR1-FW2-CDR2-FW3-CDR3-FW4.

Examples of antibody VH and VL domains, FWs and CDRs according to aspects of the invention are listed in Tables 10 and 11 and the appended sequence listing that forms part of the present disclosure. All VH and VL sequences, CDR sequences, sets of CDRs, sets of HCDRs and sets of LCDRs disclosed herein, as well as combinations of these elements, represent aspects of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs. Typically antibody molecules of the invention are monoclonal antibodies.

In other embodiments, a binding member may comprise an antigen-binding site within a non-antibody molecule, normally provided by one or more CDRs e.g. a set of CDRs in a non-antibody protein scaffold, as discussed further below.

The isolation of a parent antibody molecule designated Antibody 1 with a set of CDR sequences and framework sequences as shown in Tables 10, 11 and the sequence listing, is described herein. Through a process of optimisation, a panel of antibody clones have been generated from Antibody 1 which are designated Antibody 1 GL, Antibody 2, Antibody 3, Antibody 4, Antibody 5, Antibody 6, Antibody 6 GL, Antibody 7, Antibody 7 GL, Antibody 8_GL, Antibody 9, Antibody 10, Antibody 11, Antibody 11 GL, and Antibody 12 GL. The CDR sequences and variable domain sequences of these optimised clones are referenced in Tables 10 and 11 and set out in the sequence listing. For example, table 11 shows that antibody 1 has a set of CDRs, in which HCDR1 is SEQ ID NO: 3 (Kabat residues 31-35b), HCDR2 is SEQ ID NO: 4 (Kabat residues 50-65), HCDR3 is SEQ ID NO: 5 (Kabat residues 95-102), LCDR1 is SEQ ID NO: 8 (Kabat residues 24-34), LCDR2 is SEQ ID NO: 9 (Kabat residues 50-56) and LCDR3 is SEQ ID NO: 10 (Kabat residues 89-97). Antibody 2 has the HCDR1, HCDR2, HCDR3, LCDR1, LCDR2 and LCDR3 sequences of SEQ ID NOS: 23, 24, 25, 28, 29, and 30, respectively. The other optimised antibody clones are shown in Table 11 in a similar way and are also provided as aspects of the invention.

A binding member for IL-18 in accordance with the invention may comprise one or more CDRs as described herein, e.g. a CDR3, and optionally also a CDR1 and CDR2 to form a set of CDRs. The CDR or set of CDRs may be an Antibody 1 CDR or Antibody 1 set of CDRs, or may be a CDR or set of CDRs of any of Antibody 1 GL, Antibody 2, Antibody 3, Antibody 4, Antibody 5, Antibody 6, Antibody 6 GL, Antibody 7, Antibody 7 GL, Antibody 8 GL, Antibody 9, Antibody 10, Antibody 11, Antibody 11 GL, and Antibody 12 GL, or may be a variant thereof as described herein.

In some embodiments;
HCDR1 may be 7 amino acids long, consisting of Kabat residues 31-35b;
HCDR2 may be 16 amino acids long, consisting of Kabat residues 50-65;
HCDR3 may be 15 amino acids long, consisting of Kabat residues 95-102;
LCDR1 may be 11 amino acids long, consisting of Kabat residues 24-34;
LCDR2 may be 7 amino acids long, consisting of Kabat residues 50-56; and/or
LCDR3 may be 9 amino acids long, consisting of Kabat residues 89-97.

Binding members may comprise a HCDR1, HCDR2 and/or HCDR3 and/or an LCDR1, LCDR2 and/or LCDR3 of any of the antibodies listed in Table 11 e.g. a set of CDRs of any of the antibodies listed in Table 11. The binding member may comprise a set of VH CDRs of any one of these antibodies. Optionally, it may also comprise a set of VL CDRs of one of these antibodies. The VL CDRs may be from the same or a different antibody as the VH CDRs. A VH domain comprising a set of HCDRs of any of the antibodies listed in Table 11, and/or a VL domain comprising a set of LCDRs of any of the antibodies listed in Table 11, are also provided herein.

A binding member which specifically binds to interleukin-18 (IL-18) as described herein may comprise:
(a) a HCDR1 having an amino acid sequence identical to or comprising 1, 2, or 3 amino acid residue substitutions relative to SEQ ID NO: 153;
(b) a HCDR2 having an amino acid sequence identical to or comprising 1, 2, 3 or 4 amino acid residue substitutions relative to SEQ ID NO: 154;
(c) a HCDR3 having an amino acid sequence identical to or comprising 1, 2, 3, 4 or 5 amino acid residue substitutions relative to SEQ ID NO: 155;
(d) a LCDR1 having an amino acid sequence identical to or comprising 1, 2, 3 or 4 amino acid residue substitutions relative to SEQ ID NO: 158;
(e) a LCDR2 having an amino acid sequence identical to or comprising 1, 2, 3 or 4 amino acid residue substitutions relative to SEQ ID NO: 159; and
(f) a LCDR3 having an amino acid sequence identical to or comprising 1, 2, 3, 4, 5, 6, 7, 8, or 9 amino acid residue substitutions relative to SEQ ID NO: 160.

A binding member may comprise a set of H and/or L CDRs of the parent antibody Antibody 1 or any of the antibodies listed in Table 11 with one or more substitutions e.g. up to 15, up to 16, or up to 17 substitutions, within the disclosed set of H and/or L CDRs. For example, an antibody molecule of the invention may comprise the set of H and/or L CDRs from any one of Antibody 1, Antibody 1 GL, Antibody 2, Antibody 3, Antibody 4, Antibody 5, Antibody 6, Antibody 6 GL, Antibody 7, Antibody 7 GL, Antibody 8 GL, Antibody 9, Antibody 10, Antibody 11, Antibody 11 GL, and Antibody 12 GL, with 17, 16 or 15 or fewer substitutions, e.g. 14, 13, 12, 11, 10, 9, 8, 7, 6, 5, 4, 3, 2 or 1 substitutions. Substitutions may potentially be made at any residue within the set of CDRs.

For example, a suitable antibody molecule may comprise a set of CDRs: HCDR1, HCDR2, HCDR3, LCDR1, LCDR2 and LCDR3, wherein the set of CDRs has 17, 16 or 15 or fewer amino acid substitutions from;
(i) a set of Antibody 1 CDRs in which:
HCDR1 is amino acid sequence SEQ ID NO: 3;
HCDR2 is amino acid sequence SEQ ID NO: 4;
HCDR3 is amino acid sequence SEQ ID NO: 5;
LCDR1 is amino acid sequence SEQ ID NO: 8;
LCDR2 is amino acid sequence SEQ ID NO: 9; and
LCDR3 is amino acid sequence SEQ ID NO: 10, (ii) a set of Antibody 11 GL CDRs in which:
HCDR1 is amino acid sequence SEQ ID NO: 143;
HCDR2 is amino acid sequence SEQ ID NO: 144;
HCDR3 is amino acid sequence SEQ ID NO: 145;
LCDR1 is amino acid sequence SEQ ID NO: 148;
LCDR2 is amino acid sequence SEQ ID NO: 149; and
LCDR3 is amino acid sequence SEQ ID NO: 150; or
(iii) a set of Antibody 12 GL CDRs in which:
HCDR1 is amino acid sequence SEQ ID NO: 153;
HCDR2 is amino acid sequence SEQ ID NO: 154;
HCDR3 is amino acid sequence SEQ ID NO: 155;
LCDR1 is amino acid sequence SEQ ID NO: 158;
LCDR2 is amino acid sequence SEQ ID NO: 159; and
LCDR3 is amino acid sequence SEQ ID NO: 160.

In some embodiments, substitutions may be made at residues which are located more than 0.5 nm (5 Å) away from an IL-18 residue in the IL-18/mAb complex. (see FIG. 14). For example, an HCDR3 may comprise substitutions at 1, 2, 3, 4 or 5 positions selected from Kabat residues 95, 96, 100A, 100B, 100C, 100f, 100g, 101 and 102. An HCDR2 may comprise substitutions at 1, 2, 3 or 4 positions selected from Kabat residues 50, 51, 54-57 and 59-65. An HCDR1 may comprise substitutions at 1, 2 or 3 positions selected from Kabat residues 31-34, 35a and 35b. A suitable LCDR3 may comprise substitutions at 1, 2, 3, or 4 positions selected from Kabat residues 89, 90, 95 and 97. A LCDR2 may comprise substitutions at 1, 2, 3, or 4 positions selected from Kabat residues 50 to 56. A LCDR1 may comprise substitutions at 1, 2, 3, or 4 positions selected from Kabat residues 24 to 29, 31, 33 and 34.

In some embodiments, substitutions may be made at the positions substituted in any of Antibody 1 GL, Antibody 2, Antibody 3, Antibody 4, Antibody 5, Antibody 6, Antibody 6 GL, Antibody 7, Antibody 7 GL, Antibody 8 GL, Antibody 9, Antibody 10, Antibody 11, Antibody 11 GL, and Antibody 12 GL, as shown in Table 11. Thus, the one or more substitutions may be at one or more of the following residues:
Kabat residue 99, 100a, 100b and 100d in HCDR3;
Kabat residue 89, 90, 91, 92, 93, 94, 95, and 97 in LCDR3.
Binding members may comprise an HCDR3 in which:
Kabat residue 95 is Thr;
Kabat residue 96 is Pro
Kabat residue 97 is Ala;
Kabat residue 98 is Tyr;
Kabat residue 99 is Asp or Phe;
Kabat residue 100 is Gly;
Kabat residue 100A is Asp or Gln;
Kabat residue 100B is Ala or Asp;
Kabat residue 100C is Arg
Kabat residue 100D is Ala or Thr;
Kabat residue 100E is Asp;
Kabat residue 100F is Phe;
Kabat residue 100G is Phe;
Kabat residue 101 is Asp; and/or
Kabat residue 102 is Val.
For example, Kabat residue 99 may be Phe; Kabat residue 100a may be Gln; Kabat residue 100b may be Asp; and/or Kabat residue 100d in HCDR3 may be Thr.
Binding members may comprise an LCDR3 in which:
Kabat residue 92 is Tyr, Ser, Leu, His, or Ala;
Kabat residue 93 is Ser, Phe, Tyr, His, or Ile; and/or
Kabat residue 94 is Thr or Pro.
For example, a binding member may comprise an LCDR3 in which;
Kabat residue 89 is Gln or Ala;
Kabat residue 90 is Gln, Asp, or Asn;
Kabat residue 91 is Ser or Ile;
Kabat residue 92 is Tyr, Ser, Leu, His, or Ala;
Kabat residue 93 is Ser, Phe, Tyr, His, or Ile;
Kabat residue 94 is Thr or Pro;
Kabat residue 95 is Pro, Asn, or Gln,
Kabat residue 96 is Trp and/or
Kabat residue 97 is Thr or Asp.

In some preferred embodiments, Kabat residue 92 in LCDR3 may be His; Kabat residue 93 may be His; and/or Kabat residue 94 may be Pro.

In some examples of binding members, HCDR1 may be one of SEQ ID NOS: 3, 103, 113 or 153; and HCDR2 may be one of SEQ ID NO: 4, 104, 124, or 134. For example, HCDR1 may be SEQ ID NO: 153; and HCDR2 may be SEQ ID NO: 154.

HCDR3 may be one of SEQ ID NO: 5, 15, 25, 35, 45, 55, 65, 75, 85, 95, 105, 115, 125, 135, 145, or 155. For example, HCDR3 may be SEQ ID NO: 155.

LCDR1 may be SEQ ID NO 158; and LCDR2 may be amino acid sequence SEQ ID NO: 159.

LCDR3 may be one of SEQ ID NOS: 10, 20, 30, 40, 50, 60, 70, 80, 90, 100, 110, 120, 130, 140, 150, or 160. For example, LCDR3 may be SEQ ID NO: 160.

As described above, a binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene segment sequences. Thus, the framework may be germlined, whereby one or more residues within the framework are changed to match the residues at the equivalent position in the most similar human germline framework. The skilled person can select a germline segment that is closest in sequence to the framework sequence of the antibody before germlining and test the affinity or activity of the antibodies to confirm that germlining does not significantly reduce antigen binding or potency in assays described herein. Human germline gene segment sequences are known to those skilled in the art and can be accessed for example from the VBASE compilation (VBASE, MRC Centre of Protein Engineering, UK, 1997, http//mrc-cpe.cam.ac.uk).

A binding member as described herein may be an isolated human antibody molecule having a VH domain comprising a set of HCDRs in a human germline framework, e.g. Vh4 DP66(4-61). Thus, the VH domain framework regions FW1, FW2 and/or FW3 may comprise framework regions of human germline gene segment Vh4 DP66(4-61) and/or may be germlined by mutating framework residues to match the framework residues of this human germline gene segment. FW4 may comprise a framework region of human germline j segment JH2. The amino acid sequence of VH FW1 may be SEQ ID NO: 161. The amino acid sequence of VH FW2 may be SEQ ID NO: 162. The amino acid sequence of VH FW3 may be SEQ ID NO: 163. The amino acid sequence of VH FW4 may be SEQ ID NO: 164. Normally the binding member also has a VL domain comprising a set of LCDRs, e.g. in a human germline framework, e.g. V kappa 1 L12. Thus, the VL domain framework regions may comprise framework regions FW1, FW2 and/or FW3 of human germline gene segment V kappa 1 L12 and/or may be germlined by mutating framework residues to match the framework residues of this human germline gene segment. FW4 may comprise a framework region of human germline j segment JK2. The amino acid sequence of VL FW1 may be SEQ ID NO: 165. The amino acid sequence of VL FW2 may be SEQ ID NO: 166. The amino acid sequence of VL FW3 may be SEQ ID NO: 167. The amino acid sequence of VL FW4 may be SEQ ID NO:

168. A germlined VH or VL domain may or may not be germlined at one or more Vernier residues, but is normally not.

Antibody molecules of the invention may comprise a heavy chain FW1 in which
  Kabat residue 6 may be Gln or Glu;
  Kabat residue 10 may be Arg or Gly;
  Kabat residue 13 may be Lys or Glu; and/or
  Kabat residue 16 may be Gln or Glu.

Antibody molecules of the invention may comprise a heavy chain FW2 in which Kabat residue 41 Ala or Pro and/or a heavy chain FW3 in which Kabat residue 74 is Pro or Ser.

Antibody molecules of the invention may comprise a light chain FW1 in which Kabat residue 3 is Val or Gln; a light chain FW2 in which Kabat residue 42 is Arg, Lys or Gly; a light chain FW3 in which Kabat residue 70 is Asp or Glu and/or Kabat residue 81 is Glu or Asp; and/or a light chain FW4 in which Kabat residue 99 is Gly or Ser.

For example, an antibody molecule or a VH domain as described herein may comprise the following set of heavy chain framework regions:
  FW1 SEQ ID NO: 161;
  FW2 SEQ ID NO: 162;
  FW3 SEQ ID NO: 163;
  FW4 SEQ ID NO: 164;
or may comprise the said set of heavy chain framework regions with 1, 2, 3, 4, 5, 6 or 7 amino acid alterations, e.g. substitutions.

An antibody molecule or a VL domain as described herein may comprise the following set of light chain framework regions:
  FW1 SEQ ID NO: 165;
  FW2 SEQ ID NO: 166;
  FW3 SEQ ID NO: 167;
  FW4 SEQ ID NO: 168;
or may comprise the said set of light chain framework regions with 1, 2, 3, 4, 5, or 6 amino acid alterations, e.g. substitutions.

An amino acid alteration may be a substitution, an insertion or a deletion.

For example, an antibody molecule may comprise a set of heavy and light chain framework regions, wherein
  heavy chain FW1 is SEQ ID NO: 161;
  heavy chain FW2 is SEQ ID NO: 162;
  heavy chain FW3 is SEQ ID NO: 163;
  heavy chain FW4 is SEQ ID NO: 164;
  light chain FW1 is SEQ ID NO: 165;
  light chain FW2 is SEQ ID NO: 166;
  light chain FW3 is SEQ ID NO: 167;
  light chain FW4 is SEQ ID NO: 168;
Or may comprise the said set of heavy and light chain framework regions with 11 or fewer, e.g. 1, 2, 3, 4, 5, 6, 7, 8, 9 or 10 amino acid alterations, e.g. substitutions. For example there may be one or two amino acid substitutions in the said set of heavy and light chain framework regions.

A non-germlined antibody molecule has the same CDRs, but different frameworks, compared to a germlined antibody molecule. Of the antibody sequences shown herein in the appended sequence listing, sequences of Antibody 1, Antibody 6, Antibody 7, Antibody 8, Antibody 11, and Antibody 12 are germlined. Germlined antibodies of Antibody 2, Antibody 3, Antibody 4, Antibody 5, and Antibody 9 and Antibody 10 may be produced by germlining framework regions of the VH and VL domain sequences shown herein for the other antibodies.

Typically, a VH domain is paired with a VL domain to provide an antibody antigen-binding site, although as discussed above a VH or VL domain alone may be used to bind antigen. For example, the Antibody 12 GL VH domain (SEQ ID NO: 152) may be paired with the Antibody 12 GL VL domain (SEQ ID NO:157), so that an antibody antigen-binding site is formed comprising both the Antibody 12 GL VH and VL domains. Analogous embodiments are provided for the VH and VL domains of the other antibodies disclosed herein. In other embodiments, the Antibody 12 GL VH is paired with a VL domain other than the antibody Antibody 12 GL VL. Light-chain promiscuity is well established in the art. Again, analogous embodiments are provided by the invention for the other VH and VL domains disclosed herein. Thus, the VH of the parent Antibody 1 or of any of the optimised clones Antibody 1 GL, Antibody 2, Antibody 3, Antibody 4, Antibody 5, Antibody 6, Antibody 6 GL, Antibody 7, Antibody 7 GL, Antibody 8 GL, Antibody 9, Antibody 10, Antibody 11, Antibody 11 GL, and Antibody 12 GL may be paired with a VL domain from a different antibody e.g. the VH and VL domains may be from different antibodies selected from Antibody 1, Antibody 1 GL, Antibody 2, Antibody 3, Antibody 4, Antibody 5, Antibody 6, Antibody 6 GL, Antibody 7, Antibody 7 GL, Antibody 8 GL, Antibody 9, Antibody 10, Antibody 11, Antibody 11 GL, and Antibody 12 GL.

An isolated binding member may comprise a VH domain and a VL domain in which;
  (i) the VH domain amino acid sequence is shown in SEQ ID NO: 142 and the VL domain amino acid sequence is shown in SEQ ID NO: 147.
  (ii) the VH domain amino acid sequence has 1, 2, 3, 4, 5, 6, 7, 8, 9, 10, 11, 12, 13, 14 or 15 amino acid substitutions as compared to SEQ ID NO: 142 and the VL domain amino acid sequence has 8, 9, 10, 11, 12 or 13 amino acid substitutions as compared to SEQ ID NO: 147; or
  (iii) the VH domain amino acid sequence has at least 80%, at least 85%, at least 90% or at least 95% sequence identity with SEQ ID NO: 142 and the VL domain amino acid sequence has at least 80%, at least 85%, at least 90% or at least 95% sequence identity with SEQ ID NO: 147.

An isolated binding member may comprise a VH domain and a VL domain wherein;
  (i) the VH domain amino acid sequence is shown in SEQ ID NO: 152 and the VL domain amino acid sequence is shown in SEQ ID NO: 157,
  (ii) the VH domain amino acid sequence has 1, 2, 3, 4, 5, 6, 7, 8, 9, 10, 11, 12, 13, 14 or 15 amino acid substitutions as compared to SEQ ID NO: 152 and the VL domain amino acid sequence has 1, 2, 3, 4, 5, 6, 7, 8, 9, 10, 11, 12 or 13 amino acid substitutions as compared to SEQ ID NO: 157; or
  (iii) the VH domain amino acid sequence has at least 80%, at least 85%, at least 90% or at least 95% sequence identity with SEQ ID NO: 152 and the VL domain amino acid sequence has at least 80%, at least 85%, at least 90% or at least 95% sequence identity with SEQ ID NO: 157.

An isolated binding member may comprise a VH domain and a VL domain wherein;
  (i) the VH domain amino acid sequence is shown in SEQ ID NO: 102 and the VL domain amino acid sequence is shown in SEQ ID NO: 107,
  (ii) the VH domain amino acid sequence has 1, 2, 3, 4, 5, 6, 7, 8, 9, 10, 11, 12, 13, 14 or 15 amino acid substitutions as compared to SEQ ID NO: 102 and the VL domain amino acid sequence has 1, 2, 3, 4, 5, 6, 7, 8, 9, 10, 11, 12 or 13 amino acid substitutions as compared to SEQ ID NO: 107; or
  (iii) the VH domain amino acid sequence has at least 80%, at least 85%, at least 90% or at least 95% sequence identity with SEQ ID NO: 102 and the VL domain amino acid sequence has at least 80%, at least 85%, at least 90% or at least 95% sequence identity with SEQ ID NO: 107.

In some embodiments, an antibody molecule may lack antibody constant regions, for example a scFv.

In other embodiments, an antibody molecule may comprise an antibody constant region. An antibody molecule may be a whole antibody such as an IgG, i.e. an IgG1, IgG2, or IgG4, or may be an antibody fragment or derivative as described below. Antibody molecules can also have other formats, e.g. IgG1 with YTE (Dall'Acqua et al. (2002) J. Immunology, 169: 5171-5180; Dall'Acqua et al. (2006) J Biol. Chem. 281(33):23514-24) and/or TM mutations (Oganesyan et al. (2008) Acta Cryst D64:700-4) in Fc region.

E. coli TOP10 cells containing a vector encoding the VH and VL domains of antibody 12_GL were deposited under the terms of the Budapest treaty at the National Collection of Industrial, food and Marine Bacteria (NCIMB) (NCIMB Ltd, Aberdeen UK) on 23 Nov. 2010 under accession number NCIMB 41786. The nucleotide sequences of the deposited VH and VL domains are shown in SEQ ID NOS: 152 and 157.

A binding member as described herein may comprise a CDR, VH domain, VL domain, antibody-antigen binding site or antibody molecule which is encoded by the nucleic acid sequences and/or the vector of deposit accession number NCIMB 41786.

A binding member as described herein may be produced or producible from the nucleic acid, vector or cell line of deposit accession number NCIMB 41786. For example, a binding member may be produced by expression of the nucleic acid or vector of the cell line of deposit accession number NCIMB 41786. The nucleic acid or vector may be expressed any convenient expression system. Alternatively, the binding member may be expressed by the cell line of deposit accession number NCIMB 41786.

Aspects of the invention also provide nucleic acid encoding the VH and/or VL domains, which is contained in the cell line of accession number NCIMB 41786; a vector comprising said nucleic acid, which is contained in the cell line of accession number NCIMB 41786; and the cells or cell line of accession number NCIMB 41786.

Another aspect of the invention provides a binding member comprising an antibody antigen binding site or antibody molecule as described herein which competes for binding to IL-18 with any antibody molecule which (i) binds IL-18 and (ii) comprises an antibody molecule, VH and/or VL domain, CDR e.g. HCDR3, and/or set of CDRs listed in Tables 10 and 11.

For example, a binding member, such as an antibody molecule, may compete with an antibody molecule comprising:

(i) a VH domain having the sequence of SEQ ID NO. 152 and a VL domain having the sequence of SEQ ID NO. 157;

(ii) a VH domain having a sequence with 15 or fewer amino acid substitutions such as 14, 13, 12, 11, 10, 9, 8, 7, 6, 5, 4, 3, 2, or 1 as compared to SEQ ID NO. 152; and a VL domain having a sequence with 13 or fewer amino acid substitutions such as 12, 11, 10, 9, 8, 7, 6, 5, 4, 3, 2, or 1 as compared to or SEQ ID NO. 157, or;

(iii) a VH domain and a VL domain having sequences with at least 90% sequence identity to SEQ ID NO. 152 and SEQ ID NO. 157, respectively.

Competition between binding members may be assayed easily in vitro, for example using ELISA and/or by a biochemical competition assay such as one tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein.

In further aspects, the invention provides an isolated nucleic acid which comprises a sequence encoding a binding member, VH domain and/or VL domain according to the present invention, and methods of preparing a binding member, a VH domain and/or a VL domain of the invention, which comprise expressing said nucleic acid under conditions to bring about production of said binding member, VH domain and/or VL domain, and recovering it.

For example, aspects of the invention provide the isolated VH domain nucleic acid sequences of SEQ ID NOS: 1, 11, 21, 31, 41, 51, 61, 71, 81, 91, 101, 111, 121, 131, 141, 151 and 170; the isolated VL domain nucleic acid sequences of SEQ ID NOS: 6, 16, 26, 36, 46, 56, 66, 76, 86, 96, 106, 116, 126, 136, 146, 156 and 171; and isolated nucleic acids, constructs and vectors comprising pairings of said VH and VL nucleic acid sequences.

Another aspect of the present invention provides an isolated nucleic acid encoding a VH CDR or VL CDR sequence disclosed herein, for example in Tables 10 and 11 or the sequence listing.

Another aspect of the present invention provides a vector, such as a plasmid or phage vector, comprising an isolated nucleic acid described above, for example operably linked to a regulatory element.

A further aspect provides a host cell containing or transformed with the nucleic acids and/or vectors of the invention.

Further aspects of the present invention provide for the use of binding members of the invention in the measurement of IL-18, preferably free IL-18 (i.e. IL-18 which is not bound to IL-18BP), and assay methods for measuring free IL-18 in for example in samples obtained from an individual.

Further aspects of the present invention provide for compositions containing binding members of the invention, and their use in methods of inhibiting and/or neutralising IL-18, including methods of treatment of the human or animal body by therapy.

Binding members according to the invention may be used in a method of treatment or diagnosis, such as a method of treatment (which may include prophylactic treatment) of a disease or disorder in the human or animal body (e.g. in a human patient), which comprises administering to said patient an effective amount of a binding member of the invention. Conditions treatable in accordance with the present invention include any in which IL-18 plays a role, as discussed in detail elsewhere herein, for example conditions associated with elevated IL-18 levels.

These and other aspects of the invention are described in further detail below.

Binding Member

The term binding member describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of CDRs on non-antibody protein scaffolds, such as fibronectin or cytochrome B etc. [Haan & Maggos (2004) BioCentury, 12(5): A1-A6; Koide et al. (1998) Journal of Molecular Biology, 284: 1141-1151; Nygren et al. (1997) Current Opinion in Structural Biology, 7: 463-4691], or by randomising or mutating amino acid residues of a loop within a protein scaffold to confer binding specificity for a desired target. Scaffolds for engineering novel binding sites in proteins have been reviewed in detail by Nygren et al. [supra]. Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs or an HCDR3 and/or LCDR3, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 [Wess, L. In: BioCentury, The Bernstein Report on BioBusiness, 12(42), A1-A7, 2004]. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a binding member may comprise other amino acids, e.g. forming a peptide or polypeptide, such as a folded domain, or to impart to the molecule another functional characteristic in addition to ability to bind antigen. Binding members may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR, e.g. CDR3, or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., 1987 [Kabat, E. A. et al, Sequences of Proteins of Immunological Interest. 4$^{th}$ Edition. US Department of Health and Human Services. 1987] and updates thereof. A number of academic and commercial on-line resources are available to query this database. For example, see Martin, A.C.R. Accessing the Kabat Antibody Sequence Database by Computer PROTEINS: Structure, Function and Genetics, 25 (1996), 130-133 and the associated on-line resource, currently at the web address of http://www.bioinf.org.uk/abs/simkab.html.

By CDR region or CDR, it is intended to indicate the hypervariable regions of the heavy and light chains of the immunoglobulin as defined by Kabat et al. 1991 [Kabat, E. A. et al. (1991) Sequences of Proteins of Immunological Interest, 5th Edition. US Department of Health and Human Services, Public Service, NIH, Washington], and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974; Amit et al., Science, 233:747-753, 1986; Chothia et al., J. Mol. Biol., 196:901-917, 1987; hothia et al., Nature, 342: 877-883, 1989; Caton et al., J. Immunol., 144:1965-1968, 199; Sharon et al., PNAS, 87:4814-4817, 1990; Sharon et al., J. Immunol., 144:4863-4869, 1990; and Kabat et al., J. Immunol., 147:1709-1719, 1991).

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example Fab$_2$, Fab$_3$, diabodies, triabodies, tetrabodies and minibodies. Antibody molecules and methods for their construction and use are described in Holliger & Hudson, *Nature Biotechnology* 23(9):1126-1136 2005.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel [Kontermann, R & Dubel, S, *Antibody Engineering*, Springer-Verlag New York, LLC; 2001, ISBN: 3540413545]. Phage display, another established technique for generating binding members has been described in detail in many publications, such as Kontermann & Dubel [supra] and WO92/01047 (discussed further below), and U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160, U.S. Pat. No. 6,521,404.

Transgenic mice in which the mouse antibody genes are inactivated and functionally replaced with human antibody genes while leaving intact other components of the mouse immune system, can be used for isolating human antibodies [Mendez, M. et al. (1997) Nature Genet, 15(2): 146-156]. Humanised antibodies can be produced using techniques known in the art such as those disclosed in for example WO91/09967, U.S. Pat. No. 5,585,089, EP592106, U.S. Pat. No. 565,332 and WO93/17105. Further, WO2004/006955 describes methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors, for example as described by Knappik et al. [Knappik et al. J. Mol. Biol. (2000) 296, 57-86] or Krebs et al. [Krebs et al. Journal of Immunological Methods 254 2001 67-84].

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [Ward, E. S. et al., Nature 341, 544-546 (1989); McCafferty et al (1990) Nature, 348, 552-554; Holt et al (2003) Trends in Biotechnology 21, 484-490], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [Bird et al, Science, 242, 423-426, 1988; Huston et al, PNAS USA, 85, 5879-5883, 1988]; (viii) bispecific single chain Fv dimers (PCT/US92/09965) and (ix) "diabodies", multivalent or multispecific fragments constructed by gene fusion (WO94/13804; Holliger, P. et al, Proc. Natl. Acad. Sci. USA 90 6444-6448, 1993). Fv, scFv or diabody molecules may be stabilized by the incorporation of disulphide bridges linking the VH and VL domains [Reiter, Y. et al, Nature Biotech, 14, 1239-1245, 1996]. Minibodies comprising a scFv joined to a CH3 domain may also be made [Hu, S. et al, Cancer Res., 56, 3055-3061, 1996]. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Qui et al. [Qui et al., *Nat. Biotechnol.* 25:921-929 2007] described antibody molecules containing just two CDRs linked by a framework region. CDR3 from the VH or VL domain was linked to the CDR1 or CDR2 loop of the other domain. Linkage was through the C terminus of the selected CDR1 or CDR2 to the N terminus of the CDR3, via a FR region. Qui et al. selected the FR region having the fewest hydrophobic patches. The best combination for the antibody tested was found to be VL CDR1 linked by VH FR2 to VH CDR3 (VHCDR1-VHFR2-VLCDR3). At a molecular weight of around 3 kDa, these antibody molecules offer advantages in terms of improved tissue penetration as compared with full immunoglobulins (approx. 150 kDa) or scFv (approx. 28 kDa).

Antibody fragments of the invention can be obtained starting from any of the antibodies listed herein, by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™". A binding member of the present invention may be a dAb comprising a VH or VL domain substantially as set out herein, or a VH or VL domain comprising a set of CDRs substantially as set out herein.

Bispecific or bifunctional antibodies form a second generation of monoclonal antibodies in which two different variable regions are combined in the same molecule [Holliger and Bohlen 1999 Cancer and metastasis rev. 18: 411-419]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [Holliger, P. and Winter G. Current Opinion Biotechnol 4, 446-449 1993], e.g. prepared chemically or from hybrid hybridomas, or may be any of the bispecific antibody fragments mentioned above. These antibodies can be obtained by chemical methods [Glennie M J et al., 1987 J. Immunol. 139, 2367-2375; Repp R. et al., 1995 J. Hemat. 377-382] or somatic methods [Staerz U. D. and Bevan M. J. 1986 PNAS 83; Suresh M. R. et al., 1986 Method Enzymol. 121: 210-228] but likewise and preferentially by genetic engineering techniques which allow the heterodimerization to be forced and thus facilitate the process of purification of the antibody sought [Merchand et al., 1998 Nature Biotech. 16:677-681]. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides, such as antibody fragments) of appropriate binding specificities can be readily selected using phage display (WO94/13804) from libraries. If one arm of the diabody is to be kept constant, for instance, with a specificity directed against IL-18, then a library can be made where the other arm is varied and an antibody of appropriate specificity selected. Bispecific whole antibodies may be made by alternative engineering methods as described in Ridgeway et al., 1996 [Ridgeway, J. B. B. et al, Protein Eng., 9, 616-621, 1996].

Various methods are available in the art for obtaining antibodies against IL-18. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" [Harlow and Lane, Antibodies: A Laboratory Manual, Cold Spring Harbor Laboratory, Cold Spring Harbor N.Y., pp. 726, 1988] or to the technique of preparation from hybridomas described by Köhler and Milstein [Köhler and Milstein, Nature, 256:495-497, 1975].

Monoclonal antibodies can be obtained, for example, from an animal cell immunized with IL-18, or one of its fragments containing the epitope recognized by said monoclonal antibodies. Suitable fragments and peptides or polypeptides comprising them are described herein, and may be used to immunise animals to generate antibodies against IL-18. Said IL-18, or one of its fragments, can especially be produced according to the usual working methods, by genetic recombination starting with a nucleic acid sequence contained in the cDNA sequence coding for IL-18 or fragment thereof, by peptide synthesis starting from a sequence of amino acids comprised in the peptide sequence of the IL-18 and/or fragment thereof.

The monoclonal antibodies can, for example, be purified on an affinity column on which IL-18 or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-Binding Site

This describes the part of a molecule that binds to and is complementary to all or part of the target antigen. In an antibody molecule, it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

WO 2006/072620 describes engineering of antigen binding sites in structural (non-CDR) loops extending between beta strands of immunoglobulin domains. An antigen binding site may be engineered in a region of an antibody molecule separate from the natural location of the CDRs, e.g. in a framework region of a VH or VL domain, or in an antibody constant domain e.g. CH1 and/or CH3. An antigen binding site engineered in a structural region may be additional to, or instead of, an antigen binding site formed by sets of CDRs of a VH and VL domain. Where multiple antigen binding sites are present in an antibody molecule, they may bind the same antigen (target antigen), thereby increasing valency of the binding member. Alternatively, multiple antigen binding sites may bind different antigens (the target antigen and one or more another antigen), and this may be used to add effector functions, prolong half-life or improve in vivo delivery of the antibody molecule.

Isolated

This refers to the state in which binding members of the invention, or nucleic acid encoding such binding members, will generally be in accordance with the present invention. Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising anti-IL-18 antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that 1, 2, 3, 4, 5, 6, 7, 8, 9, 10, 11, 12, 13, 14 or 15 amino acid substitutions may be made in the CDR and/or VH or VL domain.

As noted above, a binding member in accordance with the present invention modulates and may neutralise a biological activity of IL-18. As described herein, IL-18-binding members of the present invention may be optimised for neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated. Nevertheless, high potency binding members may also be obtained without optimisation, for example a high potency binding member may be obtained directly from an initial screen e.g. a biochemical neutralization assay. A "potency optimized" binding member refers to a binding member with an optimized potency of neutralization of a particular activity or downstream function of IL-18. Assays and potencies are described in more detail elsewhere herein. The present invention provides potency-optimized and/or non-optimized binding members, as well as methods for potency optimization from a selected binding member. The present invention thus allows the skilled person to generate binding members having high potency.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages, such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO92/01047 and e.g. U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404, each of which is herein incorporated by reference in their entirety. Ribosome display is described in Hanes J and Plückthun A. (1997) Proc Natl Acad Sci USA. 1997 May 13; 94(10):4937-42; WO01/75097 and WO2006/072773, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind IL-18 may be further tested, also ability to compete with e.g. any of the antibodies as listed herein (e.g. in scFv format and/or IgG format, e.g. IgG2 or IgG1) for binding to IL-18. Ability to neutralize IL-18 may be tested, as discussed further elsewhere herein.

A binding member may bind IL-18 with the affinity of any of the antibodies listed in Tables 10 and 11, e.g. scFv, IgG2, IgG1TM or IgG1, or with an affinity that is better. Antibody binding affinities are shown in Table 5.

A binding member may neutralise a biological activity of IL-18 with the potency of any of the antibodies listed herein e.g. scFv, IgG2 IgG1, or with an increased potency.

Binding affinity and neutralization potency of different binding members can be compared under appropriate conditions.

Variants of the VH and VL domains and CDRs described herein, including those for which amino acid sequences are set out herein, and which can be employed in binding members for IL-18 can be obtained by means of methods of sequence alteration or mutation and screening for antigen binding members with desired characteristics. Examples of desired characteristics include but are not limited to
  Increased binding affinity for antigen relative to known antibodies which are specific for the antigen
  Increased neutralization of an antigen activity relative to known antibodies which are specific for the antigen if the activity is known
  Specified competitive ability with a known antibody or ligand to the antigen at a specific molar ratio
  Ability to immunoprecipitate complex
  Ability to bind to a specified epitope
    Linear epitope, e.g. peptide sequence identified using peptide-binding scan as described herein, e.g. using peptides screened in linear and/or constrained conformation
    Conformational epitope, formed by non-continuous residues Ability to modulate a new biological activity of IL-18, or downstream molecule.

Such methods are also provided herein.

Variants of antibody molecules disclosed herein may be produced and used in the present invention. Following the lead of computational chemistry in applying multivariate data analysis techniques to the structure/property-activity relationships [see for example, Wold, et al. Multivariate data analysis in chemistry. Chemometrics-Mathematics and Statistics in Chemistry (Ed.: B. Kowalski); D. Reidel Publishing Company, Dordrecht, Holland, 1984 (ISBN 90-277-1846-6] quantitative activity-property relationships of antibodies can be derived using well-known mathematical techniques, such as statistical regression, pattern recognition and classification [see for example Norman et al. Applied Regression Analysis. Wiley-Interscience; $3^{rd}$ edition (April 1998) ISBN: 0471170828; Kandel, Abraham et al. Computer-Assisted Reasoning in Cluster Analysis. Prentice Hall PTR, (May 11, 1995), ISBN: 0133418847; Krzanowski, Wojtek. Principles of Multivariate Analysis: A User's Perspective (Oxford Statistical Science Series, No 22 (Paper)). Oxford University Press; (December 2000), ISBN: 0198507089; Witten, Ian H. et al Data Mining: Practical Machine Learning Tools and Techniques with Java Implementations. Morgan Kaufmann; (Oct. 11, 1999), ISBN: 1558605525; Denison David G. T. (Editor) et al Bayesian Methods for Nonlinear Classification and Regression (Wiley Series in Probability and Statistics). John Wiley & Sons; (July 2002), ISBN: 0471490369; Ghose, Arup K. et al. Combinatorial Library Design and Evaluation Principles, Software, Tools, and Applications in Drug Discovery. ISBN: 0-8247-0487-8]. The properties of antibodies can be derived from empirical and theoretical models (for example, analysis of likely contact residues or calculated physicochemical property) of antibody sequence, functional and three-dimensional structures and these properties can be considered individually and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [Chothia C. et al. Journal Molecular Biology (1992) 227, 799-817; Al-Lazikani, et al. Journal Molecular Biology (1997) 273(4), 927-948]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule [Chothia, et al. Science, 223, 755-758 (1986)] using any freely available or commercial package, such as WAM [Whitelegg, N. R. u. and Rees, A. R (2000). Prot. Eng., 12, 815-824]. A protein visualisation and analysis software package, such as Insight II (Accelrys, Inc.) or Deep View [Guex, N. and Peitsch, M. C. Electrophoresis (1997) 18, 2714-2723] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize IL-18 and/or for any other desired property.

Variable domain amino acid sequence variants of any of the VH and VL domains whose sequences are specifically disclosed herein may be employed in accordance with the present invention, as discussed.

As described above, aspects of the invention provide a binding member, such as an antibody molecule, comprising a VH domain that has at least 75%, at least 80%, at least 85%, at least 90%, at least 93%, at least 95%, at least 96%, at least 95%, at least 97%, at least 98% or at least 99% amino acid sequence identity with a VH domain of any of the antibodies listed herein, for which VH domain sequences are shown in the appended sequence listing below; and/or comprising a VL domain that has at least 75%, at least 80%, at least 85%, at least 90%, at least 93%, at least 95%, at least 96%, at least 95%, at least 97%, at least 98% or at least 99% amino acid sequence identity with a VL domain of any of the antibodies listed in Table 11, for which VL domain sequences are shown in the appended sequence listing.

Aspects of the invention provide a binding member, such as an antibody molecule, comprising a VH domain having a set of VH CDRs that have at least 75%, at least 80%, at least 85%, at least 90%, at least 93%, at least 95%, at least 96%, at least 95%, at least 97%, at least 98% or at least 99% amino acid sequence identity with the set of VH CDRs of any of the antibodies listed herein, for which VH CDR sequences are shown herein; and/or comprising a VL domain having a set of VL CDRs that have at that has at least 75%, at least 80%, at least 85%, at least 90%, at least 93%, at least 95%, at least 96%, at least 95%, at least 97%, at least 98% or at least 99% amino acid sequence identity with the set of VL CDRs of any of the antibodies listed herein, for which the VL CDR sequences are shown in herein.

Algorithms that can be used to calculate % identity of two amino acid sequences include e.g. BLAST [Altschul et al. (1990) J. Mol. Biol. 215: 405-410], FASTA [Pearson and Lipman (1988) PNAS USA 85: 2444-2448], or the Smith-Waterman algorithm [Smith and Waterman (1981) J. Mol Biol. 147: 195-197] e.g. employing default parameters.

Particular variable domains may include one or more amino acid sequence alterations (substitution, deletion, and/or insertion of an amino acid residue), and less than about 15 14, 13, 12, 11, 10, 9, 8, 7, 6, 5, 4, 3 or 2.

Alterations may be made in one or more framework regions and/or one or more CDRs. The alterations normally do not result in loss of function, so a binding member comprising a thus-altered amino acid sequence may retain an ability to bind and/or neutralize IL-18. It may retain the same quantitative binding and/or neutralizing ability as a binding member in which the alteration is not made, e.g. as measured in an assay described herein. The binding member comprising a thus-altered amino acid sequence may have an improved ability to bind and/or neutralize IL-18.

Alteration may comprise replacing one or more amino acid residues with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [Voet & Voet, *Biochemistry*, 2nd Edition, (Wiley) 1995]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired IL-18-binding and neutralizing properties in a binding member of the invention. Additionally, D-amino acids and analogues have been shown to have different pharmacokinetic profiles compared with standard L-amino acids, owing to in vivo degradation of polypeptides having L-amino acids after administration to an animal e.g. a human, meaning that D-amino acids are advantageous for some in vivo applications.

Novel VH or VL regions carrying CDR-derived sequences of the invention may be generated using random mutagenesis of one or more selected VH and/or VL genes to generate mutations within the entire variable domain. Such a technique is described by Gram et al. [Gram et al., 1992, *Proc. Natl. Acad. Sci., USA*, 89:3576-3580], who used error-prone PCR. In some embodiments one or two amino acid substitutions are made within an entire variable domain or set of CDRs.

Another method that may be used is to direct mutagenesis to CDR regions of VH or VL genes. Such techniques are disclosed by Barbas et al. [Barbas et al., 1994, *Proc. Natl. Acad. Sci., USA*, 91:3809-3813] and Schier et al. [Schier et al., 1996, *J. Mol. Biol.* 263:551-567].

All the above-described techniques are known as such in the art and the skilled person will be able to use such techniques to provide binding members of the invention using routine methodology in the art.

A further aspect of the invention provides a method for obtaining an antibody antigen-binding site for IL-18, the method comprising providing by way of substitution, deletion, or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a binding member or an antibody antigen-binding site for IL-18 and optionally with one or more desired properties, e.g. ability to neutralize IL-18 activity. Said VL domain may have an amino acid sequence which is substantially as set out herein. An analogous method may be employed in which one or more sequence variants of a VL domain disclosed herein are combined with one or more VH domains.

As noted above, a CDR amino acid sequence substantially as set out herein may be incorporated as a CDR in a human antibody variable domain or a substantial portion thereof. The HCDR3 sequences substantially as set out herein represent embodiments of the present invention and each of these may be incorporated as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. [Marks et al *Bio/Technology*, 1992, 10:779-783] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system, such as the phage display system of WO92/01047, which is herein incorporated by reference in its entirety, or any of a subsequent large body of literature, including Kay, Winter & McCafferty [Kay, B. K., Winter, J., and McCafferty, J. (1996) Phage Display of Peptides and Proteins: A Laboratory Manual, San Diego: Academic Press], so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members or more. Other suitable host systems include, but are not limited to yeast display, bacterial display, T7 display, viral display, cell display, ribosome display and covalent display.

A method of preparing a binding member for IL-18 is provided, which method comprises:
(a) providing a starting repertoire of nucleic acids encoding a VH domain which either include a CDR3 to be replaced or lack a CDR3 encoding region;
(b) combining said repertoire with a donor nucleic acid encoding an amino acid sequence substantially as set out herein for a VH CDR3, for example a VH CDR3 shown in Table 11, such that said donor nucleic acid is inserted into the CDR3 region in the repertoire, so as to provide a product repertoire of nucleic acids encoding a VH domain;
(c) expressing the nucleic acids of said product repertoire;
(d) selecting a binding member for IL-18; and
(e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for IL-18.

For example, an HCDR1, HCDR2 and/or HCDR3, e.g. a set of HCDRs, from one or more of the antibodies listed in Table 11 may be employed, and/or an LCDR1, LCDR2 and/or LCDR3, e.g. set of LCDRs, from one or more of the antibodies listed herein may be employed.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind IL-18. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques, such as those described in that reference. This technique is also disclosed in Marks et al Bio/Technology, 1992, 10:779-783.

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG2, IgG1 and IgG4. IgG2 may be advantageous in some embodiments owing to its lack of effector functions. In other embodiments, IgG1 may be advantageous due to its effector function and ease of manufacture. Any synthetic or other constant region variant that has these properties and stabilizes variable regions may also be useful in the present invention.

Binding members may be labelled with a detectable or functional label. Thus, a binding member or antibody molecule can be present in the form of an immunoconjugate so as to obtain a detectable and/or quantifiable signal. An immunoconjugate may comprise an antibody molecule of the invention conjugated with detectable or functional label. A label can be any molecule that produces or can be induced to produce a signal, including but not limited to fluorescent labels, radiolabels, enzymes, chemiluminesent labels or photosensitizers. Thus, binding may be detected and/or measured by detecting fluorescence or luminescence, radioactivity, enzyme activity or light absorbance.

Suitable labels include, by way of illustration and not limitation, enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase e.g. horseradish peroxidase;

dyes;

fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and C is Biointernational), chemoluminescent labels or chemiluminescers, such as isoluminol, luminol and the dioxetanes;

bio-luminescent labels, such as luciferase and luciferin;

sensitizers;

coenzymes;

enzyme substrates;

radiolabels including but not limited to bromine$^{77}$, carbon$^{14}$, cobalt$^{57}$, fluorine$^{8}$, gallium$^{67}$, gallium$^{68}$, hydrogen$^{3}$ (tritium), indium$^{111}$, indium$^{113m}$, iodine$^{123m}$, iodine$^{125}$, iodine$^{126}$, iodine$^{131}$, iodine$^{133}$, mercury$^{107}$, mercury$^{203}$, phosphorous$^{32}$, rhenium$^{99m}$, rhenium$^{101}$, rhenium$^{105}$, ruthenium$^{95}$, ruthenium$^{97}$, ruthenium$^{103}$, ruthenium$^{105}$, scandium$^{47}$, selenium$^{75}$, sulphur$^{35}$, technetium$^{99}$, technetium$^{99m}$, tellurium$^{121m}$, tellurium$^{122m}$, tellurium$^{125m}$, thulium$^{165}$, thulium$^{167}$, thulium$^{168}$, yttrium$^{199}$ and other radiolabels mentioned herein;

particles, such as latex or carbon particles; metal sol; crystallite; liposomes; cells, etc., which may be further labelled with a dye, catalyst or other detectable group;

molecules such as biotin, digoxygenin or 5-bromodeoxyuridine;

toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Examples of suitable enzymes and coenzymes are disclosed in U.S. Pat. No. 4,275,149, and U.S. Pat. No. 4,318, 980. Suitable fluorescers and chemiluminescers are also disclosed in U.S. Pat. No. 4,275,149. Labels further include chemical moieties, such as biotin that may be detected via binding to a specific cognate detectable moiety, e.g. labelled avidin or streptavidin. Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known in the art for coupling the therapeutic radioisotopes to the antibodies either directly or via a chelating agent, such as EDTA, DTPA mentioned above may also be used for the radioelements which can be used in diagnosis. It is likewise possible to perform labelling with sodium$^{125}$ by the chloramine T method [Hunter W. M. and Greenwood F. C. (1962) Nature 194:495] or else with technetium$^{99m}$ by the technique of U.S. Pat. No. 4,424,200) or attached via DTPA as described in U.S. Pat. No. 4,479,930.

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternatively, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in U.S. Pat. No. 5,185,243.

An aspect of the invention provides a method comprising causing or allowing binding of a binding member as provided herein to IL-18. As noted, such binding may take place in vivo, e.g. following administration of a binding member, or nucleic acid encoding a binding member, or it may take place in vitro, for example in ELISA, Western blotting, immunocytochemistry, immunoprecipitation, affinity chromatography, and biochemical or cell-based assays, such as an KG-1 or PBMC cell assay.

The present invention also provides for measuring levels of antigen directly, by employing a binding member according to the invention for example in a biosensor system. For instance, a method of detecting and/or measuring binding to IL-18 may comprise, (i) exposing said binding member to IL-18 and (ii) detecting binding of said binding member to IL-18, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

In some embodiments, IL-18 which is bound by the binding member may be free IL-18 (i.e. IL-18 which is not bound to IL-18BP). Free IL-18 is the biologically active form of IL-18.

The amount of binding of the binding member to IL-18 may be determined. Quantitation may be related to the amount of the antigen in a test sample, which may be of diagnostic interest. Screening for IL-18 binding and/or the quantitation thereof may be useful, for instance, in screening patients for diseases or disorders referred to herein and/or any other disease or disorder involving aberrant IL-18 expression and/or activity.

A diagnostic method may comprise (i) obtaining a tissue or fluid sample from a subject, (ii) exposing said tissue or fluid sample to one or more binding members of the present invention; and (iii) detecting bound IL-18 as compared with a control sample, wherein an increase in the amount of IL-18 binding as compared with the control may indicate an aberrant level of IL-18 expression or activity. Tissue or fluid samples to be tested include blood, serum, urine, biopsy material, tumours, or any tissue suspected of containing aberrant IL-18 levels. Subjects testing positive for aberrant IL-18 levels or activity may also benefit from the treatment methods disclosed later herein.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are colored, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

Isolated binding members for interleukin-18 (IL-18) as described herein may compete with IL-18BP for binding to IL-18 and may therefore be useful in discriminating between IL-18 which is bound to IL-BP and free IL-18 (i.e. IL-18 which is not bound to IL-18 BP).

Isolated binding members of the invention may be useful in the detection and/or measurement of free IL-18. A method of detecting and/or measuring free IL-18 may comprise (i) exposing a binding member according to the invention to free IL-18 and (ii) detecting and/or measuring binding of said binding member to free IL-18. Binding of the binding member to free IL-18 may be detected and/or measured using any convenient method, for example, a method described herein.

Methods of the invention may be useful in determining the amount of free IL-18 in a sample.

A method of measuring free IL-18 in a sample may comprise;
 contacting a sample with a binding member of the invention and
 determining the binding of the binding member to the sample.

Binding of the binding member to the sample is indicative of the presence of free IL-18 in the sample. The amount of binding of the binding member to the sample may be indicative of the amount of free IL-18 in the sample.

A assay may involve the use of a first binding member with binds IL-18 and a second binding member, which also binds IL-18 but which binds to a different epitope on IL-18 than the first binding member. One of the first or second binding members is a binding member of the invention, the other of the first or second binding members may be a known IL-18 binding member, such as an anti-IL-18 antibody. Suitable known IL-18 binding members are available in the art.

In some convenient assay formats, one of said first or said second binding members may be immobilised on a solid substrate and the other non-immobilised.

A binding member may be immobilised to the solid support in a number of different ways known in the art. For example, the binding member may be adsorbed directly to the solid support, e.g. through electrostatic and/or hydrophobic interactions, such as in the case of plastic solid supports. Alternatively, the binding member may be covalently attached to the solid support. In this case, the solid support may be chemically modified to introduce or activate functional chemical groups on the surface of the support, such as hydroxyl or amine groups, and the support crosslinked using crosslinking agents such as gluteraldehyde, to facilitate covalent binding of the first member to the solid support. In a further alternative, the binding member may be indirectly attached to the solid support by a specific binding interaction, for example by an interaction between biotin and avidin, or by immobilising protein A or protein G to the solid support followed by specific binding to the binding member itself.

Many different assay formats suitable for detecting free IL-18 are known in the art, including non-competitive and competitive assays and immunoassays.

Non-competitive assay formats may involve, for example, immobilising the first binding member which binds IL-18 at a solid support. The immobilised binding member may then be brought into contact with a sample of interest. If the sample contains IL-18, it will bind with the immobilised binding member. The second binding member which binds IL-18 is then added and allowed to bind. In some embodiments, the immobilised first binding member may be a binding member of the invention. In other embodiments, the second binding member may be a binding member of the invention.

To allow detection, the second binding member may be labelled with a detectable label. Alternatively, binding of the second binding member may be determined using a third binding member, such as an antibody, which specifically binds to the second binding member and is labelled with a detectable label. Free IL-18 molecules in the sample are captured by the immobilised first binding member and thereby immobilised at the support. Second binding member binds to the captured free IL-18 and is itself immobilised at the support. In some embodiments, labelled third binding member may bind to the second binding member and also be immobilised at the support.

The third binding member may, for example, directly bind to the second binding member (e.g. an anti-IgG antibody) or may bind to an affinity tag which is linked or fused to the second binding member.

Suitable affinity tags include biotin or peptidyl sequences, such as MRGS(H)$_6$, DYKDDDDK (FLAG™), T7-, S-(KETAAAKFERQHMDS), poly-Arg (R5-6), poly-His (H2-10), poly-Cys (C4) poly-Phe(F11) poly-Asp(D5-16), Strept-tag II (WSHPQFEK), c-myc (EQKLISEEDL), Influenza-HA tag (Murray, P. J. et al (1995) Anal Biochem 229, 170-9), Glu-Glu-Phe tag (Stammers, D. K. et al (1991) FEBS Lett 283, 298-302), Tag.100 (Qiagen; 12 aa tag derived from mammalian MAP kinase 2), Cruz tag 09™ (MKAEFRRQESDR, Santa Cruz Biotechnology Inc.) and Cruz tag 22™ (MRDALDRLDRLA, Santa Cruz Biotechnology Inc.).

The amount of labelled second or third binding member bound directly or indirectly to the solid support is then measured, whereby the amount of labelled binding member detected is directly proportional to the amount of free IL-18 present in the sample.

For example, a method of measuring free IL-18 in a sample may comprise;
 contacting the sample with a first binding member with binds IL-18, and;
 determining binding of said first binding member to IL-18 in the sample using a second binding member with binds IL-18,
 wherein one of said first or second binding members is a binding member of the invention and the other of said first or second binding members is an anti-IL-18 binding member which does not compete with a binding member of the invention for binding to IL-18.

As described above, the first binding member may be a binding member of the invention and the second binding member may be an anti-IL-18 binding member which does not compete with a binding member of the invention for binding to IL-18; or the second binding member may be a binding member of the invention and the first binding member may be an anti-IL-18 binding member which does not compete with a binding member of the invention for binding to IL-18.

Competitive assays to determine the presence of free IL-18 in a sample of interest may involve immobilising a binding member of the invention at a solid support. Labelled IL-18 is then added and allowed to bind to the immobilized binding member of the invention, followed by addition of the sample. If the sample contains free IL-18, it will compete with the labelled IL-18 for binding to the immobilized binding member of the invention. The amount of labelled IL-18 bound to the solid support is then measured. In this case, the amount of labelled IL-18 which is detected is inversely proportional to the amount of free IL-18 present in the sample.

Suitable samples include samples of biological fluid, such as cerebrospinal fluid (CSF), bile, urine, sebum, sputum or serum. Samples may be obtained from individuals, for example primates such as humans or monkeys, using standard techniques.

A detectable label as referred to herein may be any label which produces or can be induced to produce a signal, including but not limited to fluorescers, chemiluminescers (e.g. horseradish peroxidase), coloured labels (e.g. latex [blue] or colloidal gold [red]), radiolabels, enzymes, and magnetic labels. The amount of label bound at a surface, e.g. a surface of a capillary bore, may therefore be detected and/or measured by detecting fluorescence or luminescence, colour, radioactivity, enzyme activity, or changes in magnetic field. Detectable labels may be attached to binding members using conventional chemistry. Preferably, a detectable label is a label detectable by optical interrogation, e.g. with a digital camera or flatbed scanner. Labels that can be detected by optical interrogation include fluorescers, chemiluminescers and coloured labels. The mechanism by which a signal can be generated for optical detection includes (but is not necessarily limited to): light absorption, light scattering, light diffraction, light reflection, fluorescence or luminescence.

Measurement of free IL-18 as described herein allows the levels of biologically active IL-18 to be accurately determined in a sample.

Measurement of free IL-18 may be useful in the diagnosis and/or prognosis of disease conditions, including inflammatory diseases, autoimmune diseases such as secondary haemophagocytic syndrome, macrophage activation syndrome, rheumatoid arthritis, and type I diabetes, and cardiovascular diseases, for example coronary diseases, such as chronic obstructive pulmonary disease (COPD) and acute coronary syndrome.

Measurement of free IL-18 may also be useful in assessing the responsiveness of a disease condition to treatment.

A method for assessing the responsiveness of a disease condition in an individual to treatment may comprise:
measuring the amount of free IL-18 in samples obtained from the individual before and after said treatment using a binding member of the invention, as described above, wherein a decrease in the level of free IL-18 is indicative that the individual is responsive to the treatment.

The level or amount of free IL-18 may be measured in a first sample obtained from the individual before said administration using a binding member of the invention as described herein and in a second sample obtained from the individual after said administration, a difference, for example a decrease, between the level or amount of free IL-18 in the first and second samples being indicative that the disease condition is responsive to said treatment.

A method for monitoring the treatment of a disease condition in individual may comprise:
(a) subjecting the individual to a regimen of treatment; and
(b) monitoring in samples obtained from the individual the level or amount of free IL-18 using a method described above during said treatment,
wherein a reduction in the level or amount of free IL-18 in samples obtained during the treatment is indicative that the regimen is effective for treating the disease condition in the individual.

In the absence of sustained changes in the level or amount of free IL-18 in samples obtained from the patient during the treatment, the method may further comprise;

(c) altering the regimen of treatment and subjecting the individual to the altered regimen;
(d) monitoring the level of free IL-18 in samples obtained from the individual using a method described herein, and
(e) repeating steps c) and d) until a sustained change in the level of free IL-18 is observed.
wherein a change in the level or amount of free IL-18 which is sustained during the treatment, for example a reduction, is indicative that the altered regimen is effective for treating the disease condition in the individual.

In the presence of sustained changes in the level or amount of free IL-18 during the treatment, the method may further comprise;

(c) altering the regimen of treatment and subjecting the individual to the altered regimen;
(d) monitoring the level of free IL-18 in samples obtained from the individual using a method described herein, and
(e) repeating steps c) and d) until a maximal change in the level of free IL-18 is observed.
wherein a maximal change in the level or amount of free IL-18 which is sustained during the treatment is indicative that the altered regimen is effective for treating the disease condition in the individual.

Measurement of free IL-18 may also be useful in identifying a cohort of patients for clinical trials.

A method for identifying a cohort of patients may comprise:
(a) identifying a population of patients having a disease condition
(b) measuring the amount of free IL-18 in samples obtained from the patients in the population using a binding member of the invention as described above;
(c) identifying samples containing an amount of free IL-18 which is above or below a threshold value, and;
(d) identifying from the identified samples a cohort of patients.

The identified cohort of patients may all have high or low levels of free IL-18 (i.e. levels above or below the threshold value).

Disease conditions may included inflammatory and autoimmune diseases such as secondary haemophagocytic syndrome, macrophage activation syndrome, rheumatoid arthritis, and type I diabetes, and coronary diseases, such as chronic obstructive pulmonary disease (COPD) and acute coronary syndrome.

Suitable treatments which may be monitored and/or assessed in a patient as described above are well known in the art.

A kit comprising a binding member as described herein is also provided as an aspect of the present invention. In the kit, the binding member may be labelled to allow its reactivity in a sample to be determined, e.g. as described further below. Further, the binding member may or may not be attached to a solid support. Components of a kit are generally sterile and in sealed vials or other containers. Kits may be employed in diagnostic analysis or other methods for which binding members are useful. A kit may be for use in a method described above. A kit may contain instructions for use of the components in a method, e.g. a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

As described above, the present invention extends to a binding member that competes for binding to IL-18 with any binding member defined herein, e.g. any of the antibodies listed in Table 11, e.g. in IgG2, IgG1 or IgG1 triple mutation (TM; Oganesyan et al (2008) Acta Crystallogr D Biol Crystallogr. 64(Pt 6):700-4) format. Competition between binding members may be assayed easily in vitro, for example by tagging a specific reporter molecule to one binding member which can be detected in the presence of other untagged binding member(s), to enable identification of binding members which bind the same epitope or an overlapping epitope. Competition may be determined for example using ELISA in which IL-18 is immobilized to a plate and a first tagged or labelled binding member along with one or more other untagged or unlabelled binding members is added to the plate. Presence of an untagged binding member that competes with the tagged binding member is observed by a decrease in the signal emitted by the tagged binding member.

For example, the present invention includes a method of identifying a IL-18 binding compound, comprising (i) immobilizing IL-18 to a support, (ii) contacting said immobilized IL-18 simultaneously or in a step-wise manner with at least one tagged or labelled binding member according to the invention and one or more untagged or unlabelled test binding compounds, and (iii) identifying a new IL-18 binding compound by observing a decrease in the amount of bound tag from the tagged binding member. Such methods can be performed in a high-throughput manner using a multiwell or array format. Such assays may also be performed in solution (see, for instance, U.S. Pat. No. 5,814,468). As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

Competition assays can also be used in epitope mapping. In one instance epitope mapping may be used to identify the epitope bound by a IL-18 binding member which optionally may have optimized neutralizing and/or modulating characteristics. Such an epitope can be linear or conformational. A conformational epitope can comprise at least two different fragments of IL-18, wherein said fragments are positioned in proximity to each other when IL-18 is folded in its tertiary or quaternary structure to form a conformational epitope which is recognized by an inhibitor of IL-18, such as a IL-18-binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid sequence encoding a binding member described herein. Nucleic acid may include DNA and/or RNA. In one, the present invention provides a nucleic acid that encodes a CDR or set of CDRs or VH domain or VL domain or antibody antigen-binding site or antibody molecule, e.g. scFv or IgG (e.g. IgG2, IgG1 or IgG1), of the invention as defined above.

The present invention also provides constructs in the form of plasmids, vectors, transcription or expression cassettes which comprise at least one polynucleotide as above.

The present invention also provides a recombinant host cell line that comprises one or more constructs as above. A nucleic acid sequence encoding any CDR or set of CDRs or VH domain or VL domain or antibody antigen-binding site or antibody molecule, e.g. scFv or IgG (e.g. IgG2, IgG1 or IgG1TM) as provided, forms an aspect of the present invention, along with a method of production of the encoded product, which method comprises expression from encoding nucleic acid sequences thereof. Expression may conveniently be achieved by culturing recombinant host cells containing the nucleic acid under appropriate conditions. Following production by expression a VH or VL domain, or binding member may be isolated and/or purified using any suitable technique, then used as appropriate.

Nucleic acid sequences according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Another aspect provides a method of production of an antibody VH variable domain, the method including causing expression from encoding nucleic acid sequences. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun [Plückthun, A. Bio/Technology 9: 545-551 (1991)]. A common bacterial host is *E. coli*.

Expression in eukaryotic cells in culture is also available to those skilled in the art as an option for production of a binding member [Chadd H E and Chamow S M (2001) Current Opinion in Biotechnology 12: 188-194; Andersen D C and Krummen L (2002) Current Opinion in Biotechnology 13: 117; Larrick J W and Thomas D W (2001) Current Opinion in Biotechnology 12:411-418].

Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate [Sambrook and Russell, *Molecular Cloning: a Laboratory Manual:* 3rd edition, 2001, Cold Spring Harbor Laboratory Press]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [Ausubel et al. eds., *Short Protocols in Molecular Biology: A Compendium of Methods from Current Protocols in Molecular Biology*, John Wiley & Sons, $4^{th}$ edition 1999].

A further aspect of the present invention provides a host cell containing nucleic acid as disclosed herein. Such a host cell may be in vitro and may be in culture. Such a host cell may be in vivo. In vivo presence of the host cell may allow intra-cellular expression of the binding members of the present invention as "intrabodies" or intra-cellular antibodies. Intrabodies may be used for gene therapy.

Another aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

Binding members described herein may be used in methods of diagnosis or treatment in human or animal subjects, e.g. humans. Binding members for IL-18 may be used to treat disorders associated with IL-18 and/or disorders in which decreasing activity of IL-18 is of benefit.

Binding members for IL-18 may be used to decrease activity of IL-18 in an individual. Accordingly, the invention provides a method of decreasing activity of IL-18 in an individual comprising administering to an individual in need thereof an effective amount of one or more binding members of the present invention alone or in a combined therapeutic regimen with another appropriate medicament known in the art or described herein such that activity of IL-18 is decreased.

A binding member as described herein may be used in the treatment of the conditions listed below:

1. bone and joints: arthritides associated with or including osteoarthritis/osteoarthrosis, both primary and secondary to, for example, congenital hip dysplasia; cervical and lumbar spondylitis, and low back and neck pain; rheumatoid arthritis; Still's disease; seronegative spondyloarthropathies including ankylosing spondylitis; psoriatic arthritis; reactive arthritis; undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies, including dermatomyositits and polymyositis; polymalgia rheumatica; Kawasaki disease; juvenile arthritis including systemic juvenile idiopathic arthritis (sJIA) and idiopathic inflammatory arthritides of whatever joint distribution and associated syndromes; macrophage activation syndrome; rheumatic fever and its systemic complications; hemophagocytic syndrome; hemophagocytic lymphohystiocytosis; CAP syndrome; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever; Muckle-Wells syndrome; and Familial Hibernian Fever; Kikuchi disease; drug-induced arthalgias, tendonititides, and myopathies;

2. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

3. cardiovascular: renal ischaemia; stroke; atherosclerosis; arteriosclerosis; abdominal aortic aneurysm; peripheral artery disease; angina pectoris; acute coronary syndrome; myocardial infarction; congestive heart failure; restenosis following revascularization procedures; cerebrovascular disease including multi-infarct dementia; peripheral vessel diseases including erectile dysfunction; disorders affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

4. endrocrine disease: diabetes mellitus, including type 2 diabetes and diabetic complications such as diabetic nephropathy, neuropathy and retinopathy.

5. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

6. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

7. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

8. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

9. abdominal: hepatitis, including autoimmune, alcoholic and viral; fibrosis and cirrhosis of the liver; cholecystitis; pancreatitis, both acute and chronic;

10. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

11. allograft rejection: acute and chronic following, for example, transplantation of kidney, heart, liver, lung, bone marrow, skin or cornea or following blood transfusion; or chronic graft versus host disease;

12. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

13. other auto-immune and allergic disorders including Hashimoto's thyroiditis, Graves' disease, Addison's disease, idiopathic thrombocytopaenic purpura, eosinophilic fasciitis, hyper-IgE syndrome, antiphospholipid syndrome;

14. other disorders with an inflammatory or immunological component; including acquired immune deficiency syndrome (AIDS), leprosy, Sezary syndrome, and paraneoplastic syndromes.

15. cancers, including any type of metastatic or non metastatic solid cancer or malignant lymphoma, such as leukaemia, sarcomas, skin cancer, bladder cancer, breast cancer, uterus cancer, ovary cancer, prostate cancer, lung cancer, colorectal cancer, cervical cancer, liver cancer, head and neck cancer, oesophageal cancer, pancreas cancer, renal cancer, stomach cancer and cerebral cancer.

Binding members as described herein can be used to treat such disorders, including preventative treatment and reduction of severity of the disorder or one or more of its symptoms, or delaying or reducing risk of onset.

Accordingly, the invention provides a method of treating or reducing the severity of at least one symptom of any of the disorders mentioned herein, comprising administering to a patient in need thereof an effective amount of one or more binding members of the present invention alone or in a combined therapeutic regimen with another appropriate medicament known in the art or described herein such that the severity of at least one symptom of any of the above disorders is reduced.

Binding members of the invention may be used in animals and in animal models of disease, for example primate models, such as Rhesus or cynomolgus monkey models. Suitable animal models may also include immunocompromised non-human mammals, such as mice or rats, which have reconstituted with human cells.

Thus, binding members described herein are useful as therapeutic agents in the treatment of diseases or disorders involving IL-18, e.g. IL-18 expression and/or activity, especially aberrant expression/activity. A method of treatment may comprise administering an effective amount of a binding member described herein to a patient in need thereof, wherein aberrant expression and/or activity of IL-18 is decreased. A method of treatment may comprise (i) identifying a patient demonstrating aberrant IL-18 levels or activity, for instance using the diagnostic methods described above, and (ii) administering an effective amount of a binding member described herein to the patient, wherein aberrant expression and/or activity of IL-18 is decreased. An effective amount is an amount that decreases the aberrant expression and/or activity of IL-18 so as to decrease or lessen the severity of at least one symptom of the particular disease or disorder being treated, but not necessarily cure the disease or disorder.

The invention also provides a method of antagonising at least one effect of IL-18 comprising contacting with or administering an effective amount of one or more binding members of the present invention such that said at least one effect of IL-18 is antagonised. Effects of IL-18 that may be antagonised by the methods of the invention include binding to its receptor and/or to IL-18BP, and any downstream effects that arise as a consequence of these binding reactions.

Accordingly, further aspects of the invention provide methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient. A pharmaceutically acceptable excipient may be a compound or a combination of compounds entering into a pharmaceutical composition not provoking secondary reactions and which allows, for example, facilitation of the administration of the binding member, an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members as described herein will usually be administered in the form of a pharmaceutical composition, which may comprise at least one component in addition to the binding member. Thus pharmaceutical compositions according to the present invention, and for use in accordance with the present invention, may comprise, in addition to a binding member, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-articular, intra-vesicular or by injection, as discussed below.

Pharmaceutical compositions for oral administration, such as for example single domain antibody molecules (e.g. "Nanobodies™") etc are also envisaged in the present invention. Such oral formulations may be in tablet, capsule, powder, liquid or semi-solid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

For intra-venous injection, or injection at the site of affliction (e.g. intra-articular injection), the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members as described herein may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-IL-18 will depend upon the intended route of delivery: for example, formulations for pulmonary delivery may consist of particles with physical properties that ensure penetration into the deep lung upon inhalation; topical formulations may include viscosity modifying agents, which prolong the time that the drug is resident at the site of action. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art [Robinson, J. R. ed., Sustained and Controlled Release Drug Delivery Systems, Marcel Dekker, Inc., New York, 1978].

Anti-IL-18 treatment may be given orally (such as for example single domain antibody molecules (e.g. "Nanobodies™")) by injection (for example, subcutaneously, intra-articular, intra-venously, intra-peritoneal, intra-arterial or intra-muscularly), by inhalation, intra-tracheal, by the intra-vesicular route (instillation into the urinary bladder), or topically (for example intra-ocular, intra-nasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. It is envisaged that anti-IL-18 treatment will not be restricted to use in the clinic. Therefore, subcutaneous injection using a needle-free device is also advantageous.

A composition may be administered alone or in combination with other treatments, either simultaneously or sequentially dependent upon the condition to be treated.

A binding member for IL-18 may be used as part of a combination therapy in conjunction with an additional medicinal component. Combination treatments may be used to provide significant synergistic effects, particularly the combination of an anti-IL-18 binding member with one or more other drugs. A binding member for IL-18 may be administered concurrently or sequentially or as a combined preparation with another therapeutic agent or agents, for the treatment of one or more of the conditions listed herein.

A binding member according to the present invention may be provided in combination or addition with one or more of the following agents:

- a cytokine or agonist or antagonist of cytokine function (e.g. an agent which acts on cytokine signalling pathways, such as a modulator of the SOCS system), such as an alpha-, beta- and/or gamma-interferon; insulin-like growth factor type I (IGF-1), its receptors and associated binding proteins; interleukins (IL), e.g. one or more of IL-1 to IL-37, and/or an interleukin antagonist or inhibitor, such as anakinra; inhibitors of receptors of interleukin family members or inhibitors of specific subunits of such receptors, (for example tocilizumab (Actemra™; Roche) a humanised IgG1 monoclonal antibody against the human IL-6 receptor), a tumour necrosis factor alpha (TNF-α) inhibitor, such as an anti-TNF monoclonal antibodies (for example infliximab, adalimumab and/or CDP-870) and/or a TNF receptor antagonist, e.g. an immunoglobulin molecule (such as etanercept) and/or a low-molecular-weight agent, such as pentoxyfylline;
- a modulator of B cells, e.g. a monoclonal antibody targeting B-lymphocytes (such as CD20 (rituximab) or MRA-aIL16R) or T-lymphocytes (e.g. CTLA4-Ig, HuMax Il-15 or Abatacept);
- a modulator that inhibits osteoclast activity, for example an antibody to RANKL;
- a modulator of chemokine or chemokine receptor function, such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 and CXCR6 (for the C—X—C family) and $CX_3CR1$ for the C—$X_3$—C family;
- an inhibitor of matrix metalloproteases (MMPs), i.e. one or more of the stromelysins, the collagenases and the gelatinases as well as aggrecanase, especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, e.g. an agent such as doxycycline;
- a leukotriene biosynthesis inhibitor, 5-lipoxygenase (5-LO) inhibitor or 5-lipoxygenase activating protein (FLAP) antagonist, such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound, such as L-739,010; a 2-cyanoquinoline compound, such as L-746,530; indole and/or a quinoline compound, such as MK-591, MK-886 and/or BAY x 1005;
- a receptor antagonist for leukotrienes (LT) B4, LTC4, LTD4, and LTE4, selected from the group consisting of the phenothiazin-3-1s, such as L-651,392; amidino compounds, such as CGS-25019c; benzoxalamines, such as ontazolast; benzenecarboximidamides, such as BIIL 284/260; and compounds, such as zafirlukast, ablukast, montelukast, pranlukast, verlukast (MK-679), RG-12525, Ro-245913, iralukast (CGP 45715A) and BAY x 7195;
- a phosphodiesterase (PDE) inhibitor, such as a methylxanthanine, e.g. theophylline and/or aminophylline; and/or a selective PDE isoenzyme inhibitor, e.g. a PDE4 inhibitor and/or inhibitor of the isoform PDE4D and/or an inhibitor of PDE5;
- a histamine type 1 receptor antagonist, such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);
- a proton pump inhibitor (such as omeprazole) or gastroprotective histamine type 2 receptor antagonist;
- an antagonist of the histamine type 4 receptor;
- an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride;
- an anticholinergic agent, e.g. a muscarinic receptor (M1, M2, and M3) antagonist, such as atropine, hyoscine, glycopyrrrolate, ipratropium bromide, tiotropium bromide, oxitropium bromide, pirenzepine and telenzepine;
- a beta-adrenoceptor agonist (including beta receptor subtypes 1-4), such as isoprenaline, salbutamol, formoterol, salmeterol, terbutaline, orciprenaline, bitolterol mesylate and/or pirbuterol, e.g. a chiral enantiomer thereof;
- a chromone, e.g. sodium cromoglycate and/or nedocromil sodium;
- a PDE-4 inhibitor, such as roflumilast
- a glucocorticoid, such as flunisolide, triamcinolone acetonide, beclomethasone dipropionate, budesonide, fluticasone propionate, ciclesonide, and/or mometasone furoate;
- an agent that modulate nuclear hormone receptors, such as a PPAR;
- an immunoglobulin (Ig) or Ig preparation or an antagonist or antibody modulating Ig function, such as anti-IgE (e.g. omalizumab);
- other systemic or topically-applied anti-inflammatory agent, e.g. thalidomide or a derivative thereof, a retinoid, dithranol and/or calcipotriol;
- combinations of aminosalicylates and sulfapyridine, such as sulfasalazine, mesalazine, balsalazide, and olsalazine; and immunomodulatory agents, such as the thiopurines; and corticosteroids, such as budesonide;
- an antibacterial agent, e.g. a penicillin derivative, a tetracycline, a macrolide, a beta-lactam, a fluoroquinolone, metronidazole and/or an inhaled aminoglycoside; and/or an antiviral agent, e.g. acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a non-nucleoside reverse transcriptase inhibitor, such as nevirapine or efavirenz; or an antibody, such as palivizumab (Synagis™)
- a cardiovascular agent, such as a thiazide or loop diuretic; vasodilating agent such as nitroglycerin, calcium channel blocker, alpha-adrenoceptor blocker, beta-adrenoceptor blocker or combined alpha and beta-adrenoceptor blocker, angiotensin-converting enzyme (ACE) inhibitor, angiotensin-2 receptor antagonist; aldosteron antagonist or potassium sparing diuretic; lipid lowering agent, such as a statin, cholesterol absorption inhibitor and/or fibrate; a modulator of blood cell morphology, such as pentoxyfylline; a thrombolytic and/or an anticoagulant, e.g. a platelet aggregation inhibitor;
- a CNS agent, such as an antidepressant (such as sertraline), anti-Parkinsonian drug (such as deprenyl, L-dopa, ropinirole, pramipexole; MAOB inhibitor, such as selegine and rasagiline; comP inhibitor, such as tasmar; A-2 inhibitor, dopamine reuptake inhibitor, NMDA antagonist, nicotine agonist, dopamine agonist and/or inhibitor of neuronal nitric oxide synthase) and an anti-Alzheimer's drug, such as donepezil, rivastigmine, tacrine, COX-2 inhibitor, propentofylline or metrifonate;

an agent for the treatment of acute and chronic pain, e.g. a centrally or peripherally-acting analgesic, such as an opioid analogue or derivative, carbamazepine, phenyloin, sodium valproate, amitryptiline or other antidepressant agent, paracetamol, or non-steroidal anti-inflammatory agent;

a parenterally or topically-applied (including inhaled) local anaesthetic agent, such as lignocaine or an analogue thereof;

an anti-osteoporosis agent, e.g. a hormonal agent, such as raloxifene, or a biphosphonate, such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor, e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase, such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-$B_1$.- and/or $B_2$.- receptor antagonist; (x) an anti-gout agent, e.g. colchicine; (xi) a xanthine oxidase inhibitor, e.g. allopurinol; (xii) a uricosuric agent, e.g. probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g. basic fibroblast growth factor (bFGF); (xvii) granulocyte macrophage colony stimulating factor (GM-CSF); (xviii) capsaicin cream; (xix) a tachykinin NK.sub1. and/or NK.sub3. receptor antagonist, such as NKP-608C, SB-233412 (talnetant) and/or D-4418; (xx) an elastase inhibitor, e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells (such as a CRTH2 antagonist); (xxiv) an inhibitor of a P38 (xxv) agent modulating the function of Toll-like receptors (TLR) (xxvi) an agent modulating the activity of purinergic receptors, such as P2x7; (xxvii) an inhibitor of transcription factor activation, such as NFkB, API, and/or STATS or (xxviii) a caspase inhibitor, such as Boc-Asp-FMK, z-VAD-FMK, YVAD-FMK, Ac-WEHD-CHO, Ac-DEVD-CHO, Ac-YVADCHO, t-butoxycarbonyl-IETD-CHO, and t-butoxycarbonyl-AEVD-CHO.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent or another tyrosine kinase inhibitor in co-administration or in the form of an immunoconjugate. Fragments of said antibody could also be use in bispecific antibodies obtained by recombinant mechanisms or biochemical coupling and then associating the specificity of the above described antibody with the specificity of other antibodies able to recognize other molecules involved in the activity for which IL-18 is associated.

For treatment of an inflammatory disease, e.g. an inflammatory condition described above, such as rheumatoid arthritis, osteoarthritis, asthma, allergy, allergic rhinitis, chronic obstructive pulmonary disease (COPD), psoriasis, systemic lupus erythematosus, systemic juvenile idiopathic arthritis, autoimmune disease, acne, vasculitis, and Still's disease, a binding member of the invention may be combined with one or more agents, such as non-steroidal anti-inflammatory agents (hereinafter NSAIDs) including non-selective cyclo-oxygenase (COX)-1/COX-2 inhibitors whether applied topically or systemically, such as piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, such as phenylbutazone, salicylates, such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intra-muscular, intra-venous or intra-articular routes); methotrexate, leflunomide; hydroxychloroquine, d-penicillamine, auranofin or other parenteral or oral gold preparations; analgesics; diacerein; intra-articular therapies, such as hyaluronic acid derivatives; and nutritional supplements, such as glucosamine.

A binding member as described herein may also be used in combination with an existing therapeutic agent for the treatment of cancer. Suitable agents to be used in combination include:

(i) antiproliferative/antineoplastic drugs and combinations thereof, as used in medical oncology, such as Gleevec (imatinib mesylate), alkylating agents (for example cis-platin, carboplatin, cyclophosphamide, nitrogen mustard, melphalan, chlorambucil, busulphan and nitrosoureas); antimetabolites (for example antifolates, such as fluoropyrimidines like 5-fluorouracil and tegafur, raltitrexed, methotrexate, cytosine arabinoside, hydroxyurea, gemcitabine and paclitaxel); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents, such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase, such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI-1033)), for example inhibitors of the platelet-derived growth factor family and for example inhibitors of the hepatocyte growth factor family;

(v) antiangiogenic agents, such as those which inhibit the effects of vascular endothelial growth factor (for example the anti-vascular endothelial cell growth factor antibody bevacizumab, compounds, such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents, such as combretastatin A4 and compounds disclosed in International Patent Applications WO 99/02166, WO 00/40529, WO 00/41669, WO 01/92224, WO 02/04434 and WO 02/08213 (each of which is incorporated herein in its entirety);

(vii) antisense therapies, for example those which are directed to the targets listed above, such as ISIS 2503, an anti-ras antisense;

(viii) gene therapy approaches, including for example approaches to replace aberrant genes, such as aberrant p53 or aberrant BRCA1 or BRCA2, GDEPT (gene directed enzyme pro-drug therapy) approaches, such as those using cytosine deaminase, thymidine kinase or a bacterial nitroreductase enzyme and approaches to increase patient tolerance to chemotherapy or radiotherapy, such as multi-drug resistance gene therapy; and (ix) immunotherapeutic approaches, including for example ex vivo and in vivo approaches to increase the immunogenicity of patient tumour cells, such as transfection with cytokines, such as interleukin 2, interleukin 4 or granulocyte macrophage colony stimulating factor, approaches to decrease T-cell anergy, approaches using transfected immune cells, such as cytokine-transfected dendritic cells, approaches using cytokine-transfected tumour cell lines and approaches using anti-idiotypic antibodies.

A binding member for IL-18 and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

Compositions provided may be administered to mammals. Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody are well known in the art. Specific dosages indicated herein or in the Physician's Desk Reference (2005) as appropriate for the type of medicament being administered may be used. A therapeutically effective amount or suitable dose of a binding member of the invention can be determined by comparing its in vitro activity and in vivo activity in an animal model. Methods for extrapolation of effective dosages in test animals to humans are known. The precise dose will depend upon a number of factors, including whether the antibody is for diagnosis, prevention or for treatment, the size and location of the area to be treated, the precise nature of the antibody (e.g. whole antibody, fragment or diabody) and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment.

Various further aspects and embodiments of the present invention will be apparent to those skilled in the art in view of the present disclosure.

All documents, including database references and accession numbers, patents, patent applications and publications, mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the accompanying figures and tables.

EXAMPLES

Example 1

Anti-18 Antibody Generation and Lead Selection 1.1 Expression and Purification of Recombinant Human IL-18 Antigen Human IL-18 for bacterial expression (Uniprot entry Q14116-1; SEQ ID NO: 169) was cloned into a pET 21a vector (Novagen) and expressed in *E. coli* BL21 DE3*. The construct was generated in-house to include an N-terminal GST tag, histidine tag (8×His) together with a Factor Xa cleavage site. After soluble expression, the protein underwent purification using standard affinity chromatography, followed by Factor Xa cleavage and size exclusion purification to generate biologically active human IL-18.

For baculovirus expression of human IL-18, the construct was designed to have an N-terminal Flag tag and histidine tag. The construct was cloned into pDONR221 (Invitrogen, Paisley, UK) and transferred to destination vector pDEST8 (Invitrogen, Paisley, UK) for expression in insect cells, according to manufacturer's instructions. The protein was purified by standard affinity and size exclusion chromatography techniques.

The biotinylation of IL-18 was done via SH groups on free cysteines using the EZ-link Biotin-BMCC reagent (Thermo Fisher Scientific, Rochester N.Y.; cat. #21900).

1.2 Selections

Naïve human single chain Fv (scFv) phage display libraries cloned into a phagemid vector based on the filamentous phage M13 were used for selections (Vaughan et al (1996) Nature Biotechnology 14 (3):309-14; Lloyd et al (2009) Protein Eng Des Sel. (3):159-68; Hutchings et al (2001) Generation of Naive Human Antibody Libraries, in Antibody Engineering, Ed. by R. Kontermann & S. Dubel, Springer Laboratory Manuals, Berlin, p 93; Groves et al (2006) J Immunol Methods. 313(1-2):129-39). Anti-IL-18 specific scFv antibodies were isolated from the phage display libraries using a series of selection cycles on recombinant human IL-18 (Medical and Biological Laboratories Co., Nagoya, Japan) essentially as previously described by Vaughan et al ((1996) Nature Biotechnology 14 (3):309-14) and Hawkins et al ((1992) Journal of Molecular Biology 226, 889-896). In brief, for the first round of panning selections, human IL-18 in Dulbecco's phosphate buffer saline (DPBS, pH 7.4) was captured specifically by a rat anti-IL-18 monoclonal antibody, clone 159-12B (Medical and Biological Laboratories, Japan; cat. #D045-3) previously adsorbed onto wells of a Nunc™ maxisorp microtitre plate (Thermo Fisher Scientific, Rochester N.Y.; Cat. #439454) overnight at 4° C. Wells were washed with PBS then blocked for 1 hour with PBS-Marvel (3% w/v). Purified phage in PBS-Marvel (3% w/v), containing a 4 fold excess of capture antibody, rat anti-IL-18 monoclonal antibody, were added to the wells of a deselection plate (rat anti-IL-18 monoclonal antibody adsorbed onto wells of a maxisorp microtitre plate) for 1 hour before being allowed to bind coated antigen (recombinant human IL-18) for 1 hour. Unbound phage were removed by a series of wash cycles using PBS-Tween (0.1% v/v) and PBS. Bound phage particles were eluted, infected into *E. coli* TG1 bacteria and rescued for the next round of selection (Vaughan et al (1996) Nature Biotechnology 14(3):309-314). Round two selections were carried out in solution by incubating phage particles with 100 nM biotinylated IL-18 followed by a third round of rat anti-IL-18 monoclonal antibody capture selections as previously described.

1.3 Inhibition by Unpurified scFv of IL-18 Binding to IL-18 Receptor Alpha and Beta Chains Unpurified scFv from periplasmic preparations were screened in a homogeneous time-resolved fluorescence (HTRF™, Cis Bio International) receptor-ligand binding assay using an EnVision plate reader (PerkinElmer, Boston Mass.). Europium cryptate labelling of Human IL-18R alpha chain ([IL-18Rα]; R&D Systems, Minneapolis, Minn.; cat. #816-LR) was achieved using Trisbipyridine-Eu3+-cryptate-NHS (CIS bio International, Bagnols-sur-Ceze, France; cat. #65EUSABA) in PBS at pH 8 following the manufacturer's instructions. Human IL-18R beta chain ([IL-18Rβ]; R&D Systems, Minneapolis, Minn.; cat. #118-AP) was biotinylated via free amines using EZ link Sulfo-NHS-LC-Biotin (Thermo Fisher Scientific, Rochester N.Y.; cat. #21335) in PBS at pH 8. In the HTRF™ assay, unpurified scFv samples competed for the binding interaction of human recombinant IL-18 to its receptors, Europium cryptate labelled human IL-18Rα and biotinylated human IL-18Rβ. Selection outputs were screened as unpurified bacterial periplasmic extracts containing scFv, prepared in 50 mM MOPS buffer pH 7.4, 0.5 mM EDTA and 0.5 M sorbitol. Five microliters of unpurified scFv sample were added to a Costar® 384 well assay plate (Corning; Lowell, Mass.; cat. #77776-818). This was followed by the addition of 5 µl of 6 nM recombinant human IL-18 (in-house, *E. coli*-derived) and then 10 µl of a mixture containing 10 nM biotinylated IL-18Rβ, 2.5 nM Europium cryptate labelled IL-18Rα and 30 nM streptavidin Xlent! (C is Bio International, Bagnols-sur-Ceze, France; cat. #611SAXLB). Non-specific binding was determined using a control mouse monoclonal anti-human IL-18 antibody (Medical & Biological Laboratories Co., Nagoya, Japan; clone 125-2H) at 5 nM final concentration instead of periplasmic extracts. All dilutions were performed in PBS containing 0.4 M KF and 0.1% BSA (assay buffer). Assay plates were incubated for 4 hours at room temperature, prior to reading time resolved fluorescence by exciting the europium molecules at 320 nm and measuring the emission at 620 nm for the europium molecules and 665 nm emission wavelength for the XL665 molecules using an EnVision plate reader (Perkin Elmer, Waltham, Ma).

Data were analysed by calculating % Delta F values for each sample. Delta F was determined according to equation 1.

$$\% \text{ Delta } F = \frac{(\text{sample } 665 \text{ nm}/620 \text{ nm ratio value}) - (\text{non}-\text{specific control } 665 \text{ nm}/620 \text{ nm ratio value})}{(\text{non}-\text{specific control } 665 \text{ nm}/620 \text{ nm ratio value})} \times 100 \quad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

1.4 Inhibition by Purified scFv of IL-18 Binding to IL-18 Receptor Alpha and Beta Chains The ScFv extracts that showed a significant inhibitory effect on the IL-18 receptor alpha and receptor beta binding interaction as unpurified periplasmic extracts were subjected to DNA sequencing (Vaughan et al (1996) Nature Biotechnology 14: 309-314; Osbourn et al (1996) Immunotechnology. 2, 181-196). The scFv with unique sequences were expressed in *E. coli* and purified by affinity chromatography (as described by Bannister et al (2006) Biotechnology and bioengineering, 94. 931-937). The potency of av scFv was determined by testing a dilution series of the purified scFv in the HTRF™ assay described in section 1.3, substituting the unpurified scFv periplasmic preparation with the purified scFv.

Data were analysed by calculating % Delta F values and % Specific Binding as described in section 1.3. $IC_{50}$ values were determined using GraphPad Prism software by curve fitting using a four-parameter logistic equation (Equation 3).

$$Y = \text{Bottom} + (\text{Top} - \text{Bottom})/(1 + 10 \exp((\text{Log } EC50 - X)^* \text{HillSlope})) \quad \text{Equation 3}$$

X is the logarithm of concentration.
Y is specific binding

As illustrated in FIG. 1, purified scFv preparations of Antibody 1 inhibited the formation of the IL-18 receptor complex with an $IC_{50}$ value of 12 nM (n=1).

1.5 Reformatting of Antibody 1 scFv to IgG2

Antibody 1 scFv was reformatted to $IgG_2$ by subcloning the variable heavy chain (VH) and variable light chain (VL) domains into vectors expressing whole human antibody heavy and light chains respectively. The variable heavy chain was cloned into a mammalian expression vector (pEU9.2) containing the human heavy chain constant domains and regulatory elements to express whole $IgG_2$ heavy chain in mammalian cells. Similarly, the variable light chain domain was cloned into a mammalian expression vector (pEU3.4) for the expression of the human kappa light chain constant domains and regulatory elements to express whole IgG light chain in mammalian cells. Vectors for the expression of heavy chains and light chains were originally described in Persic et al, (1997) Gene 187:9-18. To obtain antibody 1 as $IgG_2$, the heavy and light chain IgG expressing vectors were transiently transfected into HEK293-EBNA mammalian cells where the antibody was expressed and secreted into the medium. Harvested media was clarified by centrifugation prior to purification. The IgG was purified using Protein A (GE Healthcare). Culture supernatants were loaded onto a 1 ml column pre-equilibrated in 50 mM Tris, 0.15 M NaCl pH 8 buffer. The IgG was eluted from the column using 0.1 M Citrate pH 3 directly into 1 M Tris pH 10. The eluates underwent buffer exchange using NAP-10 buffer exchange columns (GE Healthcare) into 1×DPBS. The purified IgG was 0.2 micrometers sterile filtered, analysed for endotoxin, characterised by SDS PAGE and the concentration determined by absorbance at 280 nm.

1.6 Inhibition of IL-18 Binding to IL-18 Receptors Alpha and Beta by Antibody 1 IgG2

As described above, the purified Antibody 1 scFv that prevented the formation of the IL-18, IL-18Rα and IL-18Rβ complex was converted to recombinant $IgG_2$. The purified antibody 1 $IgG_2$ was serially diluted and tested in the HTRF™ IL-18 ligand-receptor assay described in section 1.3. $IgG_2$ preparations of Antibody 1 inhibited the formation of human IL-18/human IL-18 receptor complex with an $IC_{50}$ value of 2.9 nM (Geomean, n=2; FIG. 2A).

In some experiments recombinant human IL-18 was substituted with recombinant Rhesus Macaque IL-18 (R&D Systems, Minneapolis, Minn.; Cat. #2548-RM; Accession # AAK13416) at a final concentration of 1.5 nM. The amino acid sequence of rhesus macaque IL-18 presents 100% homology with cynomolgus monkey IL-18. The labelled human IL-18 receptors, detection reagents and assay parameters were the same as described in section 1.3. Preparations of Antibody 1 $IgG_2$ inhibited the formation of the recombinant Rhesus Macaque IL-18/human IL-18 receptor complex with an $IC_{50}$ value of 5.4 nM (Geomean, n=2; FIG. 2B).

1.7 Inhibition by Antibody 1 IgG2 of IFN⊂ Production by KG-1 Cells Stimulated with IL-18

The potency of Antibody 1 $IgG_2$ to neutralise the biological activity of recombinant human IL-18 was established using a KG-1 cell assay. The KG-1 cells (human myelogenous leukaemia cell line) have been shown to express IL-18Rα and IL-18Rβ chains and produce Interferon-gamma (IFNγ) in response to exogenous recombinant human IL-18 (Konishi et al (1997) J. Immunol. Methods 209(2): 187-191). KG-1 cells (ECACC, United Kingdom; cat. #86111306) were plated at $10^5$ cells/100 µl/well in culture medium (IMDM [Invitrogen Corp., Paisley, UK; Cat. #21980-032] containing 5% v/v heat-inactivated FBS, 100 U/ml penicillin and 100 µg/ml streptomycin [Invitrogen Corp., Paisley, UK; Cat. #15140-122]) into Costar® 96-well flat bottom tissue culture-treated plates (Corning, Lowell, Mass.; Cat. #3596). Recombinant Tumor Necrosis Factor alpha (TNFα) (R&D Systems Minneapolis, Minn.; Cat. #210-TA), which was shown to synergise with IL-18 to induce IFNγ production, was added at a final concentration of 1.1 nM. To determine the potency of Antibody 1 $IgG_2$, test solutions were prepared by making serial dilutions of antibody (final concentrations in the cell assay of between 700 nM and 0.1 nM) in culture medium in U-bottom 96-well polypropylene plates (Greiner Bio-One, Kremsmunster, Austria; Cat. #650201). Recombinant human IL-18 (in house, E. coli-derived) was added to each well to give a final concentration in cell assay of 3 ng/ml to 8 ng/ml. The concentration was selected based on the dose giving, at final concentration and in the presence of 1.1 nM TNFα, an approximately 50% increase in maximal IFNγ secretion. Antibody 1/IL-18 mixtures were incubated for 30-45 minutes at room temperature prior to transfer of 100 µl of the samples to the KG-1 cells prepared as indicated above. After incubation of the cells for 22-24 hours at 37° C./5% $CO_2$ in a humidified atmosphere, 150 µl of supernatant were collected from each well and the concentration of IFNγ was determined as indicated below.

Briefly, Nunc™ black 96-well Maxisorp plates (Thermo Fisher Scientific, Rochester N.Y.; Cat. #437111) were coated overnight with 4 µg/ml of capture anti-IFNγ antibody (BD Biosciences Pharmingen, Franklin Lakes, N.J.; Cat. #551221; clone NIB42). Plates were then washed with PBS and non specific binding was prevented by blocking with 200 µl in each well of PBS containing 3% milk powder (Marvel). Plates were incubated 1 hour at room temperature and washed 3 times with PBS. Wells were then filled with 100 µl of either experimental samples diluted ½ or serially diluted recombinant human IFNγ (R&D Systems, Minneapolis, Minn.; Cat. #285-IF) used to establish a standard curve (concentration range 40000-39 pg/ml). These samples were incubated for 1 hour at room temperature and the plates were then washed 3 times in PBS containing 0.01% Tween-20. In order to detect IFNγ binding to the plate, 100 µl of biotinylated anti-IFNγ antibody (BD Biosciences Pharmingen, Franklin Lakes, N.J.; Cat. #554550; clone 4S.B3) was added at a final concentration of 1 µg/ml and incubated for 1 hour at room temperature. After washing the plates 3 times in PBS containing 0.01% Tween-20, 100 µl of DELFIA® Eu-labeled streptavidin (PerkinElmer, Boston Mass.; Cat. #1244-360) diluted ¹⁄₁₀₀₀ in DELFIA assay buffer (PerkinElmer, Boston Mass.; Cat. #4002-0010) were added. The plates were further incubated 1 hour at room temperature and then washed 7 times using DELFIA washing solution (PerkinElmer, Boston Mass.; Cat. #1244-114). One hundred microliters of DELFIA enhancement solution (PerkinElmer, Boston Mass.; Cat. #4001-0010) were added to each well and plates were incubated 10 minutes in the dark at room temperature. The response in each well was then determined using an Envision plate reader (PerkinElmer, Boston Mass.) measuring dissociation-enhanced time-resolved fluorescence.

Experimental data were normalised using Europium counts obtained for KG-1 cells stimulated with IL-18 in absence of antibody and the concentration of antibody inhibiting 50% of IFNγ release ($IC_{50}$) was determined. $IC_{50}$ values were calculated using GraphPad Prism software by curve fitting using a four-parameter logistic equation (Equation 3 in section 1.4).

The $IC_{50}$ of Antibody 1 when tested as a purified $IgG_2$ was 258 nM (Geomean, n=4, 95% CI: 121-550 nM).

1.8 Determination of Binding Affinity of Antibody 1 IgG2 to IL-18 Using Surface Plasmon Resonance.

The BIAcore 2000 (GE Healthcare) biosensor instrument was used to assess the kinetic parameters of the interaction between Antibody 1 and recombinantly expressed human IL-18. These experiments were performed essentially as described by Karlsson et al (1991) J. Immunol. Methods 145(1-2):229-240.

The biosensor uses the optical effects of surface plasmon resonance (SPR) to study changes in surface concentration resulting from the interaction of an analyte molecule that is flowed over a ligand molecule that is covalently attached to the dextran layer of a biosensor chip. Typically, a defined concentration of the analyte species is passed over the coupled ligand and any binding is detected as an increase in local SPR signal (association phase). This is followed by a period of buffer flow, during which dissociation of the analyte species from the surface immobilised ligand can be observed as a decrease in signal (dissociation phase). The remaining analyte can then be stripped from the chip-bound ligand and the procedure repeated at several different analyte concentrations. The experiment is designed such that neither the absolute binding capacity nor kinetic profile of the coupled ligand change significantly during the entire experiment and can be monitored using a series of controls employed throughout the experiment. A proprietary HEPES buffered saline containing EDTA (HBS-EP+; GE Healthcare) is typically used as the diluent buffer for the analyte samples and as the flow buffer during the dissociation phase. The experimental data is recorded as 'Resonance Units' (RUs), which are arbitrary units that directly correspond to the SPR signal over time. The RUs are directly proportional to changes in the refractive index on the chip surface, which in turn is an approximate measure of the mass of analyte bound. The proprietary BIAevaluation software package can then be used to process data and fit binding models to the data sets. Returned association (ka; $M^{-1} s^{-1}$) and dissociation (kd; $s^{-1}$) rate constants allow calculation of dissociation (KD; M) affinity constants.

The affinity of binding between the Antibody 1 $IgG_2$ and IL-18 analyte was estimated using assays in which the antibody was covalently coupled by amine-linkage to a proprietary CM3 chip surface to a final surface density of approximately 600 RU. The chip surface was regenerated between cycles by paired 15s injections of 10 mM Glycine pH2 to remove IL-18 bound to the antibody. The regeneration did not result in a significant loss of antibody binding activity.

A series of dilutions of recombinant human IL-18 (0.4-200 nM) were sequentially passed over the Antibody 1 $IgG_2$ for a sufficient amount of time to observe sensorgrams that could be fitted to a 1:1 binding model with confidence. Blank reference flow cell data was subtracted from each IgG dataset and a zero-concentration buffer blank was double-reference subtracted from the main data set to reduce any buffer artefacts or (minimal) non-specific binding effects. The 1:1 Langmuir model were then fitted simultaneously to the data from each analyte titration using the BIAevaluation software.

The validity of the data was assessed using the calculated $Chi^2$ and T value (parameter value/offset), of which minimum accepted values were constrained to be <2 and >100 respectively and assessed for overall success of fit using the residuals (<2 RUs).

Using recombinant human IL-18 as an analyte, Antibody 1 $IgG_2$ association rate (Ka), dissociation rate (Kd) and affinity constant (KD) were $7.35 \times 10^5 M^{-1} s^{-1}$, $7.32 \times 10^{-2} s^{-1}$ and 9.96 nM respectively.

1.9 Analysis of Binding Specificity of Antibody 1 $IgG_2$ Using Surface Plasmon Resonance Biosensor.

The BIAcore 2000 biosensor instrument (GE Healthcare) was used to assess the specificity of interaction between Antibody 1 $IgG_2$ with a range of recombinantly expressed IL-18 proteins and proteins related to IL-18 biology.

The binding interactions between Antibody 1 and analyte protein were analysed using assays in which Antibody 1 was covalently coupled by amine-linkage to a CM3 chip surface to a final surface density of approximately 600 RU. Two hundred nanomolar solutions of recombinant human IL-18, Rhesus Macaque IL-18 (R&D Systems, Minneapolis, Minn.; Cat. #2548-RM), rat IL-18 (R&D Systems, Minneapolis, Minn.; Cat. #521-RL-025), human IL-1beta (R&D Systems, Minneapolis, Minn.; Cat. #201-LB) or human IL-1F7/FIL1zeta (R&D Systems, Minneapolis, Minn.; Cat. #1975-IL-025) diluted in running buffer were injected over the chip surface. Afterwards, the chip surface was regenerated between cycles by paired injections of 10 mM Glycine pH2 to remove IL-18 bound to the antibody.

Of the proteins presented to Antibody 1, the IgG was observed to selectively bind only human and Rhesus Macaque IL-18. No significant binding was observed with recombinant rat IL-18, human IL-1beta nor human IL-1F7/FIL1zeta.

1.10 Characterisation of Antibody 1 in an IL-18 Binding Protein Epitope Competition Assay To determine if Antibody 1 could inhibit the binding of human IL-18 Binding Protein (IL-18BP) to human IL-18, an epitope competition assay was developed. Dilution series of antibody 1 as purified scFv or $IgG_2$ were prepared ranging from 4893 nM to 41.4 pM for the scFv and 987 nM to 16.8 pM for the $IgG_2$. Ten microliters of each dilution were transferred into a Costar® 384 well assay plate (Corning, Lowell, Mass.; cat. #3676). Separately, 1.73 nM cryptate labelled anti-FLAG antibody (Cis Bio International, Bagols-sur-Ceze, France; cat. #61FG2KLB) was combined with 3.2 nM Baculovirus-produced IL-18 (in-house) containing FLAG and His tags. Five microliters of this mixture were added to the assay plate with the Antibody 1 scFv or $IgG_2$. Human IL-18BPa-Fc (R&D Systems, Minneapolis, Minn.; cat. #119BP) was biotinylated via free amines using EZ link Sulfo-NHS-LC-Biotin (Thermo Fisher Scientific, Rochester N.Y.; Cat. #21335) in PBS at pH 8. Biotinylated IL-18BPa-Fc at 0.8 nM was combined with 20 nM Streptavidin Xlent! (C is Bio International. cat. #611SAXLB) and 5 µl of this solution were added to the assay plate.

Non-specific binding was defined using human IL-18 (generated in-house) at a 25 nM final concentration. All dilutions were performed in phosphate buffered saline (PBS) containing 0.4 M KF and 0.1% BSA (assay buffer).

Assay plates were incubated for 4 hours at room temperature and then overnight at 4° C., prior to reading time resolved fluorescence at 620 nm and 665 nm emission wavelengths using an EnVision plate reader (Perkin Elmer, Boston, Mass.). Results were calculated using the equations described in sections 1.3 and 1.4.

Figure 3:
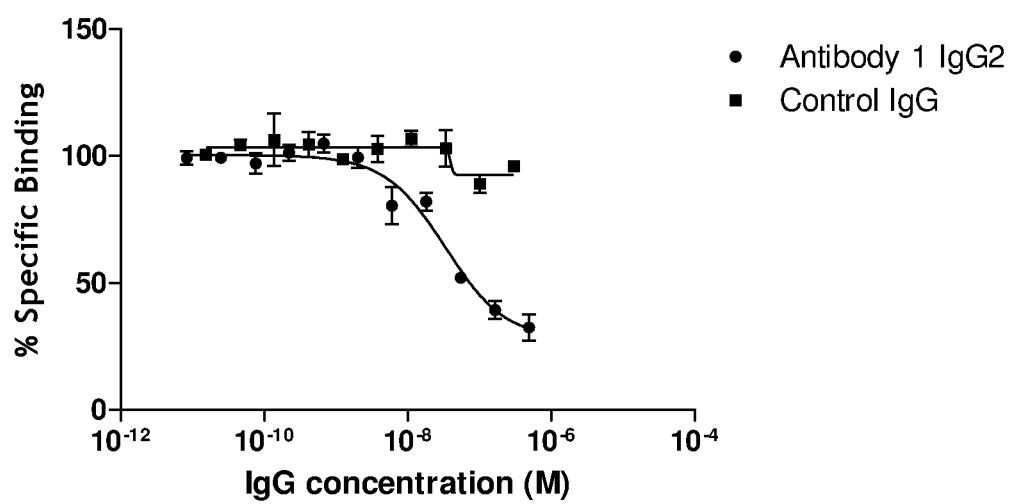
FIG. 3 shows the inhibition of the human IL-18BPa-Fc binding to human IL-18-FH by increasing concentrations of Antibody 1 IgG$_2$ (circles). The Y axis represents the specific binding of the IL-18 to IL-18BPa-Fc as a percentage of the total binding observed in the absence of any IgG. Data represent mean values of duplicate points with SEM.

Preparations of purified scFv Antibody 1 generated an average inhibition of 86% at 2446 nM. $IgG_2$ preparations of Antibody 1 generated an average inhibition of 68% in this assay at 493 nM (FIG. 3).

Example 2

Antibody Optimisation 2.1 Optimisation of Antibody 1 by Targeted Mutagenesis

Antibody 1 was optimised for improved affinity to both human and Rhesus Macaque IL-18 using a targeted mutagenesis approach and affinity-based phage display selections. Large scFv-phage libraries derived from Antibody 1 were created by oligonucleotide-directed mutagenesis of the variable heavy ($V_H$) and light ($V_L$) chain complementarity determining regions 3 (CDR3) using standard molecular biology techniques as described by Clackson and Lowman (2004) A Practical Approach, 2004. Oxford University Press.

The libraries were subjected to affinity-based phage display selections in order to select variants with higher affinity for recombinant human and Rhesus Macaque forms of IL-18. The selections were performed essentially as described previously (Thompson (1996) Journal of Molecular Biology 256:77-88). In brief, the scFv phage particles were incubated with recombinant biotinylated recombinant human IL-18 in solution (bio-huIL-18, in house, E. coli-derived). ScFv-phage bound to antigen were then captured on streptavidin-coated paramagnetic beads (Invitrogen Corp., Paisley, UK; Dynabeads® M280) following the manufacturer's recommendations. The selected scFv-phage particles were then rescued as described previously (Osbourn et al (1996) Immunotechnology, 2 (3); 181-96), and the selection process was repeated in the presence of decreasing concentrations of biotinylated human IL-18 (25 nM to 500 pM over 3 rounds). This process led to the isolation of Antibody 2, Antibody 3, Antibody 4 and Antibody 5 with improved potency in the biochemical epitope competition assay (section 2.3) and the KG-1 cell assay (table 1).

Upon completion of three rounds of affinity based selections, the VH and VL randomised libraries were then recombined to form a single library in which clones contained randomly paired individually randomised VH and VL sequences. Selections were then continued as previously described in the presence of decreasing concentrations of biotinylated human IL-18 (500 pM to 20 pM over a further 3 rounds) leading to the isolation of improved clones Antibody 6 and Antibody 7.

2.2 Optimisation of Lead Antibodies by Random Mutagenesis

Antibody 6 and Antibody 7 were further optimised using a random mutagenesis approach to identify key residues within the scFv variable domains that may improve binding to recombinant human and Rhesus Macaque IL-18. Large scFv-ribosome display libraries were generated by the introduction of random mutations throughout the variable regions of antibodies 6 and 7. This was achieved by two rounds of mutagenesis using A Diversify™ PCR random mutagenesis kit (BD biosciences, Franklin Lakes N.J.; Cat. #630703), following the manufacturer's instructions to incorporate on average, 8.1 mutations per kilobase in the nucleic acid sequence per round of mutagenesis.

The selections were performed essentially as described previously (Hanes et al (2000) Methods in Enzymology 328: 404-430). In brief, the random mutagenesis libraries of the 2 lead clones identified from the targeted CDR3 randomisation strategy (Antibody 6 and Antibody 7) were transcribed into mRNA and subsequently pooled to create one library. Using a process of stalled translation, mRNA-ribosome-scFv complexes were formed (Hanes J and Plückthun A. (1997) Proc Natl Acad Sci USA. 1997 May 13; 94(10):4937-42). These complexes were then subjected to three rounds of selections incubated in the presence of decreasing concentrations of either biotinylated human IL-18 or biotinylated Rhesus Macaque IL-18 (1 nM to 30 pM over 3 rounds) to select for variants with higher affinity for both human and Rhesus Macaque forms of IL-18. Those complexes that bound to the antigen were then captured on streptavidin-coated paramagnetic beads (Dynabeads™). Non-specific ribosome complexes were washed away, and mRNA was isolated from the bound ribosomal complexes, reverse transcribed to cDNA and then amplified by PCR. This DNA was used for the next round of selection and/or cloned out for screening. ScFv isolated by ribosome display were cloned into the phagemid vector pCANTAB6 by Nco1/Not1 restriction endonuclease digestion (New England Biolabs, Ipswich Mass.) of the ribosome display construct, followed by ligation into Nco1/Not1 digested pCANTAB6 using T4 DNA ligase (New England Biolabs, Ipswich Mass.) (McCafferty et al (1994) Appl. Biochem. Biotech. 47:157-171,).

This optimisation strategy led to the isolation of improved clones Antibody 9 and Antibody 10.

Further point mutations were introduced in Antibody 7, Antibody 9 and Antibody 10 by site directed mutagenesis which led to Antibody 8 GL, Antibody 11, Antibody 11 GL and Antibody 12 GL. These point mutations were in HCDR1 (Ser31Ala) and HCDR2 (Ile51Leu, Ser65Gly).

2.3 Identification of Improved Clones Using an Epitope Competition Assay

Eight hundred eighty scFv, randomly selected from selection rounds 2 and 3 from the targeted mutagenesis approach described in section 2.1, were expressed in bacteria and unpurified scFv were screened in an epitope competition HTRF™ assay format. In this assay, unpurified scFv competed with Antibody 1 $IgG_2$ for binding to Europium cryptate labelled human IL-18 (in-house). Europium cryptate labelling of recombinant human IL-18 was achieved using Trisbipyridine-Eu3+-cryptate-4-carboxy-4'-(Maleimidopropionamido-2-aminoethyl-aminocarbonyl) (C is bio International, Bagnols-sur-Ceze, France; cat. #65EUMABA) in PBS at neutral pH. Selection outputs were screened as undiluted or diluted periplasmic extracts containing unpurified scFv prepared in 50 mM MOPS buffer pH 7.4, 0.5 mM EDTA and 0.5 M sucrose and diluted in phosphate buffered saline (PBS) containing 0.4 M KF and 0.1% BSA (assay buffer). Twenty four nanomolar of Antibody 1 $IgG_2$ and 30 nM of anti-human Fc XL665 (C is Bio International, Bagnols-sur-Ceze, France; cat. #61HFCXLA) were diluted together in assay buffer. Ten microliters of this solution were transferred to a Costar® 384 well assay plate (Corning, Lowell, Mass.; Cat. #3676). Five microliters of unpurified scFv was added to the assay plate followed by Europium cryptate labelled recombinant human IL-18 diluted to 1.2 nM. Non-specific binding was determined using monoclonal mouse anti-human IL-18 clone 125-2H(R&D Systems, Minneapolis, Minn.) at a 20 nM final concentration. Assay plates were incubated for 3 hours at room temperature, prior to reading time resolved fluorescence at 620 nm and 665 nm emission wavelengths using an EnVision plate reader (Perkin Elmer, Boston Mass.) as described in section 1.3. Data was calculated as % Specific Binding using equations described in section 1.3. ScFv that showed significant inhibitory properties, preventing Antibody 1 $IgG_2$ from binding to IL-18, were subjected to DNA sequencing and scFv with unique sequences were prepared as purified preparations.

The potency of purified scFv antibodies was determined by testing dilution series of the purified scFv preparations in the Antibody 1 $IgG_2$ epitope competition assay described above using the same conditions. Purified scFv preparations of Antibody 2, Antibody 3, Antibody 4 and Antibody 5 inhibited the interaction between Antibody 1 $IgG_2$ and Europium cryptate labelled IL-18 with $IC_{50}$ values of 0.5, 0.6, 0.6 and 0.17 nM respectively (n=1).

Screening from the post recombination targeted mutagenesis selections used the same epitope competition assay as described above except the Europium cryptate labelled IL-18 concentration was reduced to 0.2 nM final assay concentration. Improved clones were identified using this assay and these were taken forward for direct profiling in the KG-1 functional cell assay as described in section 2.4. From this approach Antibody 6 and Antibody 7 were identified as improved scFv. To further optimise these lead antibodies a random mutagenesis approach was followed as described in section 2.2.

ScFv from the random mutagenesis selections were expressed in bacteria and unpurified scFv were screened in an HTRF™ epitope competition assay format. This assay tested the ability of the unpurified scFv to inhibit the Europium cryptate labelled IL-18 from binding to germlined (GL) Antibody 6 $IgG_2$ (germlining of IgG described in section 2.7). The same format as described above was used except that Antibody 1 $IgG_2$ was replaced with Antibody 6 GL $IgG_2$ at a final concentration of 12 nM and Europium cryptate labelled recombinant human IL-18 was used at 0.2 nM final concentration. To define the non-specific binding in this assay Antibody 6 GL $IgG_2$ was omitted from the control wells.

Figure 4:
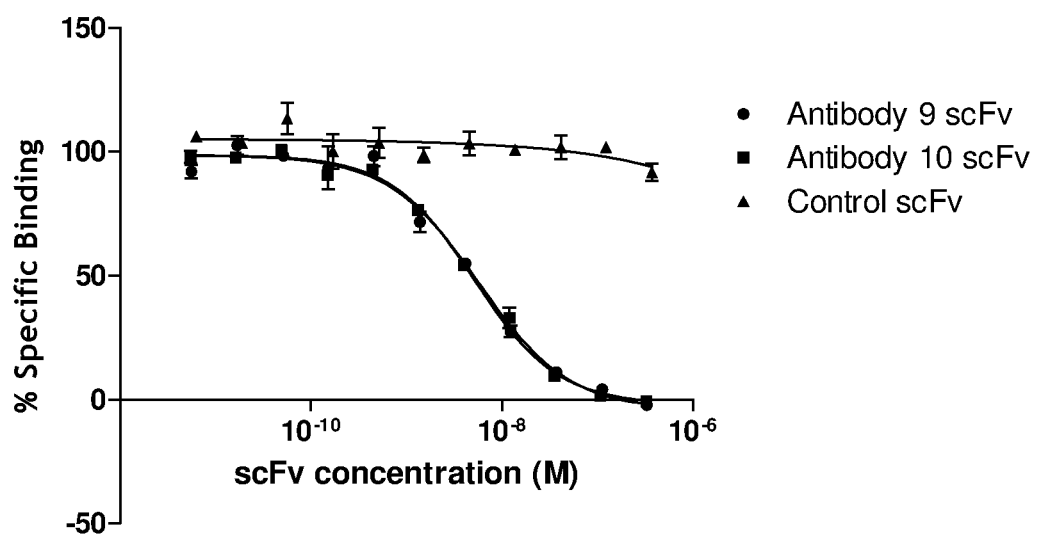
FIG. 4 shows the inhibition of the Antibody 6 GL binding to human IL-18 by increasing concentrations of Antibody 9 scFv (circles) and Antibody 10 scFv (squares). The Y axis represents the specific binding of IL-18 to Antibody 6 GL as a percentage of the total binding observed in the absence of any scFv. Data represent mean values of duplicate points with SEM.

Hits identified from the screening of the random mutagenesis selections were ranked and the best scFv sequenced and purified. To determine the potency of the scFv a dilution series of purified scFv were tested in the Antibody 6 GL $IgG_2$ epitope competition assay as described above. Purified preparations of Antibody 9 and Antibody 10 inhibited the interaction between Antibody 6 GL $IgG_2$ and Europium cryptate labelled recombinant human IL-18 with $IC_{50}$ values of 5.2 and 5.7 nM respectively (n=1) (FIG. 4).

2.4 Inhibition by Optimised Clones (scFv) of IFN⊂ Production by KG-1 Cells Stimulated with IL-18

Figure 5:
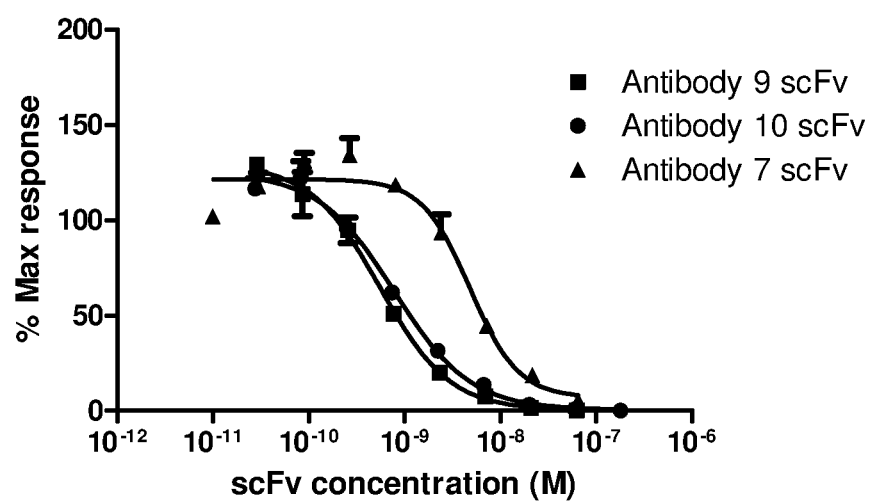
FIG. 5 shows the inhibition of IFNγ release by KG-1 cells stimulated with exogenous human IL-18 and TNFα in the presence of increasing concentrations of antibody 9 scFv (squares), antibody 10 scFv (circles) and antibody 7 scFv (triangles). The Y-axis represents the IFNγ release as a percentage of maximum response which is obtained in absence of neutralising antibodies. Data represent mean values of duplicate wells with SEM.

The potencies of purified optimised scFv antibodies generated by targeted mutagenesis and random mutagenesis were also determined in the IFNγ release KG-1 cell assay using human and Rhesus Macaque IL-18 as agonist. The assay was set up as described in section 1.7. In some experiments human IL-18 was replaced by recombinant Rhesus Macaque IL-18 (R&D systems, Minneapolis Minn.; cat. #2548-RM/CF) which was used at a final concentration of 4 ng/ml. The scFv were tested at a final concentration range of between 100 nM and 0.03 nM. Example potencies for purified scFv antibodies are provided in table 1. Representative data for antibody 7, antibody 9 and antibody 10 scFv are shown in FIG. 5.

2.5 Reformatting of scFv to IgG2 and IgG1TM scFv were reformatted to $IgG_2$ by subcloning the variable heavy chain (VH) and variable light chain (VL) domains into vectors expressing whole human antibody heavy and light chains respectively. The variable heavy chain was cloned into a mammalian expression vector (pEU9.2) containing the human heavy chain constant domains and regulatory elements to express whole $IgG_2$ heavy chain in mammalian cells. Similarly, the variable light chain domain was cloned into a mammalian expression vector for the expression of the human kappa (vector pEU3.4) light chain constant domains and regulatory elements to express whole IgG light chain in mammalian cells. To obtain antibodies as $IgG_2$, the heavy and light chain IgG expressing vectors were transiently transfected into HEK293-EBNA mammalian cells where the antibody was expressed and secreted into the medium. Harvested media was clarified by centrifugation prior to purification. The IgG was purified using Protein A (GE Healthcare). Culture supernatants were loaded onto a 1 ml column pre-equilibrated in 50 mM Tris, 0.15M NaCL pH 8 buffer. The IgG was eluted from the column using 0.1M Citrate pH 3 directly into 1M Tris pH 10. the eluates underwent buffer exchange using NAP-10 buffer exchange columns (GE Healthcare) into 1×DPBS. The purified IgG was 0.2 micrometers sterile filtered, analysed for endotoxin, characterised by SDS PAGE and the concentration determined by absorbance at 280 nm.

Figure 15:
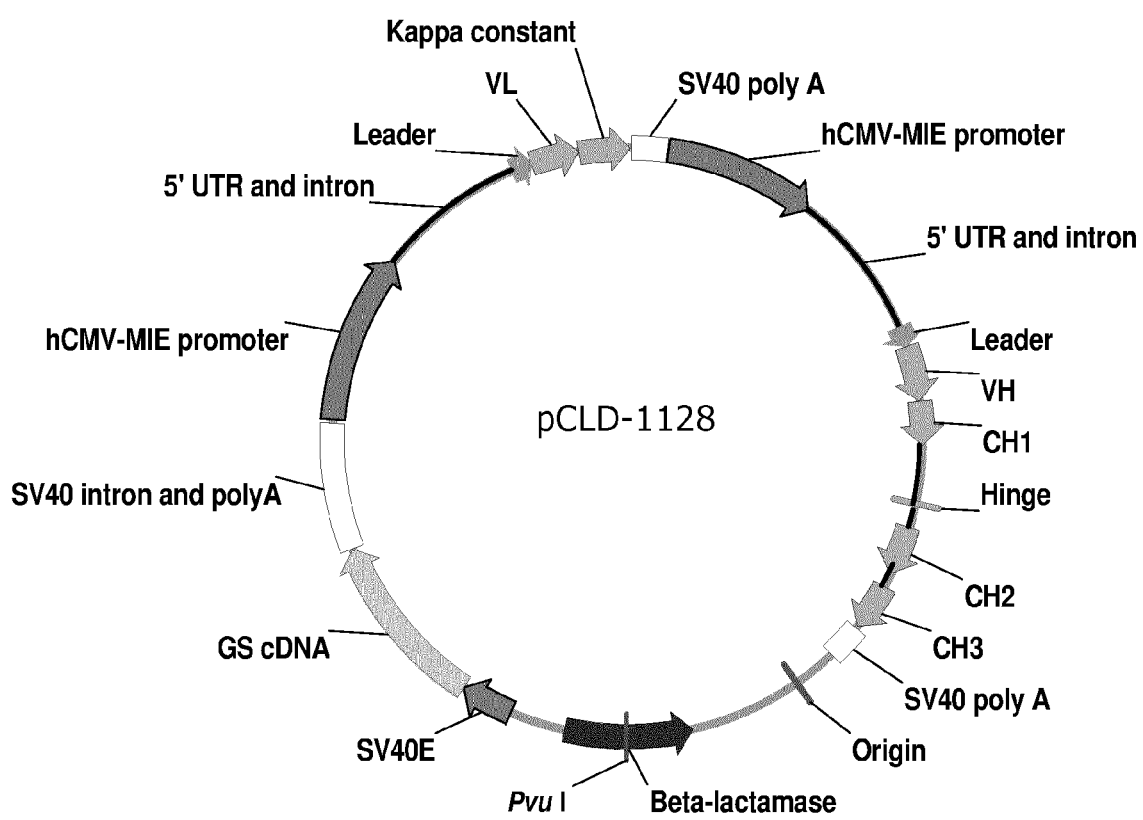
FIG. 15 shows a map of the pCLD-1128 plasmid.

Antibody 12 GL was also converted to the human $IgG_1$ isotype containing three single amino acid substitutions (TM) within the constant domain ([$IgG_1$TM]; Oganesyan et al (2008) Acta Crystallogr D Biol Crystallogr. 64(Pt 6):700-4). Briefly, the IgG light chain gene was made of a secretory leader sequence fused to the antibody variable domain sequence and the human kappa Km3 constant domain sequence. The IgG heavy chain gene was made of a secretory leader sequence fused to the antibody variable domain with the human gamma 1 (f) constant domain sequences with TM modifications. The DNA sequences encoding the light chain and heavy chain genes were optimised (see SEQ ID NOS: 170 and 171) (Geneart AG, Regensburg, Germany) for high level expression in Chinese Hamster Ovary (CHO) cells prior to DNA cloning into the expression cassette vectors, pEE12.4 and pEE6.4 respectively (Lonza Biologics, Slough, UK). The antibody heavy chain gene including its flanking transcriptional regulatory sequences were then inserted into the antibody light chain plasmid to create a double antibody gene, tandem vector (pCLD-1128) (see FIG. 15). The pCLD-1128 plasmid was linearised and transfected into the CHO host cell line, CHOK1SV (Lonza Biologics) which had been pre-adapted to growth in suspension culture in chemically-defined medium (CD-CHO; Invitrogen, Paisley, UK). Transfectants containing copies of the pCLD-1128 plasmid that were integrated into the CHO genome were selected by growth in glutamine-free CD-CHO medium containing methionine sulphoximine.

Pools expressing high yields of the antibody were selected and expanded to inoculate fed-batch production cultures. At approximately 14 days post-inoculation, the culture harvest was clarified by centrifugation and/or filtration to remove cells and cellular debris. The antibody was then recovered from the resulting culture supernatant by protein A affinity chromatography followed by PD10 buffer exchange into a suitable buffer.

2.6 Inhibition by Optimised Clones (IgG) of IFNγ Production by KG-1 Cells Stimulated with IL-18

The most potent scFv clones in the KG-1 cell assay were converted to IgG as described above (section 2.5), and were re-tested in this cell assay at a final concentration range of between 20 nM and 0.002 nM. Example potencies for purified IgG antibodies are provided in table 2.

2.7 Germlining

The amino acid sequences of the $V_H$ and $V_L$ domains of Antibody 1 and the affinity optimised anti-IL-18 antibodies were aligned to the known human germline sequences in the VBASE database (Tomlinson (1997) Journal of Molecular biology 224:487-499), and the closest germline was identified by sequence similarity. For the $V_H$ domains of the optimised antibody lineage, this was Vh4_DP-66_(4-61). For the $V_L$ domains, it was Vκ1_L12. Except for Vernier residues (Foote & Winter (1992) J Mol Biol. 224(2):487-99) which were left unchanged, the germlining process consisted in reverting framework residues in $V_H$ and $V_L$ domains to the closest germline sequence to identically match human antibodies. The $V_H$ and $V_L$ domain sequences of all the antibodies produced are shown in Tables 12 and 13. Germlining of these amino acid residues was carried out using standard site directed mutagenesis techniques with the appropriate mutagenic primers. Changes introduced into the CDRs from the random mutagenesis strategy were then introduced into a fully germlined backbone. Germlined antibodies in an $IgG_2$ or $IgG_1$TM format were then re-evaluated in the KG-1 cell assay to confirm there had not been a significant reduction in potency. Example potencies for germlined (GL) antibodies are provided in Table 3. Representative data for Antibody 8 GL, Antibody 11 GL and Antibody 12 GL IgG are shown in FIG. 6.

2.8 Inhibition by Germlined Optimised Clones (IgG) of IFNγ Production by Human PBMC Stimulated with LPS and IL-12

As well as their potency to inhibit recombinant human and Rhesus Macaque IL-18, germlined IgG were tested for their ability to neutralise endogenously produced IL-18. Peripheral blood mononuclear cells (PBMC) were purified from either human buffy coat blood or cynomolgus monkey blood and stimulated with LPS (Sigma-Aldrich, St Louis Mo.; cat. #L-6143) and recombinant human IL-12 (R&D Systems, Minneapolis Minn.; cat. #219-IL) to trigger IFNγ release via an IL-18-dependant mechanism. The ability of optimised germlined IgG to antagonise endogenous IL-18 and consequently block IFNγ production was assessed in this assay. Briefly, the PBMC were washed by centrifugation at 300 g for 10 minutes in culture medium (RPMI-1640 [Invitrogen Corp., Paisley, UK; cat. #61870-010] containing 10% v/v heat-inactivated FBS [SAFC Biosciences; cat. #12076C], 100 U/ml penicillin and 100 µg/ml streptomycin [Invitrogen Corp., Paisley, UK; cat. #15140-122]). PBMC were resuspended in culture medium and plated at $4 \times 10^5$ cells/100 µl/well (for evaluation of antibody 8 GL IgG$_2$, Antibody 11 GL IgG$_2$ and Antibody 12 GL IgG$_2$) or at $2 \times 10^5$ cells/100 µl/well (for Antibody 12 GL IgG$_1$TM) into a Costar® 96-well flat bottom tissue culture-treated plates (Corning, Lowell, Mass.; Cat. #3596). To determine the potency of optimised germlined IgG, test solutions were prepared by making serial dilutions of IgG (final concentrations in the cell assay of between 2.5 pM and 16.7 nM) in culture medium in U-bottom 96-well polypropylene plates (Greiner Bio-One; Kremsmunster, Austria; Cat. #650201). Fifty microliters of these solutions were transferred to the wells of the plates containing the PBMC. In order to trigger the production of endogenous IL-18 the cells were then stimulated by adding 50 µl of a mixture of LPS (Sigma-Aldrich, St Louis Mo.; cat. #L-6143) and recombinant human IL-12 (R&D Systems, Minneapolis Minn.; cat. #219-IL), both at 1 ng/ml final. After incubation of the cells for 24 hours at 37° C./5% CO$_2$ in a humidified atmosphere, 150 µl of supernatant were collected from each well and the concentration of IFNγ was determined as indicated in section 1.7.

Experimental data were normalised using Europium counts obtained for PBMC stimulated with LPS and IL-12 in absence of antibody and the concentration of antibody inhibiting 50% of IFNγ release (IC$_{50}$) was determined. IC$_{50}$ values were calculated using GraphPad Prism software by curve fitting using a four-parameter logistic equation (Equation 3 in section 1.4).

Example potencies for germlined (GL) antibodies in this assay are provided in Table 4. Representative data for antibody 12 GL IgG$_1$TM in assays based on human and cynomolgus monkey PBMC are shown in FIG. 7.

2.9 Inhibition of IL-18-Induced CD11b Up-Regulation on Primary Neutrophils by Antibody 12 GL IgG$_1$TM CD11b has been shown to be up-regulated on neutrophils during activation. These cells play a key role in a number of inflammatory disorders and the ability of Antibody 12 GL IgG$_1$TM to inhibit in vitro IL-18-induced CD11b up-regulation was determined by flow cytometry.

Fresh peripheral blood was obtained from healthy human volunteers and an equal volume of 2.4% dextran (GE Healthcare, Cat. #17-0320-01) was added to the blood and mixed well by inversion. Erythrocytes were then allowed to sediment for 1 hour. A discontinuous Percoll gradient (GE Healthcare, Cat. #17-0891-01) was then prepared by diluting Percoll 9:1 with 10×PBS (Invitrogen Corp., Paisley UK; Cat. #14200059) to make a 100% stock solution. This stock solution was further diluted with 1×PBS (Invitrogen Corp., Paisley UK; Cat. #14190) to form a 72% solution and a 67% solution. Three milliliters of the 72% solution were then added to 15 ml Falcon® tubes (BD Biosciences, Franklin Lakes N.J.; Cat. #352096) and 3 ml of the 62% solution were layered onto the 72% solution. After erythrocyte depletion, the erythrocyte depleted cell suspension was layered on top of the 62% solution in the 15 ml tubes. These tubes were centrifuged at 1138×g for 20 minutes with the brake off. The granulocyte layer was removed from the interface of the 72% and 62% Percoll into a fresh 50 ml Falcon® tubes (BD Biosciences, Franklin Lakes N.J.; Cat. #352070) containing PBS and then centrifuged at 300×g for 10 minutes. The supernatant was discarded and the granulocytes were resuspended in 50 ml of PBS and counted using trypan blue exclusion dye. The granulocytes were then pelleted at 200×g for 5 minutes and resuspended at $1-2 \times 10^6$/ml in stimulation buffer (RPMI-1640 [Invitrogen Corp., Paisley UK; Cat. #61870] and 2% BSA [Sigma-Aldrich, St Louis Mo.; Cat. #A9576]). One hundred microliters of the cell suspension was dispensed into the wells of a round-bottom 96-well polystyrene tissue culture treated plate (Costar, Kremsmunster, Austria; Cat. #650201). Cells were then treated with 100 µl of a solution containing a titration of Antibody 12 GL IgG$_1$TM (ranging from 2.55 pM to 16.7 nM) and 2.78 nM recombinant human IL-18 (in house, E. coli-derived) that had been pre-mixed for 5 minutes before addition. Plates were incubated at 37° C. in a humidified 5% CO$_2$ atmosphere for 2 hours.

Cells were then pelleted by centrifugation at 300×g for 3 minutes at 4° C. and the supernatant was flicked off. The cells were resuspended in 150 µl of PBS and centrifuged again. Cells were then resuspended in 100 µl FACS buffer (PBS with 2% FBS) containing 0.1 µg of FITC-conjugated anti-human CD11b (eBioscience Inc., San Diego Calif.; Cat. #11-0118, clone ICRF44) and incubated on ice for 30 minutes. Cells were then washed twice in 150 µl ice-cold PBS by centrifugation at 300×g for 3 minutes at 4° C. before fixation in 150 µl of 3.7% formaldehyde (Sigma-Aldrich, St Louis Mo.; Cat. #F1635-1GA) in PBS. The modulation of CD11b expression was determined using a FACSCanto II flow cytometer (BD Biosciences, Franklin Lakes N.J.). Neutrophils were identified by their characteristic forward scatter (FSC) and side scatter (SSC) properties. The corresponding population was gated and the fluorescence analysed in the FL-1 channel (Excitation wavelength 488 nm, filter 530/30) to evaluate CD11b expression levels.

Figure 8:
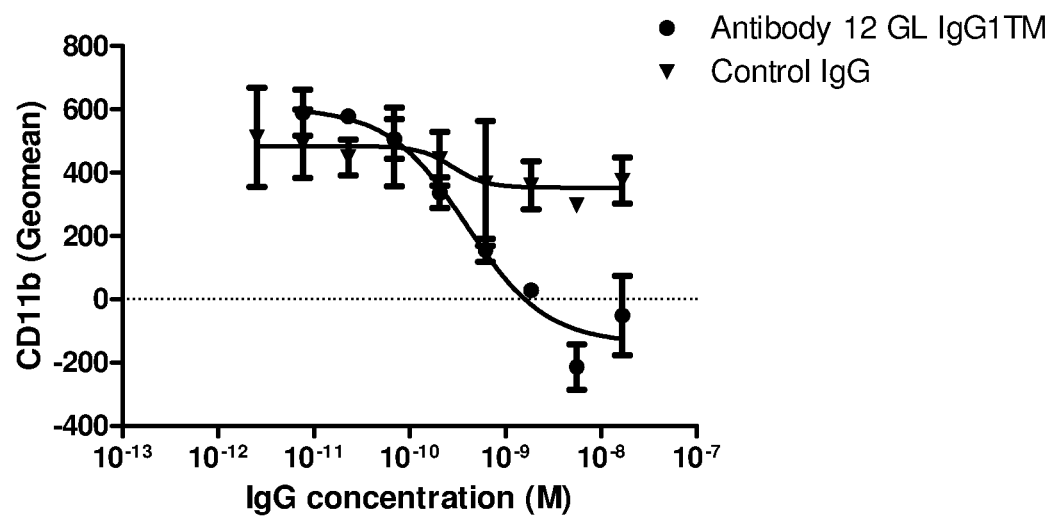
FIG. 8 shows the inhibition of CD11b up-regulation on human neutrophils stimulated with human IL-18 in the presence of increasing concentrations of germlined Antibody 12 IgG$_1$TM (circles) or a control IgG (triangles). The Y-axis represents the geometric mean of CD11b expression after deduction of the expression level in untreated cells. Data represent mean values of duplicate wells with SEM.

Antibody 12 GL IgG$_1$TM was able to inhibit the IL-18-induced up-regulation of CD11b on human neutrophils (FIG. 8) with geometric mean IC$_{50}$ of 2.032 nM (95% CI: 1.021-4.046 nM; n=7).

2.10 Inhibition by Antibody 12 GL IgG$_1$TM of IL-18-Induced Reactive Oxygen Species Production by Primary Neutrophils In the presence of appropriate co-stimulators such as formylated peptides IL-18 was shown to promote the production of a number of pro-inflammatory mediators by neutrophils including reactive oxygen species (ROS) (Elbin et al (2005) Clin Diagn Lab Immunol. 12(3):436-46). The ability of Antibody 12 GL IgG$_1$TM to inhibit in vitro the IL-18-induced enhancement of formyl peptide-induced ROS production by neutrophils was assessed by flow cytometry.

After isolation of neutrophils from human blood as described in section 2.9, the cells were resuspended at $1 \times 10^6$/ml in RPMI-1640 containing 1.5 µg/ml the ROS sensitive dye hydroethidine (Invitrogen, Paisley UK; Cat. #D11347) and incubated at 37° C. in a humidified 5% $CO_2$ atmosphere for 15 minutes. Cells were then pelleted by centrifugation at 300×g for 5 minutes, supernatant removed and resuspended in 50 ml of RPMI-1640 with 2% BSA. After one further centrifugation the cells were finally resuspended at a concentration of 3-5× $10^6$/ml in RPMI-1640 with 2% BSA. Fifty microliters of this cell suspension was plated into 96-well polystyrene tissue culture treated plates (Costar, Kremsmunster, Austria; Cat. #650201). Cells were then treated with 100 µl of a solution containing a titration of Antibody 12 GL $IgG_1$TM (ranging from 2.55 µM 16.7 nM) and 2.78 nM recombinant human IL-18 (in house, *E. coli*-derived) that had been pre-mixed for 5 minutes before addition. Plates were incubated at 37° C. in a humidified 5% $CO_2$ atmosphere for 2 hours. Cells were then stimulated with 50 µl of RPMI1640 with 2% BSA containing 400 nM fMLFF (Bachem, Germany; Cat. #H-4294). Cells were incubated for another 10 minutes at 37° C. in a humidified 5% $CO_2$ atmosphere. Cells were then washed twice in 150 µl of ice-cold PBS by centrifugation at 300×g for 3 minutes at 4° C. before fixation in 150 µl of 3.7% formaldehyde (Sigma-Aldrich, St Louis Mo.; Cat. #F1635-1GA) in PBS. The production of ROS was determined using a FACS-Canto II flow cytometer (BD Biosciences, Franklin Lakes N.J.). Neutrophils were identified by their characteristic forward scatter (FSC) and side scatter (SSC) properties. The corresponding population was gated and the fluorescence analysed in the FL-2 channel (Excitation wavelength 488 nm, filter 585/42) to evaluate ROS levels.

Figure 9:
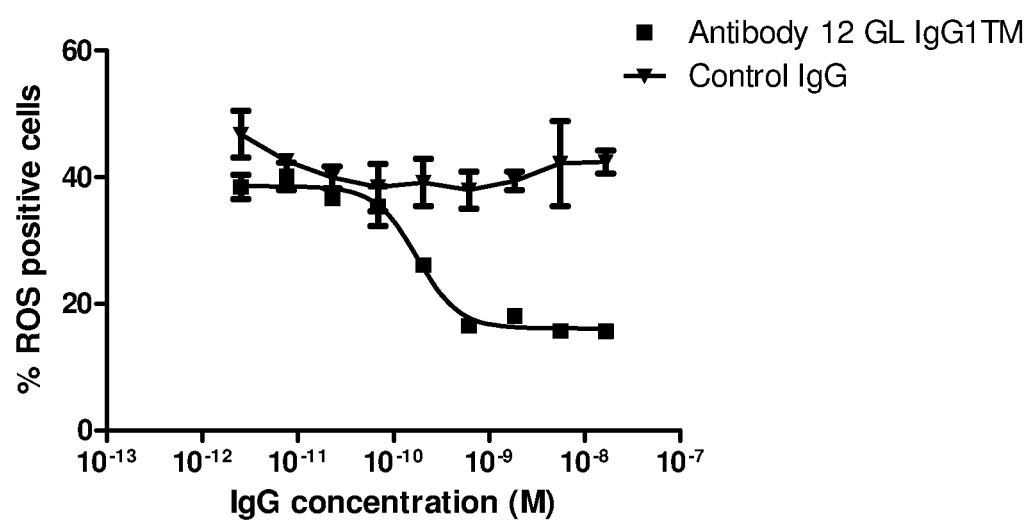
FIG. 9 shows the inhibition of Reactive Oxygen Species (ROS) production by human neutrophils stimulated with human IL-18 and fMLFF in the presence of increasing concentrations of germlined Antibody 12 IgG$_1$TM (squares) or a control IgG (triangles). The Y-axis represents the percentage of cells that are positive for ROS production (in the FL-2 channel) after deduction of the level seen in untreated cells. Data represent mean values of duplicate wells with SEM.

Antibody 12 GL $IgG_1$TM was able to inhibit the IL-18-mediated enhancement of fMLFF-induced ROS production in human neutrophils (FIG. 9) with geometric mean $IC_{50}$ of 0.200 nM (n=2).

2.11 Determination of Binding Affinity of Antibody 8 GL and Antibody 12 GL IgG to IL-18 Using Surface Plasmon Resonance.

The BIAcore 2000 or T-100 (GE Healthcare) biosensor instruments were used to assess the kinetic parameters of the interaction between anti-IL-18 antibodies, Antibody 8 GL and Antibody 12 GL, and recombinantly expressed human IL-18 (in house, *E. coli*-derived) or Rhesus Macaque IL-18 (R&D systems, Minneapolis Minn.; cat. #2548-RM) as detailed in a previous section (section 1.8).

Essentially, the affinity of binding between each IgG and IL-18 analyte was assessed by covalently coupling the IgG to a CM3 or CM5 chip by amine-linkage and dilutions of recombinant IL-18 (0.4-200 nM) sequentially passed over the chip surface (see section 1.8). The resulting data were fitted to the 1:1 Langmuir model (simultaneous $k_a$ $k_d$) and the mean values reported in table 5.

2.12 Pharmacological Determination of Antibody 12 GL $IgG_1$TM Affinity Using a Cell-Based Assay: $pA_2$ Analysis The main pharmacological tool to quantify the affinity of a competitive antagonist is Schild analysis. Using this approach a system-independent means of estimating the antagonist affinity in a functional assay may be determined. The method is based on the concept that the antagonist concentration and its affinity determines the antagonism of the agonist response. Because the antagonism can be quantified and the concentration of the antagonist is known, the affinity of the antagonist can be determined. This antagonism is quantified by measuring the ratio of equiactive concentrations of agonists, measured in the presence and absence of the antagonist, referred to as dose ratios (DR).

Dose ratios may be calculated by taking the ratio of the $EC_{50}$ of agonist (typically IL-18) in the absence of the binding member to the $EC_{50}$ of the agonist in the presence of a single concentration of binding member. The dose ratios, expressed as log(DR-1) may then be used in a linear regression on log [binding member] to produce a Schild regression. Thus, for every concentration of binding member there will be a corresponding DR value; these are plotted as the regression of log(DR-1) upon log [binding member]. If the antagonism is competitive, there will be a linear relationship between log (DR-1) and log [binding member] according to the Schild equation wherein the equation is as follows:

$$\text{Log}(DR-1) = \log[B] - \log K_B$$

[B] is the molar concentration of the binding member.

Under these circumstances, a value of zero for the ordinate will give an intercept of the x-axis where log [B]=log $K_B$. Therefore the concentration of binding member that produces a log(DR−1)=0 will be equal to the log $K_B$, the equilibrium dissociation constant of the binding member-receptor complex. This is a system independent quantification for estimation of the binding member affinity. Traditionally, this approach is used for determining the affinity of receptor antagonists, however based on similar assumptions for ligand neutralisation, a calculation of the dose ratio should enable estimation of the binding member affinity to neutralise IL-18 activity on cells also. Because the $K_B$ values are obtained from a logarithmic plot, they are log normally distributed. The negative logarithm of this particular concentration is referred to empirically as $pA_2$, the concentration of antagonist that produces a two fold shift of the agonist dose response curve. The antagonist potency can be quantified by calculating $pA_2$ from a single concentration of antagonist producing a single value for the dose ratio from the equation, wherein $$pA_2 = \log(DR-1) - \log[B]$$

[B]=molar concentration of antagonist that makes it necessary to double the agonist concentration to elicit the original submaximal response.

DR=the dose ratio is quantified by measuring the ratio of equiactive concentrations of agonist measured in the presence and absence of the antagonist.

$pA_2$ may be calculated from dose-response assay data.

In order to determine Antibody 12 GL $IgG_1$TM affinity for human IL-18 using the pA2 method, KG-1 cells were platted as described in section 1.7. Serial dilutions of Antibody 12 GL $IgG_1$TM (final concentrations in the cell assay of 20 nM, 6.66 nM, 2.22 nM, 0.74 nM, 0.25 nM and 0) were prepared in culture medium and added to the cells. Serial dilutions of recombinant human IL-18 (final concentration in the cell assay of between 42 nM and 0.25 pM) were also prepared in culture medium and added to the cells so that for each Antibody 12 GL $IgG_1$TM concentration a dose range of IL-18 was tested. After incubation of the cells for 22-24 hours at 37° C./5% $CO_2$ in a humidified atmosphere, 150 µl of supernatant were collected from each well and the concentration of IFNγ was determined as indicated in section 1.7. In some experiments, human IL-18 was replaced by rhesus macaque IL-18 used at the final concentrations of between 125 nM and 0.25 nM, in the presence of various concentrations of Antibody 12 GL $IgG_1$TM (final concentration of 60 nM, 20 nM, 6.66 nM, 2.22 nM, 0.74 nM, 0.25 nM and 0).

Experimental data were plotted in order to determine, for each antibody concentration, the amount of IL-18 required to trigger a 50% increase in IFNγ production by the KG-1 cells ($EC_{50}$). $EC_{50}$ values were calculated using GraphPad Prism software by curve fitting using a four-parameter logistic equation. The $EC_{50}$ values and antibody concentrations were then used to generate a Schild plot in GraphPad Prism and determine $pA_2$ and $K_D$ value as described above. FIG. 10 shows an example of dose dependant inhibition of human IL-18 effect on KG-1 cells by Antibody 12 GL IgG$_1$TM and the corresponding Schild plot allowing the determination of pA$_2$ and K$_D$ value.

The pA$_2$ and K$_D$ values obtained for Antibody 12 GL IgG1TM using the KG-1 cell-based assay are summarised in table 6.

2.13 Analysis of Binding Specificity of Antibody 8 GL and Antibody 12 GL Using Surface Plasmon Resonance (SPR) Biosensor The BIAcore 2000 or T-100 (GE Healthcare) biosensor instruments were used to assess the specificity of interaction between anti-IL-18 antibodies, Antibody 8 GL and Antibody 12 GL, and a range of recombinantly expressed IL-18 and related proteins.

As detailed previously (section 1.9), the binding interaction between each IgG and the different analytes were estimated using assays in which the IgG was covalently coupled to a CM5 chip by amine-linkage and the recombinant proteins passed over the chip surface. Antibody 8 GL and Antibody 12 GL found to bind to human and Rhesus macaque Il-18 but showed no binding to mouse IL-18, rat IL-18, human IL-1F7 or human IL-1β (Table 7).

2.14 Characterisation of Antibody 12 GL in an IL-18BP Epitope Competition Assay

A dilution series of purified Antibody 12 GL IgG$_2$ was prepared to determine if the antibody could inhibit the binding interaction between IL-18 and IL-18BP and thus indicate that Antibody 12 GL bound to the same conformational epitope as IL-18BP on recombinant human IL-18. The assay was set up as described in section 1.10.

Results were calculated using the same equations described in sections 1.3 and 1.4.

Figure 11:
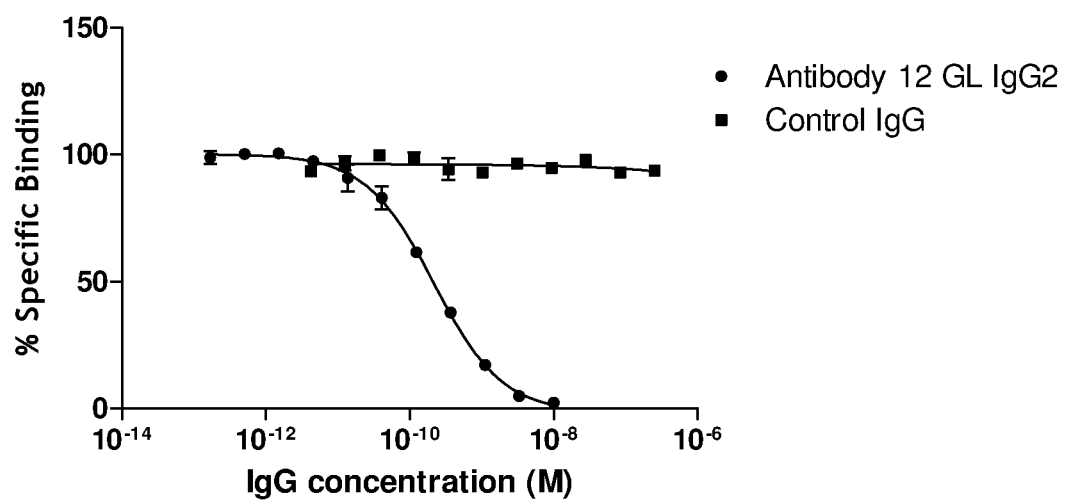
FIG. 11 shows the inhibition of human IL-18BPa-Fc binding to human IL-18-FH by increasing concentrations of Antibody 12 GL IgG$_2$ (circles). The Y axis represents the specific binding of the IL-18 to IL-18BPa-Fc as a percentage of the total binding observed in the absence of any IgG. Data represent mean values of duplicate points with SEM.

As exemplified in FIG. 11, Antibody 12 GL IgG$_2$ generated an IC$_{50}$ of 0.2 nM (95% CI: 0.1-0.4 nM, n=4).

2.15 Inhibition by Antibody 12 GL IgG$_1$TM of IL-18 Binding to IL-18BP

The assessment of the competition between Antibody 12 GL IgG$_1$TM and IL-18BP for the binding to human IL-18 was further evaluated using a ProteOn XPR instrument (Bio-Rad, Hercules Calif.), which operates in a maner similar to that of the Biacore2000 or T100. In this experiment amine linked surfaces of 3 different densities (range 230-6340 RUs) of either Antibody 12 GL IgG$_1$TM or IL-18BPa-Fc (R&D Systems, Minneapolis Minn.; cat. #119-BP) were allowed to capture Human IL-18 (in house, E. coli-derived) from a 100 nM solution (final densities of between 10 RUs and 330 RUs) and then stabilise. After that, further antibody 12 GL IgG$_1$TM and IL-18BP at 100 nM were passed over the captured IL-18 and the resulting sensorgrams inspected to determine if they was any binding to the IL-18. No further binding was observed in any of the combinations of the antibody 12 GL IgG$_1$TM or IL-18BPa-Fc. This provides indication that antibody 12 GL IgG$_1$TM and IL-18BPa have overlapping epitopes on IL-18.

Example 3

Crystallographic Studies 3.1 Purification of Human IL-18 and Antibody 12 GL Fab Fragment The human IL-18 construct, His-GST-IL-18 mentioned in section 1.1 underwent soluble expression in E. coli. The protein was purified by standard affinity chromatography followed by Factor Xa cleavage. The cleaved protein was then purified by anion exchange chromatography and standard affinity chromatography to remove any contaminating cleaved tag, the protein was then concentrated using a centrifugal concentrating device for crystallography.

The antibody 12 GL IgG was purified from conditioned media by adsorption to and elution from MabSelect SuRe Protein A (GE Healthcare). The purified antibody 12 GL (+30 mM cysteine) was incubated in papain (Sigma-Aldrich, St Louis Mo.) in phosphate-buffered saline, pH 7.2 containing 30 mM cysteine at a ratio of 5 mg of papain to 100 mg of IgG to produce Fab fragment. After incubation for 96 minutes, the digest was terminated by addition of iodoacetamide to a final concentration of 50 mM. The Fab fragment was purified by applying the digest to MabSelect SuRe Protein A (GE Healthcare), at pH 7.2, followed by collection of the unbound Fab fragment. After concentration the Fab was buffer exchanged into 50 mM sodium acetate, 30 mM sodium chloride+2% w/v sorbitol, pH 5.50 using a desalting PD-10 column (GE Healthcare).

3.2 IL-18 and Antibody 12 GL Fab Complex Formation

Antibody 12 GL Fab and human IL-18 (in house, E. coli-derived) were mixed in a 1:1 molar ratio (with a slight excess of IL-18) and gently stirred at +4° C. overnight. The formed complex was separated from excess IL-18 by size exclusion chromatography on a HiLoad Superdex 75 pg 26/60 column (GE Healthcare) equilibrated in 20 mM HEPES, pH 7.5, 150 mM NaCl at 2.5 mL/min. The complex was eluted as a single peak and was collected and concentrated to 10 mg/mL using an Amicon centrifuge device with MWCO of 10 kDa.

3.3 Crystallisation, Data Collection and Structure Determination

Extensive vapour diffusion crystallisation trials were set up with the IL-18:antibody 12 GL Fab complex at a concentration of 15 mg/mL in protein buffer (20 mM HEPES pH 7.5, 150 mM NaCl) to identify crystallisation conditions. The protein was centrifugated before setting up sitting drops in Intelli-plate Flat ledge (Art Robbins) with 100 mL protein solution and 100 mL well solution. The first crystals appeared within a couple of weeks in drops containing either ethanol, 3-Methyl-1,5-pentadiol (MPD) or both. The crystals appeared as needles or bundles of needles, not useful for diffraction experiments. The crystals were confirmed to be protein by UV microscopy.

Seeding was used throughout the optimisation of crystallisation conditions. In order to obtain crystals that were tested for diffraction, several rounds of micro- and macro-seeding were performed. A seed stock for micro-seeding was obtained by crushing crystals in 30 μL of well solution. The seed stock was diluted and various dilutions were added to the crystallisation drops, e.g. 10 nL of dilute seed stock to a 200 nL drop. Macro seeding was also used, breaking bundles of needle like crystals into smaller pieces and transferring them to fresh crystallisation drops.

The crystals used for data collection were obtained from hanging drops in Nextal plates (Qiagen), with 500 μL well solution containing 35-40% ethanol at +20° C. Macro-seeding was used, transferring pieces of crystals to fresh 3 μL crystallisation drops containing protein and well solution in a 1:1 ratio. The best crystals appeared in the macro-seeded drop, but were probably the result of small nuclei rather than the larger pieces. The resulting rod-shaped crystals of approximately 200 μm were sent to the European Synchrotron Radiation Facility (ESRF) in Grenoble, France for remote data collection. Data was collected to 2.5 Å from a single crystal at 100 K. on an ADSC Q315R detector at the ID23-1 beam line at the ESRF.

Data was collected from a single crystal at 100 K. The dataset was integrated using MOSFLM (Leslie, A (1991) Crystallographic computing V pp. 27-38) and scaled with Scala (CCP4 suite). Data collection statistics are shown in table 8. The crystal belonged to spacegroup P3121 with the cell dimensions a=b=95.1, c=316.9, α=β=90, γ=120. The asymmetric unit contains 2 copies of the IL-18-Fab complex, which gives a Matthew's coefficient of 3.1 and a solvent content of 60%.

The structure of the IL-18:antibody 12 GL Fab complex was determined by the molecular replacement method using the program Phaser (CCP4 Suite 1994) with search models for IL-18 and antibody 12 GL Fab derived from the Protein Data Bank entries 3F62 (Krumm et al (2008) PNAS 105(52): 20711-20715) and 1AQK (Faber et al (1998) Immunotechnology 3:253-370), respectively.

The initial search model (1AQK_variable) contained the Fab variable domains from 1AQK (heavy chain residues 2-122, light chain 2-111) with the following loops removed: LC 93-99, HC 27-32, 51-58, 73.76, and 101-107. Phaser gave a single solution in space group P3121. One copy of this model was found, and while keeping this solution fixed, the IL-18 search model extracted from 3F62 (IL-18:IL-18BP complex) with one loop removed (54-61) was placed next. This solution was locked and a successful search was made for the antibody 12 GL Fab constant domains from 1AQK (LC residues 112-216 and HC 123-226). A second copy of the IL-18: antibody 12 GL Fab (1AQK_variable) complex was placed in the asymmetric unit. The constant domain from 1AQK HC (heavy chain 123-226) was searched for and found. However, Phaser failed to identify the position of the Fab LC constant. The model was run in autobuster (Global phasing) rigid body refinement. The resulting maps were of good quality and the antibody 12 GL Fab side chains were remodelled in the program Coot (Emsley P. et al (2010) Acta Cryst D66:486-501) to sequence and missing loops were rebuilt by hand using the Coot program to match the Antibody 12 GL sequence. The missing loops were built into the difference density maps in Coot. After additional cycles of autobuster refinement the last LC constant domain in the second molecule had to be placed by hand in Coot. The Fab chains were numbered according to the Kabat numbering (Kabat et al (1991) Sequences of Proteins of Immunological Interest, 5th ed. Bethesda, Md.: National Center for Biotechnology Information, National Library of Medicine). The complete model was refined with the program Refmac5 (CCP4 suite 1994) to a final R factor 24.5% and a Free R factor of 28.6%.

3.4 Crystal Structure of IL-18:Antibody 12 GL Fab Complex

Crystals of the human IL-18:Antibody 12 GL complex were obtained in space group P3121. The overall quality of the electron density maps was good and allowed unambiguous modelling of 97% of the residues. Especially the epitope and paratope regions were well defined. The final model of IL-18 contains residues 1-156. Two loop regions were disordered in the electron density (residues 33-41 and 131-132) and parts of these were excluded from the model. The same loops are excluded from the model of the published crystal structure of IL-18 in complex with IL-18BP from ectovirus (PDB accession code 3F62; Krumm et al 2008 supra) and are reported to be highly flexible in the solution structure of unbound IL-18 (PDB code 1JOS; Kato et al (2003) Nat Struct Biol 10(11):966-971). The final model of the Antibody 12 GL Fab consists of light chain (LC) residues 1-213 (1-212 for the second molecule in the asymmetric unit) and heavy chain (HC) 1-226. The final model contains two copies of the IL-18-antibody 12 GL Fab complex and 79 water molecules.

Figure 12:
FIG. 12 shows a complex of IL-18:Antibody 12 GL in which polypeptide chains of IL-18 (grey) complex with Antibody 12 GL (black).

The crystal structure shows that each IL-18 molecule is bound to one Antibody 12 GL Fab fragment (FIG. 12). This crystal structure allows the epitope interactions between IL-18 and Antibody 12 GL to be examined in atomic detail. These are captured in Table 9, where the residue number contains a chain indicator (H: Antibody 12 GL Heavy chain, L: Antibody 12 GL Light chain). The distances were obtained using the CCP4 program CONTACT (CCP4, 1994). It is only necessary to describe one of the two complexes, since they are equivalent. The interactions involve the complementarity determining regions (CDRs) from both the heavy and the light chain of the antibody fragment. The amino acid residues in IL-18 that form part of the epitope are Tyr1, Gly3, Leu5, Glu6, Lys8, Met51, Lys53, Asp54, Ser55, Gln56, Pro57, Arg58, Gly59, Met60, Arg104, Ser105 and Pro107. Residues contributed from the Antibody 12 GL light chain are Gly28, Ser30, Trp32, Ser91, His92, His93 and Pro94. There is a single amino acid contribution from light chain framework 1, residue Asp1. Residues contributed from the heavy chain are Tyr35, Tyr52, Tyr53, Tyr58, Ala97, Tyr98, Phe99, Gly100, Thr100D and Asp100E.

The overall structure of IL-18 is highly similar to the IL-18 from the IL-18:IL-18BP complex (3F62; Krumm et al 2008 supra) with an overall Cα root mean square deviation of 0.87 Å2. There is, however, a 3 Å positional shift of one loop (residues 55-59) compared to the IL-18:IL-18BP complex. Despite this shift, the overall conformation of the loop, that is bearing a large number of interaction points with the paratope, is still quite similar. On the contrary, the conformation of the loop (55-59) deviates a lot from the reported NMR solution structure of unbound IL-18 (Kato et al 2003 supra) as well as the crystal structure of IL-18:125-2H complex (Argiriadi, M. A. et al (2009) JBC 284: 24478-24489), with a maximum shift of 5 Å and 7 Å respectively. The binding mode of Antibody 12 GL overlaps almost completely with IL-18BP from ecto virus, as shown in a recently published crystal structure (Krumm et al 2008 supra). The crystal structure of an IL-18:Antibody 12 GL Fab complex, reveals that there is essentially no overlap between the 125-2H (2VXT; Argiriadi et al 2009 supra) and Antibody 12 GL epitopes.

With regards to species cross-reactivity, Antibody 12 GL is not cross-reactive with mouse IL-18 but is with cynomolgus IL-18. Cynomolgus monkey and human IL-18 epitopes are 100% identical.

Example 4

Free IL-18 Assay

The concentration of free IL-18 was determined with an electroluminescent (ECL) immunoassay.

Figure 16:
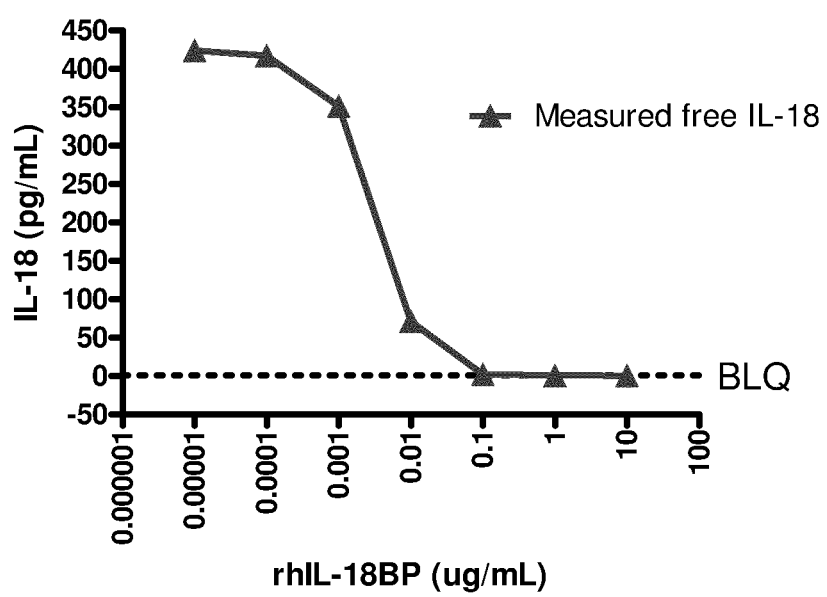
FIG. 16 shows the concentration dependent inhibition of the signal from recombinant IL-18 in an assay for free IL-18 with recombinant IL-18BP.
Figure 17:
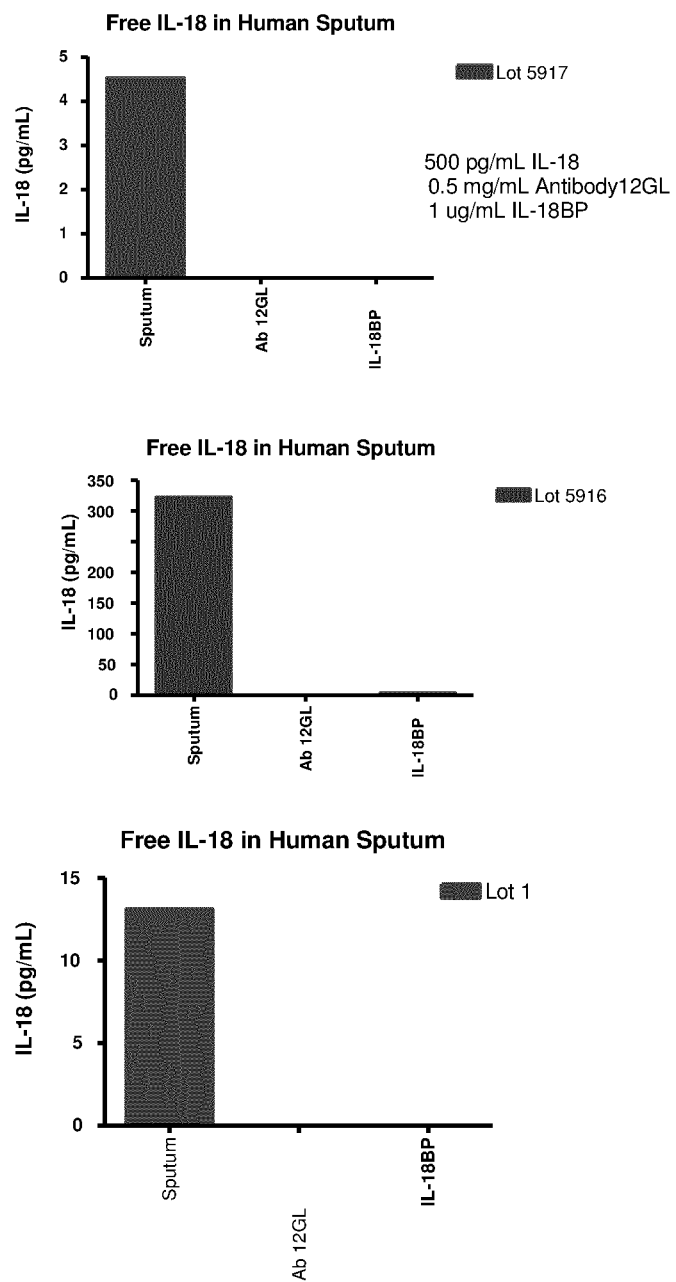
FIG. 17 shows the inhibition by recombinant IL-18BP and Antibody 12 GL of signal from endogenous free IL-18 in three human sputum samples in an assay for free IL-18.

Antibody 12GL at a concentration of 0.625 µg/ml was coated overnight onto the carbon electrode of a 96-well plate (Standard Plate, Mesoscale Discovery). Wells were washed and subsequently incubated with I-Block buffer (Tropix) for 1 to 3 hours. Standard and QC concentrations were prepared from recombinant human IL-18 (R&D Systems) in I-Block buffer. Wells were washed and standards, QC's, and undiluted test sample were incubated for 30 min at room temperature. Wells were washed and 0.5 µg/ml biotinylated detection antibody (MBL International) was added to wells. After 1 hour incubation, wells were washed, and Streptavidin-SulfoTag (Mesoscale Discovery) was added to each well. After an incubation time of 30 min, wells were washed and Read Buffer (Mesoscale Discovery) was added to each well. The ECL signal was read on a Sector Imager2400 (Mesoscale Discovery). The results are shown in FIGS. 16 and 17.

TABLE 1

Example potencies of improved scFv clones when tested in the IFNγ release KG-1 cell assay.

| | IC$_{50}$ (nM) | |
|---|---|---|
| Clone (scFv) | Human IL-18 | Rhesus Macaque IL-18 |
| Antibody 2 | 106.8 (n = 2) | |
| Antibody 3 | 44.4 (n = 2) | |
| Antibody 4 | 50 (n = 2) | |
| Antibody 5 | 45.1 (27.4-74.2; n = 3) | |
| Antibody 6 | 11.6 (4.8-28.2; n = 5) | 65.7 (20.2-213; n = 4) |
| Antibody 7 | 6.1 (3.8-9.6; n = 7) | 24.9 (11.0-56.3; n = 5) |
| Antibody 9 | 0.714 (n = 2) | 2.174 (n = 2) |
| Antibody 10 | 0.977 (n = 2) | 2.924 (n = 2) |

Data are expressed as Geometric mean (95% confidence intervals; n)

TABLE 2

Example potencies of improved IgG$_2$ when tested in the IFNg release KG-1 cell assay.

| | IC$_{50}$ (nM) | |
|---|---|---|
| Clones | Human IL-18 | Rhesus Macaque IL-18 |
| Antibody 2 IgG$_2$ | 5 (n = 1) | 33 (n = 1) |
| Antibody 3 IgG$_2$ | 4.1 (n = 1) | 21 (n = 1) |
| Antibody 4 IgG$_2$ | 6.6 (n = 1) | 35 (n = 1) |
| Antibody 5 IgG$_2$ | 5.4 (n = 1) | 30 (n = 1) |
| Antibody 9 IgG$_2$ | 0.166 (0.1-0.275; n = 4) | 0.212 (0.141-0.319; n = 3) |
| Antibody 10 IgG$_2$ | 0.220 (0.112-0.433; n = 4) | 0.338 (0.161-0.713; n = 3) |
| Antibody 11 IgG$_2$ | 0.260 (0.06-1.115; n = 3) | 0.444 (n = 2) |

Data are expressed as Geometric mean (95% confidence intervals; n)

TABLE 3

Example potency data for germlined optimised clones when evaluated in the IFNγ release KG-1 cell assay.

| Clones (germlined IgG) | IC$_{50}$ (nM) | |
|---|---|---|
| | Human IL-18 | Rhesus Macaque IL-18 |
| Antibody 1 GL IgG$_2$ | 159 (n = 1) | |
| Antibody 6 GL IgG$_2$ | 0.535 (0.257-1.115; n = 3) | 9.9 (n = 2) |
| Antibody 7 GL IgG$_2$ | 0.314 (0.268-0.369; n = 4) | 2.497 (1.169-5.332; n = 4) |
| Antibody 8 GL IgG$_2$ | 0.444 (0.323-0.610; n = 11) | 1.517 (1.166-1.974; n = 9) |
| Antibody 11 GL IgG$_2$ | 0.194 (0.137-0.274; n = 6) | 0.276 (0.185-0.409; n = 5) |
| Antibody 12 GL IgG$_2$ | 0.202 (0.142-0.288; n = 6) | 0.285 (0.187-0.436; n = 5) |
| Antibody 12 GL IgG$_1$TM | 0.080 (0.063-0.1, 8) | 0.461 (0.317-0.670, 8) |

Data are expressed as Geometric mean (95% confidence intervals; n)

TABLE 4

Example potency data for germlined optimised clones when evaluated in the IFNγ release PBMC cell assay.

| Clone (germlined IgG) | IC$_{50}$ (nM) | |
|---|---|---|
| | Human PBMC | Cynomolgus monkey PBMC |
| Antibody 8 GL IgG$_2$ | 0.51 (n = 1) | Not tested |
| Antibody 11 GL IgG$_2$ | 0.25 (n = 1) | Not tested |
| Antibody 12 GL IgG$_2$ | 0.32 (n = 1) | Not tested |
| Antibody 12 GL IgG$_1$TM | 0.15 (0.06-0.39, n = 3) | 0.28 (0.10-0.79, n = 3) |

Data are expressed as Geometric mean (95% confidence intervals; number of PBMC donors tested)

TABLE 5

Kinetic analysis of Antibody 8 GL and Antibody 12 GL to recombinant Human and Rhesus Macaque IL-18.

| | Human IL-18 | | | Rhesus m. IL-18 | | |
|---|---|---|---|---|---|---|
| Clone | K-on (1/Ms) | K-off (1/s) | KD (pM) | K-on (1/Ms) | K-off (1/s) | KD (pM) |
| Antibody 8 GL IgG$_2$ | 5.0 × 10$^5$ | 5.49 × 10$^{-5}$ | 110 | 4.36 × 10$^6$ | 7.08 × 10$^{-5}$ | 163 |
| Antibody 12 GL IgG$_2$ | 8.85 × 10$^5$ | 8.16 × 10$^{-5}$ | 92 | 1.05 × 10$^6$ | 4.79 × 10$^{-5}$ | 46 |
| Antibody 12 GL IgG$_1$TM | 4.6 × 10$^5$ | 2.9 × 10$^{-5}$ | 62.9 | 6.3 × 10$^5$ | 3.5 × 10$^{-5}$ | 54.7 |

TABLE 6

Example Antibody 12GL IgG$_1$TM pA2 and KD values in the KG-1 cell assay using either human IL-18 or rhesus macaque IL-18.

| Ligand | pA$_2$ | KD (pM) |
|---|---|---|
| Human IL-18 | −10.15 (−10.25 to −10.5; n = 7) | 71 (56 to 90; n = 7) |
| Rhesus macaque IL-18 | −9.85 (−10.34 to −9.35; n = 4) | 142 (46 to 440; n = 4) |

Data are expressed as Geometric mean (95% confidence intervals; number of experiments)

TABLE 7

Specificity analysis of anti-IL-18 IgG Antibody 8 GL and Antibody 12 GL using SPR. The resulting observed responses were compared to the response of buffer alone and assessed as either indicating binding (+) or no binding (−).

| Clones | Analyte | Binding |
|---|---|---|
| Antibody 8 GL IgG$_2$ | Human IL-18 | + |
| | Rhesus Macaque IL-18 | + |
| | Rat IL-18 | − |
| | Mouse IL-18 | Not determined |
| | Human IL-1β | − |
| | Human IL-1F7/FIL1zeta | − |
| Antibody 12 GL IgG$_2$ | Human IL-18 | + |
| | Rhesus Macaque IL-18 | + |
| | Rat IL-18 | − |
| | Mouse IL-18 | − |
| | Human IL-1F7/FIL1zeta | − |
| | Human IL-1β | − |
| Antibody 12 GL IgG$_1$TM | Human IL-18 | + |
| | Rhesus Macaque IL-18 | + |
| | Rat Il-18 | − |
| | Mouse IL-18 | − |
| | Human IL-1F7/FIL1zeta | Not determined |
| | Human IL-1β | Not determined |

TABLE 8

Crystallographic and refinement details of IL-18: Antibody 12 GL.

Crystallographic and refinement details

| | |
|---|---|
| Space group | P3121 |
| Cell parameters | a = 95.10 b = 95.10 c = 316.10, a = b = 90.0 g = 120.0 |
| Number of molecules/a.u. | 2 |
| Number of reflections | |
| Total | 327931 |
| Unique | 46619 |
| Resolution (Å) | 50-2.70 (2.77-2.70)[a] |
| Multiplicity | 7.1 (7.3)[a] |
| MnI/σ | 14.5 (3.5)[a] |
| Completeness (%) | 99.8 (99.6)[a] |
| Rmerge (%) | 9.8 (71.1)[a] |
| Mosaicity | 0.7 |
| R factor (%) | 24.65 |
| Free R factor (%) | 28.66 |
| Number of water molecules | 79 |
| r.m.s.d. from ideal values | |
| Bond lengths (Å) | 0.008 |
| Bond angles (°) | 1.00 |
| Average B factors (Å$^2$) | |
| IL18 main chain atoms | 62.4 |
| IL18 all atoms | 62.4 |
| Fab HC[b] main chain atoms | 41.5 |
| Fab HC[b] all atoms | 41.5 |
| Fab LC[b] main chain atoms | 48.0 |
| Fab LC[b] all atoms | 47.9 |
| Water molecules | 39.5 |

[a]Number in parenthesis is referring to the outer resolution shell
[b]HC = heavy chain, LC = light chain

TABLE 9

Details of IL-18: Antibody 12 GL crystal structure.
Distances measured between residues involved in IL18: Antibody 12 GL Fab interaction (less than 4 Å). The shortest measured distance between two residues is given. Maximal estimated error (SFcheck) = 0.202.

| Residue IL18 | Residue Fab | Chain Fab | Distance (Å) | Comment |
|---|---|---|---|---|
| Hydrogen bond distances (2.4-3.2 Å) | | | | |
| Lys A 53 NZ | Ser L 91 O | LC | 2.6 | |
| Lys A 53 NZ | His L 92 O | LC | 2.6 | |
| Lys A 53 NZ | Asp H 100E OD | HC | 2.9 | |
| Pro A 57 O | Tyr H 52 OH | HC | 2.5 | |
| Arg 58 O | Tyr 58 OH | HC | 3.2 | |
| Arg 104 NE | Tyr 58 OH | HC | 3.0 | |
| Ser A 105 OG | Asp L 1 N | LC | 2.8 | |
| Interactions <4 Å | | | | |
| Tyr 1 | Tyr 98 | HC | 3.6 | |
| Tyr 1 | Phe 99 | HC | 3.5 | |
| Tyr 1 | Gly 100 | HC | 3.8 | |
| Gly 3 | Tyr 98 | HC | 3.7 | |
| Leu 5 | Trp 32 | LC | 3.7 | |
| Glu 6 | Ser 30 | LC | 3.8* | Poor electron density for side chain |
| Met 51 | His 92 | LC | 3.4 | Poor electron density for side chain. |
| Asp 54 | Tyr 98 | HC | 3.7 | |
| Lys 53 | Thr 100D | HC | 4.1* | |
| Lys 53 | Tyr 98 | HC | 3.4 | |
| Lys 53 | Trp 32 | LC | 3.6 | |
| Ser 55 | Tyr 98 | HC | 3.4 | |
| Ser 55 | Phe 99 | HC | 3.7 | |
| Ser 55 | Ala 97 | HC | 3.3 | |
| Ser 55 | Tyr 35 | HC | 4.1 | |
| Gln 56 | Tyr 53 | HC | 3.4 | |
| Gln 56 | Tyr 52 | HC | 3.3* | |
| Pro 57 | Tyr 35 | HC | 3.7 | |
| Pro 57 | Tyr 58 | HC | 3.5 | |
| Pro 57 | Pro 94 | LC | 3.5 | |
| Pro 57 | Trp 96 | LC | 3.7 | |
| Pro 57 | Asp 100E | HC | 4.0 | |
| Gly 59 | Tyr 58 | HC | 3.7 | |
| Gly 59 | His 93 | LC | 3.6 | |
| Gly 59 | Pro 94 | LC | 3.5 | |
| Met 60 | His 92 | LC | 3.7 | |
| Met 60 | His 93 | LC | 3.7 | |

*the variation between the two molecules in the asymmetric unit is more than 0.25 Å

TABLE 10 correspondence between the sequences in the Sequence Listing below and the VH domains, VL domains, CDRs and framework regions of the antibodies described herein.

| | | |
|---|---|---|
| SEQ ID NO: 1 | Antibody 1 | VH DNA |
| SEQ ID NO: 2 | Antibody 1 | VH PRT |
| SEQ ID NO: 3 | Antibody 1 | HCDR1 PRT |
| SEQ ID NO: 4 | Antibody 1 | HCDR2 PRT |
| SEQ ID NO: 5 | Antibody 1 | HCDR3 PRT |
| SEQ ID NO: 6 | Antibody 1 | VL DNA |
| SEQ ID NO: 7 | Antibody 1 | VL PRT |
| SEQ ID NO: 8 | Antibody 1 | LCDR1 PRT |
| SEQ ID NO: 9 | Antibody 1 | LCDR2 PRT |
| SEQ ID NO: 10 | Antibody 1 | LCDR3 PRT |
| SEQ ID NO: 11 | Antibody 1 GL | VH DNA |
| SEQ ID NO: 12 | Antibody 1 GL | VH PRT |
| SEQ ID NO: 13 | Antibody 1 GL | HCDR1 PRT |
| SEQ ID NO: 14 | Antibody 1 GL | HCDR2 PRT |
| SEQ ID NO: 15 | Antibody 1 GL | HCDR3 PRT |
| SEQ ID NO: 16 | Antibody 1 GL | VL DNA |
| SEQ ID NO: 17 | Antibody 1 GL | VL PRT |
| SEQ ID NO: 18 | Antibody 1 GL | LCDR1 PRT |
| SEQ ID NO: 19 | Antibody 1 GL | LCDR2 PRT |
| SEQ ID NO: 20 | Antibody 1 GL | LCDR3 PRT |
| SEQ ID NO: 21 | Antibody 2 | VH DNA |
| SEQ ID NO: 22 | Antibody 2 | VH PRT |
| SEQ ID NO: 23 | Antibody 2 | HCDR1 PRT |
| SEQ ID NO: 24 | Antibody 2 | HCDR2 PRT |
| SEQ ID NO: 25 | Antibody 2 | HCDR3 PRT |
| SEQ ID NO: 26 | Antibody 2 | VL DNA |
| SEQ ID NO: 27 | Antibody 2 | VL PRT |
| SEQ ID NO: 28 | Antibody 2 | LCDR1 PRT |
| SEQ ID NO: 29 | Antibody 2 | LCDR2 PRT |
| SEQ ID NO: 30 | Antibody 2 | LCDR3 PRT |
| SEQ ID NO: 31 | Antibody 3 | VH DNA |
| SEQ ID NO: 32 | Antibody 3 | VH PRT |
| SEQ ID NO: 33 | Antibody 3 | HCDR1 PRT |
| SEQ ID NO: 34 | Antibody 3 | HCDR2 PRT |
| SEQ ID NO: 35 | Antibody 3 | HCDR3 PRT |
| SEQ ID NO: 36 | Antibody 3 | VL DNA |
| SEQ ID NO: 37 | Antibody 3 | VL PRT |
| SEQ ID NO: 38 | Antibody 3 | LCDR1 PRT |
| SEQ ID NO: 39 | Antibody 3 | LCDR2 PRT |
| SEQ ID NO: 40 | Antibody 3 | LCDR3 PRT |
| SEQ ID NO: 41 | Antibody 4 | VH DNA |
| SEQ ID NO: 42 | Antibody 4 | VH PRT |
| SEQ ID NO: 43 | Antibody 4 | HCDR1 PRT |
| SEQ ID NO: 44 | Antibody 4 | HCDR2 PRT |

TABLE 10-continued correspondence between the sequences in the Sequence Listing below and the VH domains, VL domains, CDRs and framework regions of the antibodies described herein.

| | | |
|---|---|---|
| SEQ ID NO: 45 | Antibody 4 | HCDR3 PRT |
| SEQ ID NO: 46 | Antibody 4 | VL DNA |
| SEQ ID NO: 47 | Antibody 4 | VL PRT |
| SEQ ID NO: 48 | Antibody 4 | LCDR1 PRT |
| SEQ ID NO: 49 | Antibody 4 | LCDR2 PRT |
| SEQ ID NO: 50 | Antibody 4 | LCDR3 PRT |
| SEQ ID NO: 51 | Antibody 5 | VH DNA |
| SEQ ID NO: 52 | Antibody 5 | VH PRT |
| SEQ ID NO: 53 | Antibody 5 | HCDR1 PRT |
| SEQ ID NO: 54 | Antibody 5 | HCDR2 PRT |
| SEQ ID NO: 55 | Antibody 5 | HCDR3 PRT |
| SEQ ID NO: 56 | Antibody 5 | VL DNA |
| SEQ ID NO: 57 | Antibody 5 | VL PRT |
| SEQ ID NO: 58 | Antibody 5 | LCDR1 PRT |
| SEQ ID NO: 59 | Antibody 5 | LCDR2 PRT |
| SEQ ID NO: 60 | Antibody 5 | LCDR3 PRT |
| SEQ ID NO: 61 | Antibody 6 | VH DNA |
| SEQ ID NO: 62 | Antibody 6 | VH PRT |
| SEQ ID NO: 63 | Antibody 6 | HCDR1 PRT |
| SEQ ID NO: 64 | Antibody 6 | HCDR2 PRT |
| SEQ ID NO: 65 | Antibody 6 | HCDR3 PRT |
| SEQ ID NO: 66 | Antibody 6 | VL DNA |
| SEQ ID NO: 67 | Antibody 6 | VL PRT |
| SEQ ID NO: 68 | Antibody 6 | LCDR1 PRT |
| SEQ ID NO: 69 | Antibody 6 | LCDR2 PRT |
| SEQ ID NO: 70 | Antibody 6 | LCDR3 PRT |
| SEQ ID NO: 71 | Antibody 6 GL | VH DNA |
| SEQ ID NO: 72 | Antibody 6 GL | VH PRT |
| SEQ ID NO: 73 | Antibody 6 GL | HCDR1 PRT |
| SEQ ID NO: 74 | Antibody 6 GL | HCDR2 PRT |
| SEQ ID NO: 75 | Antibody 6 GL | HCDR3 PRT |
| SEQ ID NO: 76 | Antibody 6 GL | VL DNA |
| SEQ ID NO: 77 | Antibody 6 GL | VL PRT |
| SEQ ID NO: 78 | Antibody 6 GL | LCDR1 PRT |
| SEQ ID NO: 79 | Antibody 6 GL | LCDR2 PRT |
| SEQ ID NO: 80 | Antibody 6 GL | LCDR3 PRT |
| SEQ ID NO: 81 | Antibody 7 | VH DNA |
| SEQ ID NO: 82 | Antibody 7 | VH PRT |
| SEQ ID NO: 83 | Antibody 7 | HCDR1 PRT |
| SEQ ID NO: 84 | Antibody 7 | HCDR2 PRT |
| SEQ ID NO: 85 | Antibody 7 | HCDR3 PRT |
| SEQ ID NO: 86 | Antibody 7 | VL DNA |
| SEQ ID NO: 87 | Antibody 7 | VL PRT |
| SEQ ID NO: 88 | Antibody 7 | LCDR1 PRT |
| SEQ ID NO: 89 | Antibody 7 | LCDR2 PRT |
| SEQ ID NO: 90 | Antibody 7 | LCDR3 PRT |
| SEQ ID NO: 91 | Antibody 7 GL | VH DNA |
| SEQ ID NO: 92 | Antibody 7 GL | VH PRT |
| SEQ ID NO: 93 | Antibody 7 GL | HCDR1 PRT |
| SEQ ID NO: 94 | Antibody 7 GL | HCDR2 PRT |
| SEQ ID NO: 95 | Antibody 7 GL | HCDR3 PRT |
| SEQ ID NO: 96 | Antibody 7 GL | VL DNA |
| SEQ ID NO: 97 | Antibody 7 GL | VL PRT |
| SEQ ID NO: 98 | Antibody 7 GL | LCDR1 PRT |
| SEQ ID NO: 99 | Antibody 7 GL | LCDR2 PRT |
| SEQ ID NO: 100 | Antibody 7 GL | LCDR3 PRT |
| SEQ ID NO: 101 | Antibody 8 GL | VH DNA |
| SEQ ID NO: 102 | Antibody 8 GL | VH PRT |
| SEQ ID NO: 103 | Antibody 8 GL | HCDR1 PRT |
| SEQ ID NO: 104 | Antibody 8 GL | HCDR2 PRT |
| SEQ ID NO: 105 | Antibody 8 GL | HCDR3 PRT |
| SEQ ID NO: 106 | Antibody 8 GL | VL DNA |
| SEQ ID NO: 107 | Antibody 8 GL | VL PRT |
| SEQ ID NO: 108 | Antibody 8 GL | LCDR1 PRT |
| SEQ ID NO: 109 | Antibody 8 GL | LCDR2 PRT |
| SEQ ID NO: 110 | Antibody 8 GL | LCDR3 PRT |
| SEQ ID NO: 111 | Antibody 9 | VH DNA |
| SEQ ID NO: 112 | Antibody 9 | VH PRT |
| SEQ ID NO: 113 | Antibody 9 | HCDR1 PRT |
| SEQ ID NO: 114 | Antibody 9 | HCDR2 PRT |
| SEQ ID NO: 115 | Antibody 9 | HCDR3 PRT |
| SEQ ID NO: 116 | Antibody 9 | VL DNA |
| SEQ ID NO: 117 | Antibody 9 | VL PRT |
| SEQ ID NO: 118 | Antibody 9 | LCDR1 PRT |
| SEQ ID NO: 119 | Antibody 9 | LCDR2 PRT |
| SEQ ID NO: 120 | Antibody 9 | LCDR3 PRT |
| SEQ ID NO: 121 | Antibody 10 | VH DNA |
| SEQ ID NO: 122 | Antibody 10 | VH PRT |
| SEQ ID NO: 123 | Antibody 10 | HCDR1 PRT |
| SEQ ID NO: 124 | Antibody 10 | HCDR2 PRT |
| SEQ ID NO: 125 | Antibody 10 | HCDR3 PRT |
| SEQ ID NO: 126 | Antibody 10 | VL DNA |
| SEQ ID NO: 127 | Antibody 10 | VL PRT |
| SEQ ID NO: 128 | Antibody 10 | LCDR1 PRT |
| SEQ ID NO: 129 | Antibody 10 | LCDR2 PRT |
| SEQ ID NO: 130 | Antibody 10 | LCDR3 PRT |
| SEQ ID NO: 131 | Antibody 11 | VH DNA |
| SEQ ID NO: 132 | Antibody 11 | VH PRT |
| SEQ ID NO: 133 | Antibody 11 | HCDR1 PRT |
| SEQ ID NO: 134 | Antibody 11 | HCDR2 PRT |
| SEQ ID NO: 135 | Antibody 11 | HCDR3 PRT |
| SEQ ID NO: 136 | Antibody 11 | VL DNA |
| SEQ ID NO: 137 | Antibody 11 | VL PRT |
| SEQ ID NO: 138 | Antibody 11 | LCDR1 PRT |
| SEQ ID NO: 139 | Antibody 11 | LCDR2 PRT |
| SEQ ID NO: 140 | Antibody 11 | LCDR3 PRT |
| SEQ ID NO: 141 | Antibody 11 GL | VH DNA |
| SEQ ID NO: 142 | Antibody 11 GL | VH PRT |
| SEQ ID NO: 143 | Antibody 11 GL | HCDR1 PRT |
| SEQ ID NO: 144 | Antibody 11 GL | HCDR2 PRT |
| SEQ ID NO: 145 | Antibody 11 GL | HCDR3 PRT |
| SEQ ID NO: 146 | Antibody 11 GL | VL DNA |
| SEQ ID NO: 147 | Antibody 11 GL | VL PRT |
| SEQ ID NO: 148 | Antibody 11 GL | LCDR1 PRT |
| SEQ ID NO: 149 | Antibody 11 GL | LCDR2 PRT |
| SEQ ID NO: 150 | Antibody 11 GL | LCDR3 PRT |
| SEQ ID NO: 151 | Antibody 12 GL | VH DNA |
| SEQ ID NO: 152 | Antibody 12 GL | VH PRT |
| SEQ ID NO: 153 | Antibody 12 GL | HCDR1 PRT |
| SEQ ID NO: 154 | Antibody 12 GL | HCDR2 PRT |
| SEQ ID NO: 155 | Antibody 12 GL | HCDR3 PRT |
| SEQ ID NO: 156 | Antibody 12 GL | VL DNA |
| SEQ ID NO: 157 | Antibody 12 GL | VL PRT |
| SEQ ID NO: 158 | Antibody 12 GL | LCDR1 PRT |
| SEQ ID NO: 159 | Antibody 12 GL | LCDR2 PRT |
| SEQ ID NO: 160 | Antibody 12 GL | LCDR3 PRT |
| SEQ ID NO: 161 | Germlined VH FW1 | |
| SEQ ID NO: 162 | Germlined VH FW2 | |
| SEQ ID NO: 163 | Germlined VH FW3 | |
| SEQ ID NO: 164 | Germlined VH FW4 | |
| SEQ ID NO: 165 | Germlined VL FW1 | |
| SEQ ID NO: 166 | Germlined VL FW2 | |
| SEQ ID NO: 167 | Germlined VL FW3 | |
| SEQ ID NO: 168 | Germlined VL FW4 | |
| SEQ ID NO: 169 | Human IL-18 | |
| SEQ ID NO: 170 | Antibody 12 GL | Optimised VH DNA |
| SEQ ID NO: 171 | Antibody 12 GL | Optimised VL DNA |

TABLE 11

SEQ ID NOS for the VH and VL domains and CDRs of the mAbs described herein

| Anti-body | VH | HCDR1 | HCDR2 | HCDR3 | VL | LCDR1 | LCDR2 | LCDR3 |
|---|---|---|---|---|---|---|---|---|
| 1 | 2 | 3 | 4 | 5 | 7 | 8 | 9 | 10 |
| 1_GL | 12 | 13 | 14 | 15 | 17 | 18 | 19 | 20 |
| 2 | 22 | 23 | 24 | 25 | 27 | 28 | 29 | 30 |

TABLE 11-continued

SEQ ID NOS for the VH and VL domains and CDRs of the mAbs described herein

| Anti-body | VH | HCDR1 | HCDR2 | HCDR3 | VL | LCDR1 | LCDR2 | LCDR3 |
|---|---|---|---|---|---|---|---|---|
| 3 | 32 | 33 | 34 | 35 | 37 | 38 | 39 | 40 |
| 4 | 42 | 43 | 44 | 45 | 47 | 48 | 49 | 50 |
| 5 | 52 | 53 | 54 | 55 | 57 | 58 | 59 | 60 |
| 6 | 62 | 63 | 64 | 65 | 67 | 68 | 69 | 70 |
| 6_GL | 72 | 73 | 74 | 75 | 77 | 78 | 79 | 80 |
| 7 | 82 | 83 | 84 | 85 | 87 | 88 | 89 | 90 |
| 7_GL | 92 | 93 | 94 | 95 | 97 | 98 | 99 | 100 |
| 8_GL | 102 | 103 | 104 | 105 | 107 | 108 | 109 | 110 |
| 9 | 112 | 113 | 114 | 115 | 117 | 118 | 119 | 120 |
| 10 | 122 | 123 | 124 | 125 | 127 | 128 | 129 | 130 |
| 11 | 132 | 133 | 134 | 135 | 137 | 138 | 139 | 140 |
| 11_GL | 142 | 143 | 144 | 145 | 147 | 148 | 149 | 150 |
| 12_GL | 152 | 153 | 154 | 155 | 157 | 158 | 159 | 160 |

TABLE 12

Sequence alignment of VH domains of the mAbs described herein

| VH | Kabat Numbering | FW1 | | | | | | | | | | | | | | | | | | | | |
|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Stella74 | Antibody 1 | Q | V | Q | L | Q | Q | S | G | P | R | L | V | K | P | S | Q | T | L | S | L | T | C |
| Stella74FGL | Antibody 1 GL | | | | | | E | | | | G | | | | | | E | | | | | | |
| LO740001 | Antibody 2 | | | | | | | | | | | | | | | | | | | | | | |
| LO740006 | Antibody 3 | | | | | | | | | | | | | | | | | | | | | | |
| LO740007 | Antibody 4 | | | | | | | | | | | | | | | | | | | | | | |
| LO740008 | Antibody 5 | | | | | | | | | | | | | | | | | | | | | | |
| LO740022 | Antibody 6 | | | | | | | | | | | | | | | | | | | | | | |
| LO740022FGL | Antibody 6 GL | | | | | | E | | | | G | | | | | | E | | | | | | |
| LO740029 | Antibody 7 | | | | | | | | | | | | | | | | | | | | | | |
| LO740029FGL | Antibody 7 GL | | | | | | E | | | | G | | | | | | E | | | | | | |
| LO740029ALGFGL | Antibody 8 GL | | | | | | E | | | | G | | | | | | E | | | | | | |
| LO740054 | Antibody 9 | | | | | | | | | | | | | | E | | | | | | | | |
| LO740059 | Antibody 10 | | | | | | | | | | | | | | E | | | | | | | | |
| LO740059ALG | Antibody 11 | | | | | | | | | | | | | | E | | | | | | | | |
| LO740054ALGFGL | Antibody 12 GL | | | | | | E | | | | G | | | | | | E | | | | | | |
| LO740059ALGFGL | Antibody 11 GL | | | | | | E | | | | G | | | | | | E | | | | | | |

| VH | Kabat Numbering | FW1 | | | | | | | | CDR1 | | | | | | | FW2 | | | | | |
|---|---|---|---|---|---|---|---|---|---|---|---|---|---|---|---|---|---|---|---|---|---|---|
| | | 23 | 24 | 25 | 26 | 27 | 28 | 29 | 30 | 31 | 32 | 33 | 34 | 35 | 35a | 35b | 36 | 37 | 38 | 39 | 40 | 41 | 42 |
| Stella74 | Antibody 1 | T | V | S | G | G | S | I | S | S | G | G | Y | Y | W | S | W | I | R | Q | P | A | G |
| Stella74FGL | Antibody 1 GL | | | | | | | | | | | | | | | | | | | | | P | |
| LO740001 | Antibody 2 | | | | | | | | | | | | | | | | | | | | | | |
| LO740006 | Antibody 3 | | | | | | | | | | | | | | | | | | | | | | |
| LO740007 | Antibody 4 | | | | | | | | | | | | | | | | | | | | | | |
| LO740008 | Antibody 5 | | | | | | | | | | | | | | | | | | | | | | |
| LO740022 | Antibody 6 | | | | | | | | | | | | | | | | | | | | | | |
| LO740022FGL | Antibody 6 GL | | | | | | | | | | | | | | | | | | | | | P | |
| LO740029 | Antibody 7 | | | | | | | | | | | | | | | | | | | | | | |
| LO740029FGL | Antibody 7 GL | | | | | | | | | | | | | | | | | | | | | P | |
| LO740029ALGFGL | Antibody 8 GL | | | | | | | | | | A | | | | | | | | | | | P | |
| LO740054 | Antibody 9 | | | | | | | | | | D | | | | | | | | | | | | |
| LO740059 | Antibody 10 | | | | | | | | | | D | | | | | | | | | | | | |
| LO740059ALG | Antibody 11 | | | | | | | | | A | D | | | | | | | | | | | | |
| LO740054ALGFGL | Antibody 12 GL | | | | | | | | | A | D | | | | | | | | | | | P | |
| LO740059ALGFGL | Antibody 11 GL | | | | | | | | | A | D | | | | | | | | | | | P | |

TABLE 12-continued

Sequence alignment of VH domains of the mAbs described herein

| VH | Kabat Numbering | FW2 | | | | | | | CDR2 | | | | | | | | | | | | | | | |
|---|---|---|---|---|---|---|---|---|---|---|---|---|---|---|---|---|---|---|---|---|---|---|---|---|
| | | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 |
| Stella74 | Antibody 1 | K | G | L | E | W | I | G | S | I | Y | Y | S | G | S | T | Y | Y | N | P | S | L | K | S |
| Stella74FGL | Antibody 1 GL | | | | | | | | | | | | | | | | | | | | | | | |
| LO740001 | Antibody 2 | | | | | | | | | | | | | | | | | | | | | | | |
| LO740006 | Antibody 3 | | | | | | | | | | | | | | | | | | | | | | | |
| LO740007 | Antibody 4 | | | | | | | | | | | | | | | | | | | | | | | |
| LO740008 | Antibody 5 | | | | | | | | | | | | | | | | | | | | | | | |
| LO740022 | Antibody 6 | | | | | | | | | | | | | | | | | | | | | | | |
| LO740022FGL | Antibody 6 GL | | | | | | | | | | | | | | | | | | | | | | | |
| LO740029 | Antibody 7 | | | | | | | | | | | | | | | | | | | | | | | |
| LO740029FGL | Antibody 7 GL | | | | | | | | | | | | | | | | | | | | | | | |
| LO740029ALGFGL | Antibody 8 GL | | | | | | | | | L | | | | | | | | | | | | | | G |
| LO740054 | Antibody 9 | | | | | | | | | | | | | | | | | | | | | | | |
| LO740059 | Antibody 10 | | | | | | | | | | | | | | | | | | | | | | R | |
| LO740059ALG | Antibody 11 | | | | | | | | | L | | | | | | | | | | | | | R | G |
| LO740054ALGFGL | Antibody 12 GL | | | | | | | | | L | | | | | | | | | | | | | | G |
| LO740059ALGFGL | Antibody 11 GL | | | | | | | | | L | | | | | | | | | | | | | R | G |

| VH | Kabat Numbering | FW3 | | | | | | | | | | | | | | | | | | |
|---|---|---|---|---|---|---|---|---|---|---|---|---|---|---|---|---|---|---|---|---|
| | | 66 | 67 | 68 | 69 | 70 | 71 | 72 | 73 | 74 | 75 | 76 | 77 | 78 | 79 | 80 | 81 | 82 | 82a | 82b | 82c | 83 | 84 |
| Stella74 | Antibody 1 | R | V | T | I | S | G | D | T | P | K | N | Q | F | S | L | K | L | S | S | V | T | A |
| Stella74FGL | Antibody 1 GL | | | | | | | | | S | | | | | | | | | | | | | |
| LO740001 | Antibody 2 | | | | | | | | | | | | | | | | | | | | | | |
| LO740006 | Antibody 3 | | | | | | | | | | | | | | | | | | | | | | |
| LO740007 | Antibody 4 | | | | | | | | | | | | | | | | | | | | | | |
| LO740008 | Antibody 5 | | | | | | | | | | | | | | | | | | | | | | |
| LO740022 | Antibody 6 | | | | | | | | | | | | | | | | | | | | | | |
| LO740022FGL | Antibody 6 GL | | | | | | | | | S | | | | | | | | | | | | | |
| LO740029 | Antibody 7 | | | | | | | | | | | | | | | | | | | | | | |
| LO740029FGL | Antibody 7 GL | | | | | | | | | S | | | | | | | | | | | | | |
| LO740029ALGFGL | Antibody 8 GL | | | | | | | | | S | | | | | | | | | | | | | |
| LO740054 | Antibody 9 | | | | | | | | | | | | | | | | | | | | | | |
| LO740059 | Antibody 10 | | | | | | | | | | | | | | | | | | | | | | |
| LO740059ALG | Antibody 11 | | | | | | | | | | | | | | | | | | | | | | |
| LO740054ALGFGL | Antibody 12 GL | | | | | | | | | S | | | | | | | | | | | | | |
| LO740059ALGFGL | Antibody 11 GL | | | | | | | | | S | | | | | | | | | | | | | |

| VH | Kabat Numbering | FW3 | | | | | | | | | | CDR3 | | | | | | | |
|---|---|---|---|---|---|---|---|---|---|---|---|---|---|---|---|---|---|---|---|
| | | 85 | 86 | 87 | 88 | 89 | 90 | 91 | 92 | 93 | 94 | 95 | 96 | 97 | 98 | 99 | 100 | 100a | 100b |
| Stella74 | Antibody 1 | A | D | T | A | V | Y | Y | C | A | R | T | P | A | Y | D | G | D | A |
| Stella74FGL | Antibody 1 GL | | | | | | | | | | | | | | | | | | |
| LO740001 | Antibody 2 | | | | | | | | | | | | | | | | | | |
| LO740006 | Antibody 3 | | | | | | | | | | | | | | | | | | |
| LO740007 | Antibody 4 | | | | | | | | | | | | | | | | | | |
| LO740008 | Antibody 5 | | | | | | | | | | | | | | | | | | |
| LO740022 | Antibody 6 | | | | | | | | | | | | | | | F | | Q | D |
| LO740022FGL | Antibody 6 GL | | | | | | | | | | | | | | | F | | Q | D |
| LO740029 | Antibody 7 | | | | | | | | | | | | | | | F | | Q | D |
| LO740029FGL | Antibody 7 GL | | | | | | | | | | | | | | | F | | Q | D |
| LO740029ALGFGL | Antibody 8 GL | | | | | | | | | | | | | | | F | | Q | D |
| LO740054 | Antibody 9 | | | | | | | | | | | | | | | F | | Q | D |
| LO740059 | Antibody 10 | | | | | | | | | | | | | | | F | | Q | D |
| LO740059ALG | Antibody 11 | | | | | | | | | | | | | | | F | | Q | D |
| LO740054ALGFGL | Antibody 12 GL | | | | | | | | | | | | | | | F | | Q | D |
| LO740059ALGFGL | Antibody 11 GL | | | | | | | | | | | | | | | F | | Q | D |

TABLE 12-continued

Sequence alignment of VH domains of the mAbs described herein

| VH | Kabat Numbering | CDR3 | | | | | | | FW4 | | | | | | | | | | |
|---|---|---|---|---|---|---|---|---|---|---|---|---|---|---|---|---|---|---|---|
| | | 100c | 100d | 100e | 100f | 100g | 101 | 102 | 103 | 104 | 105 | 106 | 107 | 108 | 109 | 110 | 111 | 112 | 113 |
| Stella74 | Antibody 1 | R | A | D | F | F | D | V | W | G | R | G | T | L | V | T | V | S | S |
| Stella74FGL | Antibody 1 GL | | | | | | | | | | | | | | | | | | |
| LO740001 | Antibody 2 | | | | | | | | | | | | | | | | | | |
| LO740006 | Antibody 3 | | | | | | | | | | | | | | | | | | |
| LO740007 | Antibody 4 | | | | | | | | | | | | | | | | | | |
| LO740008 | Antibody 5 | | | | | | | | | | | | | | | | | | |
| LO740022 | Antibody 6 | | T | | | | | | | | | | | | | | | | |
| LO740022FGL | Antibody 6 GL | | T | | | | | | | | | | | | | | | | |
| LO740029 | Antibody 7 | | T | | | | | | | | | | | | | | | | |
| LO740029FGL | Antibody 7 GL | | T | | | | | | | | | | | | | | | | |
| LO740029ALGFGL | Antibody 8 GL | | T | | | | | | | | | | | | | | | | |
| LO740054 | Antibody 9 | | T | | | | | | | | | | | | | | | | |
| LO740059 | Antibody 10 | | T | | | | | | | | | | | | | | | | |
| LO740059ALG | Antibody 11 | | T | | | | | | | | | | | | | | | | |
| LO740054ALGFGL | Antibody 12 GL | | T | | | | | | | | | | | | | | | | |
| LO740059ALGFGL | Antibody 11 GL | | T | | | | | | | | | | | | | | | | |

TABLE 13

Sequence alignment of VL domains of the mAbs described herein

| | Kabat Numbering | FW1 | | | | | | | | | | | | | | | | | | |
|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 |
| Stella74 | Antibody 1 | D | I | V | M | T | Q | S | P | S | T | L | S | A | S | V | G | D | R | V |
| Stella74FGL | Antibody 1 GL | | | Q | | | | | | | | | | | | | | | | |
| LO740001 | Antibody 2 | | | | | | | | | | | | | | | | | | | |
| LO740006 | Antibody 3 | | | | | | | | | | | | | | | | | | | |
| LO740007 | Antibody 4 | | | | | | | | | | | | | | | | | | | |
| LO740008 | Antibody 5 | | | | | | | | | | | | | | | | | | | |
| LO740022 | Antibody 6 | | | | | | | | | | | | | | | | | | | |
| LO740022FGL | Antibody 6 GL | | | Q | | | | | | | | | | | | | | | | |
| LO740029 | Antibody 7 | | | | | | | | | | | | | | | | | | | |
| LO740029FGL | Antibody 7 GL | | | Q | | | | | | | | | | | | | | | | |
| LO740029ALGFGL | Antibody 8 GL | | | Q | | | | | | | | | | | | | | | | |
| LO740054 | Antibody 9 | | | | | | | | | | | | | | | | | | | |
| LO740059 | Antibody 10 | | | | | | | | | | | | | | | | | | | |
| LO740059ALG | Antibody 11 | | | | | | | | | | | | | | | | | | | |
| LO740054ALGFGL | Antibody 12 GL | | | Q | | | | | | | | | | | | | | | | |
| LO740059ALGFGL | Antibody 11 GL | | | Q | | | | | | | | | | | | | | | | |

| | Kabat Numbering | FW1 | | | | CDR1 | | | | | | | | | | | FW2 | | | |
|---|---|---|---|---|---|---|---|---|---|---|---|---|---|---|---|---|---|---|---|
| | | 20 | 21 | 22 | 23 | 24 | 25 | 26 | 27 | 28 | 29 | 30 | 31 | 32 | 33 | 34 | 35 | 36 | 37 | 38 |
| Stella74 | Antibody 1 | T | I | T | C | R | A | S | Q | G | I | S | S | W | L | A | W | Y | Q | Q |
| Stella74FGL | Antibody 1 GL | | | | | | | | | | | | | | | | | | | |
| LO740001 | Antibody 2 | | | | | | | | | | | | | | | | | | | |
| LO740006 | Antibody 3 | | | | | | | | | | | | | | | | | | | |
| LO740007 | Antibody 4 | | | | | | | | | | | | | | | | | | | |
| LO740008 | Antibody 5 | | | | | | | | | | | | | | | | | | | |
| LO740022 | Antibody 6 | | | | | | | | | | | | | | | | | | | |
| LO740022FGL | Antibody 6 GL | | | | | | | | | | | | | | | | | | | |
| LO740029 | Antibody 7 | | | | | | | | | | | | | | | | | | | |
| LO740029FGL | Antibody 7 GL | | | | | | | | | | | | | | | | | | | |
| LO740029ALGFGL | Antibody 8 GL | | | | | | | | | | | | | | | | | | | |
| LO740054 | Antibody 9 | | | | | | | | | | | | | | | | | | | |
| LO740059 | Antibody 10 | | | | | | | | | | | | | | | | | | | |
| LO740059ALG | Antibody 11 | | | | | | | | | | | | | | | | | | | |
| LO740054ALGFGL | Antibody 12 GL | | | | | | | | | | | | | | | | | | | |
| LO740059ALGFGL | Antibody 11 GL | | | | | | | | | | | | | | | | | | | |

TABLE 13-continued

Sequence alignment of VL domains of the mAbs described herein

| | | FW2 | | | | | | | | | | CDR2 | | | | | | |
|---|---|---|---|---|---|---|---|---|---|---|---|---|---|---|---|---|---|---|
| | Kabat Numbering | 39 | 40 | 41 | 42 | 43 | 44 | 45 | 46 | 47 | 48 | 49 | 50 | 51 | 52 | 53 | 54 | 55 | 56 |
| Stella74 | Antibody 1 | K | P | G | R | A | P | K | V | L | I | Y | K | A | S | T | L | E | S |
| Stella74FGL | Antibody 1 GL | | | | K | | | | | | | | | | | | | | |
| LO740001 | Antibody 2 | | | | | | | | | | | | | | | | | | |
| LO740006 | Antibody 3 | | | | | | | | | | | | | | | | | | |
| LO740007 | Antibody 4 | | | | | | | | | | | | | | | | | | |
| LO740008 | Antibody 5 | | | | | | | | | | | | | | | | | | |
| LO740022 | Antibody 6 | | | | | | | | | | | | | | | | | | |
| LO740022FGL | Antibody 6 GL | | | | K | | | | | | | | | | | | | | |
| LO740029 | Antibody 7 | | | | | | | | | | | | | | | | | | |
| LO740029FGL | Antibody 7 GL | | | | K | | | | | | | | | | | | | | |
| LO740029ALGFGL | Antibody 8 GL | | | | K | | | | | | | | | | | | | | |
| LO740054 | Antibody 9 | | | | | | | | | | | | | | | | | | |
| LO740059 | Antibody 10 | | | | G | | | | | | | | | | | | | | |
| LO740059ALG | Antibody 11 | | | | G | | | | | | | | | | | | | | |
| LO740054ALGFGL | Antibody 12 GL | | | | K | | | | | | | | | | | | | | |
| LO740059ALGFGL | Antibody 11 GL | | | | K | | | | | | | | | | | | | | |

| | | FW3 | | | | | | | | | | | | | | | |
|---|---|---|---|---|---|---|---|---|---|---|---|---|---|---|---|---|---|
| | Kabat Numbering | # | # | # | # | # | # | # | # | # | # | # | # | # | # | # | # |
| Stella74 | Antibody 1 | G | V | P | S | R | F | S | G | S | G | S | G | T | D | F | T | L |
| Stella74FGL | Antibody 1 GL | | | | | | | | | | | | | | E | | | |
| LO740001 | Antibody 2 | | | | | | | | | | | | | | | | | |
| LO740006 | Antibody 3 | | | | | | | | | | | | | | | | | |
| LO740007 | Antibody 4 | | | | | | | | | | | | | | | | | |
| LO740008 | Antibody 5 | | | | | | | | | | | | | | | | | |
| LO740022 | Antibody 6 | | | | | | | | | | | | | | | | | |
| LO740022FGL | Antibody 6 GL | | | | | | | | | | | | | | E | | | |
| LO740029 | Antibody 7 | | | | | | | | | | | | | | | | | |
| LO740029FGL | Antibody 7 GL | | | | | | | | | | | | | | E | | | |
| LO740029ALGFGL | Antibody 8 GL | | | | | | | | | | | | | | E | | | |
| LO740054 | Antibody 9 | | | | | | | | | | | | | | | | | |
| LO740059 | Antibody 10 | | | | | | | | | | | | | | | | | |
| LO740059ALG | Antibody 11 | | | | | | | | | | | | | | | | | |
| LO740054ALGFGL | Antibody 12 GL | | | | | | | | | | | | | | E | | | |
| LO740059ALGFGL | Antibody 11 GL | | | | | | | | | | | | | | E | | | |

| | | FW3 | | | | | | | | | | | | | | | CDR3 | |
|---|---|---|---|---|---|---|---|---|---|---|---|---|---|---|---|---|---|---|
| | Kabat Numbering | # | # | # | # | # | # | # | # | # | # | # | # | # | # | # | # | # |
| Stella74 | Antibody 1 | T | I | S | S | L | Q | P | E | D | F | A | T | Y | Y | C | Q | Q |
| Stella74FGL | Antibody 1 GL | | | | | | | | D | | | | | | | | | |
| LO740001 | Antibody 2 | | | | | | | | | | | | | | | | | D |
| LO740006 | Antibody 3 | | | | | | | | | | | | | | | | | |
| LO740007 | Antibody 4 | | | | | | | | | | | | | | | | | |
| LO740008 | Antibody 5 | | | | | | | | | | | | | | | | | |
| LO740022 | Antibody 6 | | | | | | | | | | | | | | | | A | N |
| LO740022FGL | Antibody 6 GL | | | | | | | | D | | | | | | | | A | N |
| LO740029 | Antibody 7 | | | | | | | | | | | | | | | | | |
| LO740029FGL | Antibody 7 GL | | | | | | | | D | | | | | | | | | |
| LO740029ALGFGL | Antibody 8 GL | | | | | | | | D | | | | | | | | | |
| LO740054 | Antibody 9 | | | | | | | | | | | | | | | | | |
| LO740059 | Antibody 10 | | | | | | | | | | | | | | | | | |
| LO740059ALG | Antibody 11 | | | | | | | | | | | | | | | | | |
| LO740054ALGFGL | Antibody 12 GL | | | | | | | | D | | | | | | | | | |
| LO740059ALGFGL | Antibody 11 GL | | | | | | | | D | | | | | | | | | |

TABLE 13-continued

Sequence alignment of VL domains of the mAbs described herein

|  | Kabat Numbering | CDR3 | | | | | | | FW4 | | | | | | | | | |
|---|---|---|---|---|---|---|---|---|---|---|---|---|---|---|---|---|---|---|
|  |  | # | # | # | # | # | # | # | # | # | # | # | # | # | # | # | # | # |
| Stella74 | Antibody 1 | S | Y | S | T | P | W | T | F | G | Q | G | T | K | L | E | I | K |
| Stella74FGL | Antibody 1 GL | | | | | | | | | | | | | | | | | |
| LO740001 | Antibody 2 | I | S | F | P | | | | | | | | | | | | | |
| LO740006 | Antibody 3 | | L | Y | P | | | | | | | | | | | | | |
| LO740007 | Antibody 4 | | H | H | P | N | | D | | | | | | | | | | |
| LO740008 | Antibody 5 | | L | I | P | Q | | D | | | | | | | | | | |
| LO740022 | Antibody 6 | I | A | F | P | | | | | | | | | | | | | |
| LO740022FGL | Antibody 6 GL | I | A | F | P | | | | | | | | | | | | | |
| LO740029 | Antibody 7 | | H | H | P | | | | | | | | | | | | | |
| LO740029FGL | Antibody 7 GL | | H | H | P | | | | | | | | | | | | | |
| LO740029ALGFGL | Antibody 8 GL | | H | H | P | | | | | | | | | | | | | |
| LO740054 | Antibody 9 | | H | H | P | | | | | | | | | | | | | |
| LO740059 | Antibody 10 | | H | H | P | | | | | | | | | | | | | |
| LO740059ALG | Antibody 11 | | H | H | P | | | | | | S | | | | | | | |
| LO740054ALGFGL | Antibody 12 GL | | H | H | P | | | | | | S | | | | | | | |
| LO740059ALGFGL | Antibody 11 GL | | H | H | P | | | | | | | | | | | | | |

TABLE 14

Sequence identity across the VH and VL CDRs of the mAbs described herein

| Identidy across VH and VL CDRs | | | | | | Identidy across 6 CDRS | | |
|---|---|---|---|---|---|---|---|---|
|  | Antibody 1 | Antibody 1 GL | Antibody 2 | Antibody 3 | Antibody 4 | Antibody 5 | Antibody 6 | Antibody 6 GL |
| Antibody 1 | - | 100% | 92% | 95% | 92% | 92% | 84% | 84% |
| Antibody 1 GL | | - | 92% | 95% | 92% | 92% | 84% | 84% |
| Antibody 2 | | | - | 93% | 90% | 90% | 89% | 89% |
| Antibody 3 | | | | - | 93% | 95% | 86% | 86% |
| Antibody 4 | | | | | - | 95% | 83% | 83% |
| Antibody 5 | | | | | | - | 83% | 83% |
| Antibody 6 | | | | | | | - | 100% |
| Antibody 6 GL | | | | | | | | - |
| Antibody 7 | | | | | | | | |
| Antibody 7 GL | | | | | | | | |
| Antibody 8 GL | | | | | | | | |
| Antibody 9 | | | | | | | | |
| Antibody 10 | | | | | | | | |
| Antibody 11 | | | | | | | | |
| Antibody 11 GL | | | | | | | | |
| Antibody 12 GL | | | | | | | | |

TABLE 14-continued

Sequence identity across the VH and VL CDRs of the mAbs described herein

| | Antibody 7 | Antibody 7 GL | Antibody 8 GL | Antibody 9 | Antibody 10 | Antibody 11 | Antibody 11 GL | Antibody 12 GL |
|---|---|---|---|---|---|---|---|---|
| Antibody 1 | 89% | 89% | 84% | 87% | 86% | 81% | 81% | 83% |
| Antibody 1 GL | 89% | 89% | 84% | 87% | 86% | 81% | 81% | 83% |
| Antibody 2 | 87% | 87% | 83% | 86% | 84% | 80% | 80% | 81% |
| Antibody 3 | 90% | 90% | 86% | 89% | 87% | 83% | 83% | 84% |
| Antibody 4 | 90% | 90% | 86% | 89% | 87% | 83% | 83% | 84% |
| Antibody 5 | 87% | 87% | 83% | 86% | 84% | 80% | 80% | 81% |
| Antibody 6 | 92% | 92% | 87% | 90% | 89% | 84% | 84% | 86% |
| Antibody 6 GL | 92% | 92% | 87% | 90% | 89% | 84% | 84% | 86% |
| Antibody 7 | - | 100% | 95% | 98% | 96% | 92% | 92% | 93% |
| Antibody 7 GL | | - | 95% | 98% | 96% | 92% | 92% | 93% |
| Antibody 8 GL | | | - | 93% | 92% | 95% | 96% | 98% |
| Antibody 9 | | | | - | 98% | 93% | 93% | 95% |
| Antibody 10 | | | | | - | 95% | 95% | 93% |
| Antibody 11 | | | | | | - | 100% | 98% |
| Antibody 11 GL | | | | | | | - | 98% |
| Antibody 12 GL | | | | | | | | - |

TABLE 15

Sequence identity across the VH or VL CDRs of the mAbs described herein

| VH CDR (1,2,3) % identity | | | | | | | | |
|---|---|---|---|---|---|---|---|---|
| | Antibody 1 | Antibody 1 GL | Antibody 2 | Antibody 3 | Antibody 4 | Antibody 5 | Antibody 6 | Antibody 6 GL |
| Antibody 1 | - | 100% | 100% | 100% | 100% | 100% | 89% | 89% |
| Antibody 1 GL | | - | 100% | 100% | 100% | 100% | 89% | 89% |
| Antibody 2 | | | - | 100% | 100% | 100% | 89% | 89% |
| Antibody 3 | | | | - | 100% | 100% | 89% | 89% |
| Antibody 4 | | | | | - | 100% | 89% | 89% |
| Antibody 5 | | | | | | - | 89% | 89% |
| Antibody 6 | | | | | | | - | 100% |
| Antibody 6 GL | | | | | | | | - |
| Antibody 7 | | | | | | | | |
| Antibody 7 GL | | | | | | | | |
| Antibody 8 GL | | | | | | | | |
| Antibody 9 | | | | | | | | |
| Antibody 10 | | | | | | | | |
| Antibody 11 | | | | | | | | |
| Antibody 11 GL | | | | | | | | |
| Antibody 12 GL | | | | | | | | |

TABLE 15-continued

Sequence identity across the VH or VL CDRs of the mAbs described herein

| VH CDR (1,2,3) % identity | | | | | | | | |
|---|---|---|---|---|---|---|---|---|
| | Antibody 7 | Antibody 7 GL | Antibody 8 GL | Antibody 9 | Antibody 10 | Antibody 11 | Antibody 11 GL | Antibody 12 GL |
| Antibody 1 | 89% | 89% | 81% | 86% | 84% | 76% | 76% | 78% |
| Antibody 1 GL | 89% | 89% | 81% | 86% | 84% | 76% | 76% | 78% |
| Antibody 2 | 89% | 89% | 81% | 86% | 84% | 76% | 76% | 78% |
| Antibody 3 | 89% | 89% | 81% | 86% | 84% | 76% | 76% | 78% |
| Antibody 4 | 89% | 89% | 81% | 86% | 84% | 76% | 76% | 78% |
| Antibody 5 | 89% | 89% | 81% | 86% | 84% | 76% | 76% | 78% |
| Antibody 6 | 100% | 100% | 92% | 97% | 94% | 86% | 86% | 89% |
| Antibody 6 GL | 100% | 100% | 92% | 97% | 94% | 86% | 86% | 89% |
| Antibody 7 | - | 100% | 92% | 97% | 94% | 86% | 86% | 89% |
| Antibody 7 GL | | - | 92% | 97% | 94% | 86% | 86% | 89% |
| Antibody 8 GL | | | - | 89% | 86% | 94% | 94% | 97% |
| Antibody 9 | | | | - | 97% | 89% | 89% | 92% |
| Antibody 10 | | | | | - | 92% | 92% | 89% |
| Antibody 11 | | | | | | - | 100% | 97% |
| Antibody 11 GL | | | | | | | - | 97% |
| Antibody 12 GL | | | | | | | | - |

| VH CDR (1,2,3) % identity | | | | | | | | |
|---|---|---|---|---|---|---|---|---|
| | Antibody 1 | Antibody 1 GL | Antibody 2 | Antibody 3 | Antibody 4 | Antibody 5 | Antibody 6 | Antibody 6 GL |
| Antibody 1 | - | 100% | 81% | 88% | 81% | 81% | 77% | 77% |
| Antibody 1 GL | | - | 81% | 88% | 81% | 81% | 77% | 77% |
| Antibody 2 | | | - | 85% | 77% | 77% | 88% | 88% |
| Antibody 3 | | | | - | 85% | 88% | 81% | 81% |
| Antibody 4 | | | | | - | 88% | 74% | 74% |
| Antibody 5 | | | | | | - | 74% | 74% |
| Antibody 6 | | | | | | | - | 100% |
| Antibody 6 GL | | | | | | | | - |
| Antibody 7 | | | | | | | | |
| Antibody 7 GL | | | | | | | | |
| Antibody 8 GL | | | | | | | | |
| Antibody 9 | | | | | | | | |
| Antibody 10 | | | | | | | | |
| Antibody 11 | | | | | | | | |
| Antibody 11 GL | | | | | | | | |
| Antibody 12 GL | | | | | | | | |

TABLE 15-continued

Sequence identity across the VH or VL CDRs of the mAbs described herein

| VH CDR (1,2,3) % identity | | | | | | | | |
|---|---|---|---|---|---|---|---|---|
| | Antibody 7 | Antibody 7 GL | Antibody 8 GL | Antibody 9 | Antibody 10 | Antibody 11 | Antibody 11 GL | Antibody 12 GL |
| Antibody 1 | 88% | 88% | 88% | 88% | 88% | 88% | 88% | 00% |
| Antibody 1 GL | 88% | 88% | 88% | 88% | 88% | 88% | 88% | 88% |
| Antibody 2 | 85% | 85% | 85% | 85% | 85% | 85% | 85% | 85% |
| Antibody 3 | 92% | 92% | 92% | 92% | 92% | 92% | 92% | 92% |
| Antibody 4 | 92% | 92% | 92% | 92% | 92% | 92% | 92% | 92% |
| Antibody 5 | 85% | 85% | 85% | 85% | 85% | 85% | 85% | 85% |
| Antibody 6 | 81% | 81% | 81% | 81% | 81% | 81% | 81% | 81% |
| Antibody 6 GL | 81% | 81% | 81% | 81% | 81% | 81% | 81% | 81% |
| Antibody 7 | - | 100% | 100% | 100% | 100% | 100% | 100% | 100% |
| Antibody 7 GL | | - | 100% | 100% | 100% | 100% | 100% | 100% |
| Antibody 8 GL | | | - | 100% | 100% | 100% | 100% | 100% |
| Antibody 9 | | | | - | 100% | 100% | 100% | 100% |
| Antibody 10 | | | | | - | 100% | 100% | 100% |
| Antibody 11 | | | | | | - | 100% | 100% |
| Antibody 11 GL | | | | | | | - | 100% |
| Antibody 12 GL | | | | | | | | - |

The invention claimed is:

1. An isolated antibody molecule for human Interleukin-18(IL-18) which specifically binds to an epitope of human IL-18 which wholly or partially overlaps with the IL-18BP binding site on human IL-18, wherein the antibody molecule comprises:
   (a) a HCDR1 having an amino acid sequence identical to or comprising 3 or fewer amino acid residue substitutions relative to SEQ ID NO: 153;
   (b) a HCDR2 having an amino acid sequence identical to or comprising 4 or fewer amino acid residue substitutions relative to SEQ ID NO: 154;
   (c) a HCDR3 having an amino acid sequence identical to or comprising 5 or fewer amino acid residue substitutions relative to SEQ ID NO: 155;
   (d) a LCDR1 having an amino acid sequence identical to or comprising 4 or fewer amino acid residue substitutions relative to SEQ ID NO: 158;
   (e) a LCDR2 having an amino acid sequence identical to or comprising 4 or fewer amino acid residue substitutions relative to SEQ ID NO: 159; and
   (f) a LCDR3 having an amino acid sequence identical to or comprising 9 or fewer amino acid residue substitutions relative to SEQ ID NO: 160.

2. The antibody molecule according to claim 1, wherein the antibody molecule comprises an antibody VH domain and an antibody VL domain,
   wherein the VH domain comprises HCDR1, HCDR2, HCDR3 having the amino acid sequences of SEQ ID NOS: 153, 154 and 155, respectively; and,
   the VL domain comprises LCDR1, LCDR2, LCDR3 having the amino acid sequences of SEQ ID NOS: 158, 159 and 160, respectively.

3. The antibody molecule according to claim 1, wherein the heavy and/or light chain framework regions are germlined to human germline gene segment sequences.

4. The antibody molecule according to claim 2, wherein the amino acid sequence of the antibody VH domain is at least 90% identical with SEQ ID NO: 152 and wherein the amino acid sequence of the antibody VL domain is at least 90% identical with SEQ ID NO: 157.

5. The antibody molecule according to claim 4, wherein the amino acid sequence of the antibody VH domain is SEQ ID NO: 152 and the amino acid sequence of the antibody VL domain sequence is SEQ ID NO: 157.

6. The antibody molecule according to claim 1, wherein the antibody molecule is an IgG1 with YTE and TM mutations in the Fc region.

7. A composition comprising an isolated antibody molecule according to claim 1 and a pharmaceutically acceptable excipient.

8. The antibody molecule according to claim 2, wherein the antibody molecule is an IgG1 with YTE and TM mutations in the Fc region.

9. The antibody molecule according to claim 4, wherein the antibody molecule is an IgG1 with YTE and TM mutations in the Fc region.

10. The antibody molecule according to claim 5, wherein the antibody molecule is an IgG1 with YTE and TM mutations in the Fc region.

11. A composition comprising an isolated antibody molecule according to claim 2 and a pharmaceutically acceptable excipient.

12. A composition comprising an isolated antibody molecule according to claim 4 and a pharmaceutically acceptable excipient.

13. A composition comprising an isolated antibody molecule according to claim 5 and a pharmaceutically acceptable excipient.

* * * * *